United States Patent
Schofield et al.

(10) Patent No.: US 9,228,224 B2
(45) Date of Patent: Jan. 5, 2016

(54) METHOD FOR ASSAYING OGFOD1 ACTIVITY

(75) Inventors: Christopher Joseph Schofield, Oxford (GB); Alexander Wolf, Oxford (GB); Wei Ge, Oxford (GB); Armin Thalhammer, Oxford (GB); Christoph Loenarz, Oxford (GB); Peter John Ratcliffe, Oxford (GB); Matthew Edward Cockman, Oxford (GB)

(73) Assignee: ISIS INNOVATION LIMITED, Oxford (GB)

( * ) Notice: Subject to any disclaimer, the term of this patent is extended or adjusted under 35 U.S.C. 154(b) by 0 days.

(21) Appl. No.: 13/985,243

(22) PCT Filed: Feb. 10, 2012

(86) PCT No.: PCT/GB2012/050303
§ 371 (c)(1),
(2), (4) Date: Oct. 25, 2013

(87) PCT Pub. No.: WO2012/110789
PCT Pub. Date: Aug. 23, 2012

(65) Prior Publication Data
US 2014/0051106 A1    Feb. 20, 2014

(30) Foreign Application Priority Data
Feb. 15, 2011    (GB) .................................. 1102659.8

(51) Int. Cl.
*C12Q 1/26*    (2006.01)

(52) U.S. Cl.
CPC ........ *C12Q 1/26* (2013.01); *G01N 2333/90245* (2013.01)

(58) Field of Classification Search
None
See application file for complete search history.

(56) References Cited

U.S. PATENT DOCUMENTS

2010/0240069 A1    9/2010    Broadwater et al.

FOREIGN PATENT DOCUMENTS

| WO | WO-01/98353 A2 | 12/2001 |
| WO | WO-03/080566 A2 | 10/2003 |
| WO | WO-2007/034214 A1 | 3/2007 |
| WO | WO-2008/155556 A1 | 12/2008 |

OTHER PUBLICATIONS

Saito et al., "OGFOD1, a member of the 2-oxoglutarate and iron dependent dioxygenase family, functions in ischemic signaling," FEBS Letts. 584(15):3340-3347 (2010).
Tiainen et al., "Characterization of recombinant human prolyl 3-hydroxylase isoenzyme 2, an enzyme modifying the basement membrane collagen IV," J Biol Chem. 283(28):19432-19439 (2008).
Wehner et al., "OGFOD1, a novel modulator of eukaryotic translation initiation factor 2α phosphorylation and the cellular response to stress," Mol Cell Biol. 30(8):2006-2016 (2010).
International Search Report International Application No. PCT/GB2012/050303, mailed Jun. 25, 2012 (4 pages).
Eilbracht et al., "NO66, a highly conserved dual location protein in the nucleolus and in a special type of synchronously replicating chromatin," Mol Biol Cell. 15(4):1816-32 (2004).
Hewitson et al., "The HIF pathway as a therapeutic target," Drug Discov Today. 9(16):704-11 (2004).
Komiya et al., "Mina53, a novel c-Myc target gene, is frequently expressed in lung cancers and exerts oncogenic property in NIH/3T3 cells," J Cancer Res Clin Oncol. 136(3):465-73 (2010).
Okamoto et al., "Mina, an Il4 repressor, controls T helper type 2 bias," Nat Immunol. 10(8):872-9 (2009).
Rose et al., "Inhibition of 2-oxoglutarate dependent oxygenases," Chem Soc Rev. 40(8):4364-97 (2011).
Sinha et al., "Regulation of the osteoblast-specific transcription factor Osterix by NO66, a Jumonji family histone demethylase," EMBO J. 29(1):68-79 (2010).
Tsuneoka et al., "A novel myc target gene, mina53, that is involved in cell proliferation," J Biol Chem. 277(38):35450-9 (2002).

*Primary Examiner* — Nashaat Nashed
(74) *Attorney, Agent, or Firm* — Clark & Elbing LLP; Susan M. Michaud

(57) ABSTRACT

The present invention relates to assays for monitoring activity of OGFOD1 activity, in particular, to assays for identifying modulators of OGFOD1 activity. The invention also relates to assays to monitor the prolyl hydroxylase activity of OGFOD1 on its substrate, the human ribosomal protein RPS23. The invention also enables the introduction of 3-hydroxyprolyl residues into peptides and proteins.

16 Claims, 6 Drawing Sheets

Figure 1

```
                       *        20         *        40         *
HUMAN     : MNGKRPAEPGPARVGKKGKKEVMAEFSDAVTEETLKKQVAEAWSRRTPFSH : 51
ORANGUTAN : MNGKRPAEPGPARVGKKRKKEVMAEFSDAVTEETLKKQVAEAWSRRTPFSH : 51
COW       : MNGKRPAEPGSDRAGKKVKKEVMAKFSDAVTEETLKKQVAEAWSRRTPFRH : 51
RAT       : MNGKRPADPGPARPMKKGKKQVAAEFSDAVTEEILRKQVAEAWSCRTPFSH : 51
MOUSE     : MNGKRPADPGPARPMKKGKKQVSAEFSDAVTEEILRKQVAEAWSCRTPFSH : 51
            MNGKRPA PGpaR  KK KK2V AeFSDAVTEE L4KQVAEAWS RTPFsH

60         *        80         *       100
HUMAN     : EVIVMDMDPFLHCVIPNFIQSQDFLEGLQKELMNLDFHEKYNDLYKFQQSD : 102
ORANGUTAN : EVIVMDMDPFLHCVIPNFIQSQDFLEGLQKELMNLDFHEKYNDLYKFQQSD : 102
COW       : EAIVMDMDPFLHCVIPNFIQSQNFLEGLQKELLNLDFHEKYNDLYKFQQSD : 102
RAT       : EAIALDMDPFLHCVIPNFIQSQDFLEGLQKELLSLDFHEKYNDLYKFQQSD : 102
MOUSE     : EAIALDMDPFLHCVIPNFIQSQDFLEGLHKELLSLDFHEKYNDLYKFQQSD : 102
            E I 6DMDPFLHCVIPNFIQSQ1FLEGLqKEL6 LDFHEKYNDLYKFQQSD

*       120         *       140         *
HUMAN     : DLKKRREPHISTLRKILFEDFRSWLSDISKIDLESTIDMSCAKYEFTDALL : 153
ORANGUTAN : DLKKRREPHISALRKILFEDFRSWLSDISKIDLESTIDMSCAKYEFTDALL : 153
COW       : DLKKRREPHICALRKILFEHFRSWISDISKIDLESTIDMSCAKYEFSDALL : 153
RAT       : DLKKRKEPHISALRTLMFEDFRAWLSKVSGIDLEATVDMSCAKYEFTDALL : 153
MOUSE     : DLKNRKEPHISALRKLMFEDFRAWLSKVSGIDLEPTIDMSCAKYEFTDALL : 153
            DLKkR4EPHIsaLRk66FEdFR W6S  6S IDLE T6DMSCAKYEF3DALL

160         *       180         *       200
HUMAN     : CHDDELEGRRIAFILYLVPPWDRSMGGTLDLYSIDEHFQPKQIVKSLIPSW : 204
ORANGUTAN : CHDDELEGRRIAFILYLVPPWDRSLGGTLDLYSIDEHFQPKQIVKSLIPSW : 204
COW       : CHDDELEGRRIAFILYLVPPWDASLGGTLDLFSVDEHFQPKQIVKSLIPSW : 204
RAT       : CHDDELEGRRIAFILYLVPSWDRDLGGTLDLYDTDEHLQPKQIVKSLVPAW : 204
MOUSE     : CHDDELEGRRIAFILYLVPSWDRDLGGTLDLYDTDEHLQPKQIVKSLIPSW : 204
            CHDDELEGRRIAFILYLVP WDr 6GGTLDL5  DEH QPKQIVKSL6PsW

*       220         *       240         *
HUMAN     : NKLVFFEVSPVSFHQVSEVLSEEKSRLSISGWFHGPSLIRPPNYFEPEIER : 255
ORANGUTAN : NKLVFFEVSPVSFHQVSEVLSEEKSRLSISGWFHGPSLIRPPNHFEPEIER : 255
COW       : NTLVFFEVSPVSFHQVSEVLSEEKSRLSISGWFHGPSLIRPPTYFEPLIAR : 255
RAT       : NKLVFFEVSPVSFHQVSEVLSEELTRLSISGWFHGPSLARPPTYFEPEVER : 255
MOUSE     : NKLVFFEVSPVSFHQVSEVLSEETSRLSISGWFYGPSLIRPPTYFEPEIER : 255
            NkLVFFEVSPVSFHQVSEVLSEE 3RLSISGWFhGPSLtRPP yFEPp6pR

260         *       280         *       300
HUMAN     : SPHIPQDHEILYDWINPTYLDMDYQMQIQEEFEESSEILLKEFLKPEKFTK : 306
ORANGUTAN : SPHIPQDHEILYDWINPTYLDMDYQMQIQEEFEESSEILLKEFLKPEKMK : 306
COW       : SPHIPQDHEILYDWINPTYLDMEYQAQIQEEFEESSEILLKEFLQPEKAE : 306
RAT       : SPHIPQDHEILYEWINPAYLEMDYQMQIQEEFEERSEILLKEFLKPEKAK : 306
MOUSE     : NPHIPQDHEILYEWINPAYLEMDYQMQIQEEFEERSEILLKEFLKPEKAE : 306
            sPHIPQDHEILY WINP YL MdYQ QIQEEFEE SEILLKEFLkPEKF

*       320         *       340         *
HUMAN     : VCEALEHGHVEWSSRGPPNKRFYEKAEESKLPEILKECMKLFRSEALFLLL : 357
ORANGUTAN : VCEALEHGDVEWSSRGPPNKRFYEKAEESKLPEILKECMKLFHSEALFLLL : 357
COW       : VCEALERGRVEWSSRGPPNKRFYEKAEESQLPDILRDCMALFRSEAMFLLL : 357
RAT       : VCEALEKGDVEWKSHGPPNKRFYEKAKESNLPDVLKECMGLFHSEAMFLLL : 357
MOUSE     : VCEALEKGDVEWKSHGPPNKRFYEKAEENNLPDVLKECMGLFRSEALFLLL : 357
            VCEALE G VEW S GPPNKRFYEKAeEs LP 6L4eCM LF SEA6FLLL

360         *       380         *       400
HUMAN     : SNFTGLKLHFLAPSEEDEMNDKKEAET---TDITEEGTSHSPPEPENNQMA : 405
ORANGUTAN : SNFTGLKLHFLAPSEEDEMNDKKEAEA---ADITEEGTSHSPPEPENNQTA : 405
COW       : SNFTGLKLHFLAPSE-DEPEDKKERDAVSAAENTEEGTSHSSSEPENSWAA : 407
RAT       : SNFTGLKLHFLAPSEDDETEDKGEGETASAAGGTEEGTSQSPPGPEDNQAA : 408
MOUSE     : SNLTGLKLHFLAPSEDDETEEKGEGETASAAAGTEEGTSRRESGPENNQVA : 408
            SNfTGLKLHFLAPSE DE  dK E e   a   TEEGTS sp PElnq A
```

Fig. 1 (continued)

```
                    *         420         *         440         *         46
HUMAN      : ISNNSQQSNDQTDPEPEENETKKESSVPMCQGELRHWKTGHYTLIHDHSKA : 456
ORANGUTAN  : ISNNSQQSNDQTDPEPEENETKKESSVPMCQGELRRWKTGHYTLIHDHSKA : 456
COW        : TSDSSLQSEGPTDPE--EDEAKKESSVPTCQGELRHWKTGHYTLIHDNSKT : 456
RAT        : VGSHSQENGEQADPEPQEDEAKKESSVPMCQGELRRWKTGHYTLVHDNSKT : 459
MOUSE      : AGSHSQENGEQADPEAQEEEAKKESSVPMCQGELRRWKTGHYTLVHDNTKT : 459
               Sq2   eq DPE  E E KKESSVP CQGELR WKTGHYTL6HD 3K

0         *         480         *         500         *
HUMAN      : EFALDLILYCGCEGWEPEYGGFTSYIAKGEDEELLTVNPESNSLALVYRDR : 507
ORANGUTAN  : EFALDLILYCGCEGWEPEYGGFTSYIAKGEDEELLTVNPESNSLALVYRDR : 507
COW        : EFALDLLLYCGCEGWEPEYGGFTSYIAKGEDEELLTVNPENNSLALVYRDR : 507
RAT        : EFALDLFLYCGCEGWEPEYGGFTSYIAKGEDEELLIVNPENNALALVYRDR : 510
MOUSE      : EFALDLFLYCGCEGWEPEYGGFTSYIAKGEDEELLIVNPENNSLALVYRDR : 510
             EFALDL LYCGCEGWEPEYGGFTSYIAKGEDEELL VNPE NsLALVYRDR

520         *         540
HUMAN      : ETLKFVKHINHRSLEQKKIFPNRTGFWDFSFIYYE : 542
ORANGUTAN  : ETLKFVKHINHRSLEQKKIFPNRTGFWDFSFIYYE : 542
COW        : ETLKFVKHINHRSLEQKKSFPNRTGFWDFSFVYYE : 542
RAT        : ETLRFVKHINHRSLEQRNIFPNRSGFWDFAFMYYE : 545
MOUSE      : ETLRFVKHINHRSLEQSKAFPSRSGFWDFAFIYYE : 545
             ETL4FVKHINHRSLEQ k FPnR3GFWDF F6YYE
```

Figure 2

```
OGFOD1   58 MDPFLHCVIPNEIQSQDFLEGLQKELM-NLDFHEKYNLYKFQQSD 102
TPA1     50 SQPYNWGTIHELV-NDDLLRAVRKEIETEIHFTKKETDIYRVNQSG  94
EGLN1   202 MNKHGICVVDDFL-GKETGQQIGDEVR-ALHDTGKFTDGQLVSQKS 245
EGLN2   186 MRYYGICVKDSFL-GAALGGRVLAEVE-ALKRGGRLRDGQLVSQRA 229
EGLN3    23 LHEVGFCYLDNEL-GEVVGDCVLERVK-QLHCTGALRDGQLAGPRA  66
sec. struct.

OGFOD1  103 DLKKR------------REPHISTLRKIIF----EDFRSWLSDIS 131
TPA1     95 DLANL----SGLDWDDLSRLPNLFKLRQILYSKQYRDFFGYVTKAG 136
EGLN1   246 D-SSKDIRGDKITWIE-GKEPGCETI-GLLMSSMDDLIRHCNGKLG 288
EGLN2   230 I-PPRSIRGDQIAWVE-GHEPGCRSI-GALMAHVDAVIRHCAGRLG 272
EGLN3    67 GVSKRHLRGDQITWIG-GNEEGCEAIL-SFLLSLIDRLVLYCGSRLG 110
sec. struct.

OGFOD1  132 KIDLESTIDMSCAKYE-FTDALLCHDEL--EGRRIAFILY---V 171
TPA1    137 KLS-GSKTDMSINTYT-KGCHLLTHDVI--GSRRLSFILYPDPD 178
EGLN1   289 SYKINGRTKAMVACYPGNGTGYVRHVDNPNGDGRCVTCIYY---N 331
EGLN2   273 SYVINGRTKAMVACYPGNGLGYVRHVDNPHGDGRCITCIY----N 315
EGLN3   111 KYYVKERSKAMVACYPGNGTGYVRHVDNPNGDGRCITCIY----N 153
sec. struct.             I.          II.          III.

OGFOD1  172 PPNDRSM-GGTLDLYSIDEHFQPKQ-IVKSLIRSWNKLVFFEVSPV 215
TPA1    179 RKAKSHY-GCGLRLFPSILPNVPHSDPSAKLVFQFNQIAFFKVLPG 223
EGLN1   332 KDWDAKVSGGILRIFP-----EGKA-QFADIEPKFDRLLFWSDRR 371
EGLN2   316 QNWDVKVHGGLLQIFP-----EGRP-VVANIEQLFDRLLIFWSDRR 355
EGLN3   154 KNWDAKLHGGILRIFP-----EGKS-FIADVERIFDRLLFEWSDRR 193
sec. struct.         IV.    V.                        VI.

OGFOD1  216 -SFHQVSEVLSEEKSRLSLSGNFHGP-SLTRPPNYF 249
TPA1    224 FSFDVEEVKV-DKHRLSIQGWYHIP---------- 248
EGLN1   372 -NPHEVQPAYA---TRYAITVWYFDADERARAKVKY 403
EGLN2   356 -NPHEVKPAYA---TRYAITVWYFDAKERAAAKDKY 387
EGLN3   194 -NPHEVQPSYA---TRYAMTVWYFDAEERAEAKKKF 225
sec. struct.    VII.       VIII.
```

Figure 3

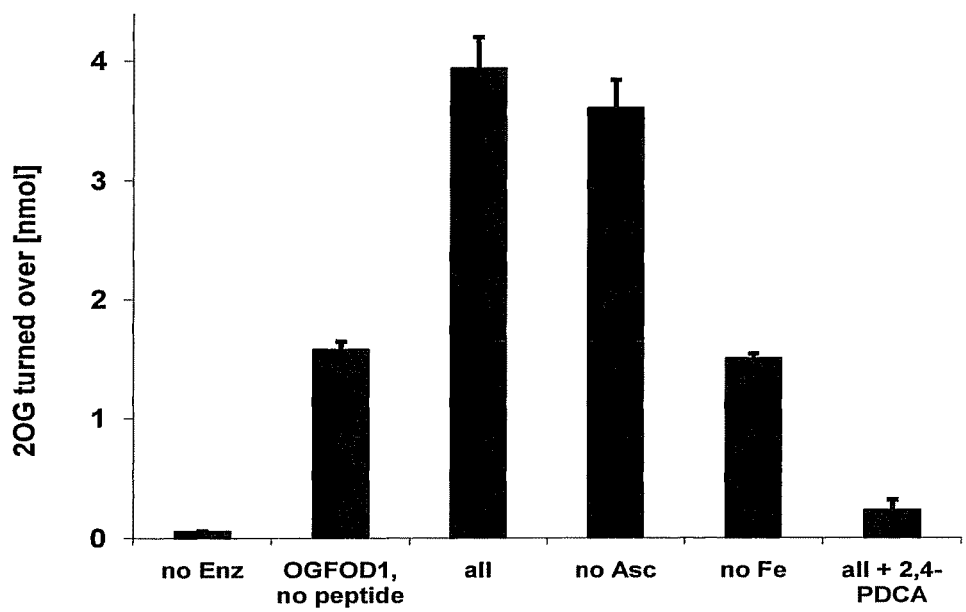

SEQUENCE LISTING

```
<160> NUMBER OF SEQ ID NOS: 39

<210> SEQ ID NO 1
<211> LENGTH: 542
<212> TYPE: PRT
<213> ORGANISM: Homo sapiens

<400> SEQUENCE: 1
```

```
Met Asn Gly Lys Arg Pro Ala Glu Pro Gly Pro Ala Arg Val Gly Lys
1               5                   10                  15

Lys Gly Lys Lys Glu Val Met Ala Glu Phe Ser Asp Ala Val Thr Glu
            20                  25                  30

Glu Thr Leu Lys Lys Gln Val Ala Glu Ala Trp Ser Arg Arg Thr Pro
        35                  40                  45

Phe Ser His Glu Val Ile Val Met Asp Met Asp Pro Phe Leu His Cys
    50                  55                  60

Val Ile Pro Asn Phe Ile Gln Ser Gln Asp Phe Leu Glu Gly Leu Gln
65                  70                  75                  80

Lys Glu Leu Met Asn Leu Asp Phe His Glu Lys Tyr Asn Asp Leu Tyr
                85                  90                  95

Lys Phe Gln Gln Ser Asp Asp Leu Lys Lys Arg Arg Glu Pro His Ile
            100                 105                 110

Ser Thr Leu Arg Lys Ile Leu Phe Glu Asp Phe Arg Ser Trp Leu Ser
        115                 120                 125

Asp Ile Ser Lys Ile Asp Leu Glu Ser Thr Ile Asp Met Ser Cys Ala
    130                 135                 140

Lys Tyr Glu Phe Thr Asp Ala Leu Leu Cys His Asp Asp Glu Leu Glu
145                 150                 155                 160

Gly Arg Arg Ile Ala Phe Ile Leu Tyr Leu Val Pro Pro Trp Asp Arg
                165                 170                 175

Ser Met Gly Gly Thr Leu Asp Leu Tyr Ser Ile Asp Glu His Phe Gln
            180                 185                 190

Pro Lys Gln Ile Val Lys Ser Leu Ile Pro Ser Trp Asn Lys Leu Val
        195                 200                 205

Phe Phe Glu Val Ser Pro Val Ser Phe His Gln Val Ser Glu Val Leu
    210                 215                 220

Ser Glu Glu Lys Ser Arg Leu Ser Ile Ser Gly Trp Phe His Gly Pro
225                 230                 235                 240

Ser Leu Thr Arg Pro Pro Asn Tyr Phe Glu Pro Ile Pro Arg Ser
                245                 250                 255

Pro His Ile Pro Gln Asp His Glu Ile Leu Tyr Asp Trp Ile Asn Pro
            260                 265                 270

Thr Tyr Leu Asp Met Asp Tyr Gln Val Gln Ile Gln Glu Glu Phe Glu
        275                 280                 285

Glu Ser Ser Glu Ile Leu Leu Lys Glu Phe Leu Lys Pro Glu Lys Phe
    290                 295                 300

Thr Lys Val Cys Glu Ala Leu Glu His Gly His Val Glu Trp Ser Ser
305                 310                 315                 320

Arg Gly Pro Pro Asn Lys Arg Phe Tyr Glu Lys Ala Glu Glu Ser Lys
                325                 330                 335

Leu Pro Glu Ile Leu Lys Glu Cys Met Lys Leu Phe Arg Ser Glu Ala
            340                 345                 350

Leu Phe Leu Leu Leu Ser Asn Phe Thr Gly Leu Lys Leu His Phe Leu
        355                 360                 365

Ala Pro Ser Glu Glu Asp Glu Met Asn Asp Lys Lys Glu Ala Glu Thr
    370                 375                 380

Thr Asp Ile Thr Glu Glu Gly Thr Ser His Ser Pro Pro Glu Pro Glu
385                 390                 395                 400

Asn Asn Gln Met Ala Ile Ser Asn Asn Ser Gln Gln Ser Asn Glu Gln
                405                 410                 415
```

Thr Asp Pro Glu Pro Glu Asn Glu Thr Lys Lys Glu Ser Ser Val
                420                 425                 430

Pro Met Cys Gln Gly Glu Leu Arg His Trp Lys Thr Gly His Tyr Thr
            435                 440                 445

Leu Ile His Asp His Ser Lys Ala Glu Phe Ala Leu Asp Leu Ile Leu
        450                 455                 460

Tyr Cys Gly Cys Glu Gly Trp Glu Pro Glu Tyr Gly Gly Phe Thr Ser
465                 470                 475                 480

Tyr Ile Ala Lys Gly Glu Asp Glu Glu Leu Thr Val Asn Pro Glu
                485                 490                 495

Ser Asn Ser Leu Ala Leu Val Tyr Arg Asp Arg Glu Thr Leu Lys Phe
            500                 505                 510

Val Lys His Ile Asn His Arg Ser Leu Glu Gln Lys Lys Thr Phe Pro
        515                 520                 525

Asn Arg Thr Gly Phe Trp Asp Phe Ser Phe Ile Tyr Tyr Glu
            530                 535                 540

<210> SEQ ID NO 2
<211> LENGTH: 542
<212> TYPE: PRT
<213> ORGANISM: Pongo pygmaeus

<400> SEQUENCE: 2

Met Asn Gly Lys Arg Pro Ala Glu Pro Gly Pro Ala Arg Val Gly Lys
1               5                   10                  15

Lys Arg Lys Lys Glu Val Met Ala Glu Phe Ser Asp Ala Val Thr Glu
            20                  25                  30

Glu Thr Leu Lys Lys Gln Val Ala Glu Ala Trp Ser Arg Arg Thr Pro
        35                  40                  45

Phe Ser His Glu Val Ile Val Met Asp Met Asp Pro Phe Leu His Cys
    50                  55                  60

Val Ile Pro Asn Phe Ile Gln Ser Gln Asp Phe Leu Glu Gly Leu Gln
65                  70                  75                  80

Lys Glu Leu Met Asn Leu Asp Phe His Glu Lys Tyr Asn Asp Leu Tyr
                85                  90                  95

Lys Phe Gln Gln Ser Asp Asp Leu Lys Lys Arg Arg Glu Pro His Ile
            100                 105                 110

Ser Ala Leu Arg Lys Ile Leu Phe Glu Asp Phe Arg Ser Trp Leu Ser
        115                 120                 125

Asp Ile Ser Lys Ile Asp Leu Glu Ser Thr Ile Asp Met Ser Cys Ala
    130                 135                 140

Lys Tyr Glu Phe Thr Asp Ala Leu Leu Cys His Asp Asp Glu Leu Glu
145                 150                 155                 160

Gly Arg Arg Ile Ala Phe Ile Leu Tyr Leu Val Pro Pro Trp Asp Arg
                165                 170                 175

Ser Leu Gly Gly Thr Leu Asp Leu Tyr Ser Ile Asp Glu His Phe Gln
            180                 185                 190

Pro Lys Gln Ile Val Lys Ser Leu Ile Pro Ser Trp Asn Lys Leu Val
        195                 200                 205

Phe Phe Glu Val Ser Pro Val Ser Phe His Gln Val Ser Glu Val Leu
    210                 215                 220

Ser Glu Glu Lys Ser Arg Leu Ser Ile Ser Gly Trp Phe His Gly Pro
225                 230                 235                 240

Ser Leu Thr Arg Pro Pro Asn His Phe Glu Pro Pro Ile Pro Arg Ser
                245                 250                 255

```
Pro His Ile Pro Gln Asp His Glu Ile Leu Tyr Asp Trp Ile Asn Pro
            260                 265                 270

Thr Tyr Leu Asp Met Asp Tyr Gln Val Gln Ile Gln Glu Glu Phe Glu
        275                 280                 285

Glu Ser Ser Glu Ile Leu Leu Lys Glu Phe Leu Lys Pro Glu Lys Phe
    290                 295                 300

Met Lys Val Cys Glu Ala Leu Glu His Gly Asp Val Glu Trp Ser Ser
305                 310                 315                 320

Arg Gly Pro Pro Asn Lys Arg Phe Tyr Glu Lys Ala Glu Gly Ser Lys
                325                 330                 335

Leu Pro Glu Ile Leu Lys Glu Cys Met Lys Leu Phe His Ser Glu Ala
            340                 345                 350

Leu Phe Leu Leu Leu Ser Asn Phe Thr Gly Leu Lys Leu His Phe Leu
        355                 360                 365

Ala Pro Ser Glu Glu Asp Glu Met Asn Asp Lys Lys Glu Ala Glu Ala
    370                 375                 380

Ala Asp Ile Thr Glu Glu Gly Thr Ser His Ser Pro Pro Glu Pro Glu
385                 390                 395                 400

Asn Asn Gln Thr Ala Ile Ser Asn Asn Ser Gln Gln Ser Asn Glu Gln
                405                 410                 415

Thr Asp Pro Glu Pro Glu Glu Asn Glu Thr Lys Lys Glu Ser Ser Val
            420                 425                 430

Pro Thr Cys Gln Gly Glu Leu Arg Arg Trp Lys Thr Gly His Tyr Thr
        435                 440                 445

Leu Ile His Asp His Ser Lys Ala Glu Phe Ala Leu Asp Leu Ile Leu
    450                 455                 460

Tyr Cys Gly Cys Glu Gly Trp Glu Pro Glu Tyr Gly Gly Phe Thr Ser
465                 470                 475                 480

Tyr Ile Ala Lys Gly Glu Asp Glu Glu Leu Leu Thr Val Asn Pro Glu
                485                 490                 495

Ser Asn Ser Leu Ala Leu Val Tyr Arg Asp Arg Glu Thr Leu Lys Phe
            500                 505                 510

Val Lys His Ile Asn His Arg Ser Leu Glu Gln Lys Lys Thr Phe Pro
        515                 520                 525

Asn Arg Thr Gly Phe Trp Asp Phe Ser Phe Ile Tyr Tyr Glu
    530                 535                 540

<210> SEQ ID NO 3
<211> LENGTH: 542
<212> TYPE: PRT
<213> ORGANISM: Bos taurus

<400> SEQUENCE: 3

Met Asn Gly Lys Arg Pro Ala Glu Pro Gly Ser Asp Arg Ala Gly Lys
1               5                   10                  15

Lys Val Lys Lys Glu Val Met Ala Lys Phe Ser Asp Ala Val Thr Glu
            20                  25                  30

Glu Thr Leu Lys Lys Gln Val Ala Glu Ala Trp Ser Arg Arg Thr Pro
        35                  40                  45

Phe Arg His Glu Ala Ile Val Met Asp Met Asp Pro Phe Leu His Cys
    50                  55                  60

Val Ile Pro Asn Phe Ile Gln Ser Gln Asn Phe Leu Glu Gly Leu Gln
65              70                  75                  80

Lys Glu Leu Leu Asn Leu Asp Phe His Glu Lys Tyr Asn Asp Leu Tyr
```

```
            85                  90                  95
Lys Phe Gln Gln Ser Asp Asp Leu Lys Lys Arg Arg Glu Pro His Ile
            100                 105                 110
Cys Ala Leu Arg Lys Ile Leu Phe Glu His Phe Arg Ser Trp Ile Ser
            115                 120                 125
Asp Ile Ser Lys Ile Asp Leu Glu Ser Thr Ile Asp Met Ser Cys Ala
            130                 135                 140
Lys Tyr Glu Phe Ser Asp Ala Leu Leu Cys His Asp Asp Glu Leu Glu
145                 150                 155                 160
Gly Arg Arg Ile Ala Phe Ile Leu Tyr Leu Val Pro Pro Trp Asp Ala
                    165                 170                 175
Ser Leu Gly Gly Thr Leu Asp Leu Phe Ser Val Asp Glu His Phe Gln
                    180                 185                 190
Pro Lys Gln Ile Val Lys Ser Leu Ile Pro Ser Trp Asn Thr Leu Val
                    195                 200                 205
Phe Phe Glu Val Ser Pro Val Ser Phe His Gln Val Ser Glu Val Leu
            210                 215                 220
Ser Glu Glu Lys Ser Arg Leu Ser Ile Ser Gly Trp Phe His Gly Pro
225                 230                 235                 240
Ser Leu Thr Arg Pro Pro Thr Tyr Phe Glu Pro Leu Ile Ala Arg Ser
                    245                 250                 255
Pro His Ile Pro Gln Asp His Glu Ile Leu Tyr Asp Trp Ile Asn Pro
                    260                 265                 270
Thr Tyr Leu Asp Met Glu Tyr Gln Ala Gln Ile Gln Glu Glu Phe Glu
            275                 280                 285
Glu Ser Ser Glu Ile Leu Leu Lys Glu Phe Leu Gln Pro Glu Lys Phe
            290                 295                 300
Ala Glu Val Cys Glu Ala Leu Glu Arg Gly Arg Val Glu Trp Ser Ser
305                 310                 315                 320
Arg Gly Pro Pro Asn Lys Arg Phe Tyr Glu Lys Ala Glu Glu Ser Gln
                    325                 330                 335
Leu Pro Asp Ile Leu Arg Asp Cys Met Ala Leu Phe Arg Ser Glu Ala
            340                 345                 350
Met Phe Leu Leu Leu Ser Asn Phe Thr Gly Leu Lys Leu His Phe Leu
            355                 360                 365
Ala Pro Ser Glu Asp Glu Pro Glu Asp Lys Lys Glu Arg Asp Ala Val
            370                 375                 380
Ser Ala Ala Glu Asn Thr Glu Glu Gly Thr Ser His Ser Ser Ser Glu
385                 390                 395                 400
Pro Glu Asn Ser Trp Ala Ala Thr Ser Asp Ser Ser Leu Gln Ser Glu
                    405                 410                 415
Gly Pro Thr Asp Pro Glu Glu Asp Glu Ala Lys Lys Glu Ser Ser Val
                    420                 425                 430
Pro Thr Cys Gln Gly Glu Leu Arg His Trp Lys Thr Gly His Tyr Thr
                    435                 440                 445
Leu Ile His Asp Asn Ser Lys Thr Glu Phe Ala Leu Asp Leu Leu Leu
            450                 455                 460
Tyr Cys Gly Cys Glu Gly Trp Glu Pro Glu Tyr Gly Gly Phe Thr Ser
465                 470                 475                 480
Tyr Ile Ala Lys Gly Glu Asp Glu Glu Leu Leu Thr Val Asn Pro Glu
                    485                 490                 495
Asn Asn Ser Leu Ala Leu Val Tyr Arg Asp Arg Glu Thr Leu Lys Phe
            500                 505                 510
```

Val Lys His Ile Asn His Arg Ser Leu Glu Gln Lys Lys Ser Phe Pro
                515                 520                 525

Asn Arg Thr Gly Phe Trp Asp Phe Ser Phe Val Tyr Tyr Glu
            530                 535                 540

<210> SEQ ID NO 4
<211> LENGTH: 545
<212> TYPE: PRT
<213> ORGANISM: Rattus norvegicus

<400> SEQUENCE: 4

Met Asn Gly Lys Arg Pro Ala Asp Pro Gly Pro Ala Arg Pro Met Lys
1               5                   10                  15

Lys Gly Lys Lys Gln Val Ala Ala Glu Phe Ser Asp Ala Val Thr Glu
                20                  25                  30

Glu Ile Leu Arg Lys Gln Val Ala Glu Ala Trp Ser Cys Arg Thr Pro
            35                  40                  45

Phe Ser His Glu Ala Ile Ala Leu Asp Met Asp Pro Phe Leu His Cys
        50                  55                  60

Val Ile Pro Asn Phe Ile Gln Ser Gln Asp Phe Leu Glu Gly Leu Gln
65                  70                  75                  80

Lys Glu Leu Leu Ser Leu Asp Phe His Glu Lys Tyr Asn Asp Leu Tyr
                85                  90                  95

Lys Phe Gln Gln Ser Asp Asp Leu Lys Lys Arg Lys Glu Pro His Ile
            100                 105                 110

Ser Ala Leu Arg Thr Leu Met Phe Glu Asp Phe Arg Ala Trp Leu Ser
        115                 120                 125

Lys Val Ser Gly Ile Asp Leu Glu Ala Thr Val Asp Met Ser Cys Ala
130                 135                 140

Lys Tyr Glu Phe Thr Asp Ala Leu Leu Cys His Asp Asp Glu Leu Glu
145                 150                 155                 160

Gly Arg Arg Ile Ala Phe Ile Leu Tyr Leu Val Pro Ser Trp Asp Arg
                165                 170                 175

Asp Leu Gly Gly Thr Leu Asp Leu Tyr Asp Thr Asp Glu His Leu Gln
            180                 185                 190

Pro Lys Gln Ile Val Lys Ser Leu Val Pro Ala Trp Asn Lys Leu Val
        195                 200                 205

Phe Phe Glu Val Ser Pro Val Ser Phe His Gln Val Ser Glu Val Leu
210                 215                 220

Ser Glu Glu Leu Thr Arg Leu Ser Ile Ser Gly Trp Phe His Gly Pro
225                 230                 235                 240

Ser Leu Ala Arg Pro Pro Thr Tyr Phe Glu Pro Pro Val Pro Arg Ser
                245                 250                 255

Pro His Ile Pro Gln Asp His Glu Ile Leu Tyr Glu Trp Ile Asn Pro
            260                 265                 270

Ala Tyr Leu Glu Met Asp Tyr Gln Met Gln Ile Gln Glu Glu Phe Glu
        275                 280                 285

Glu Arg Ser Glu Ile Leu Leu Lys Glu Phe Leu Lys Pro Glu Lys Phe
290                 295                 300

Ala Lys Val Cys Glu Ala Leu Glu Lys Gly Asp Val Glu Trp Lys Ser
305                 310                 315                 320

His Gly Pro Pro Asn Lys Arg Phe Tyr Glu Lys Ala Lys Glu Ser Asn
                325                 330                 335

Leu Pro Asp Val Leu Lys Glu Cys Met Gly Leu Phe His Ser Glu Ala

```
                340             345             350
Met Phe Leu Leu Leu Ser Asn Phe Thr Gly Leu Lys Leu His Phe Leu
            355                 360                 365

Ala Pro Ser Glu Asp Glu Thr Glu Asp Lys Gly Glu Gly Glu Thr
370                 375                 380

Ala Ser Ala Ala Gly Gly Thr Glu Glu Gly Thr Ser Gln Ser Pro Pro
385                 390                 395                 400

Gly Pro Glu Asp Asn Gln Ala Ala Val Gly Ser His Ser Gln Glu Asn
            405                 410                 415

Gly Glu Gln Ala Asp Pro Glu Pro Gln Glu Asp Glu Ala Lys Lys Glu
            420                 425                 430

Ser Ser Val Pro Met Cys Gln Gly Glu Leu Arg Arg Trp Lys Thr Gly
            435                 440                 445

His Tyr Thr Leu Val His Asp Asn Ser Lys Thr Glu Phe Ala Leu Asp
            450                 455                 460

Leu Phe Leu Tyr Cys Gly Cys Glu Gly Trp Glu Pro Glu Tyr Gly Gly
465                 470                 475                 480

Phe Thr Ser Tyr Ile Ala Lys Gly Glu Asp Glu Leu Leu Ile Val
                485                 490                 495

Asn Pro Glu Asn Asn Ala Leu Ala Leu Val Tyr Arg Asp Arg Glu Thr
            500                 505                 510

Leu Arg Phe Val Lys His Ile Asn His Arg Ser Leu Glu Gln Arg Asn
            515                 520                 525

Thr Phe Pro Asn Arg Ser Gly Phe Trp Asp Phe Ala Phe Met Tyr Tyr
            530                 535                 540

Glu
545

<210> SEQ ID NO 5
<211> LENGTH: 488
<212> TYPE: PRT
<213> ORGANISM: Mus musculus

<400> SEQUENCE: 5

Met Lys Lys Gly Lys Lys Gln Val Ser Ala Glu Phe Ser Asp Ala Val
1               5                   10                  15

Thr Glu Glu Ile Leu Arg Lys Gln Val Ala Glu Ala Trp Ser Cys Arg
            20                  25                  30

Thr Pro Phe Ser His Glu Ala Ile Ala Leu Asp Met Asp Pro Phe Leu
        35                  40                  45

His Cys Val Ile Pro Asn Phe Ile Gln Ser Gln Asp Phe Leu Glu Gly
    50                  55                  60

Leu His Lys Glu Leu Leu Ser Leu Asp Phe His Glu Lys Tyr Asn Asp
65                  70                  75                  80

Leu Tyr Lys Phe Gln Gln Ser Asp Asp Leu Lys Asn Arg Lys Glu Pro
                85                  90                  95

His Ile Ser Ala Leu Arg Lys Leu Met Phe Glu Asp Phe Arg Ala Trp
            100                 105                 110

Leu Ser Lys Val Ser Gly Ile Asp Leu Glu Pro Thr Ile Asp Met Ser
        115                 120                 125

Cys Ala Lys Tyr Glu Phe Thr Asp Ala Leu Leu Cys His Asp Asp Glu
    130                 135                 140

Leu Glu Gly Arg Arg Ile Ala Phe Ile Leu Tyr Leu Val Pro Ser Trp
145                 150                 155                 160
```

```
Asp Arg Asp Leu Gly Gly Thr Leu Asp Leu Tyr Asp Thr Asp Glu His
            165                 170                 175
Leu Gln Pro Lys Gln Ile Val Lys Ser Leu Ile Pro Ser Trp Asn Lys
        180                 185                 190
Leu Val Phe Phe Glu Val Ser Pro Val Ser Phe His Gln His Glu Ile
    195                 200                 205
Leu Tyr Glu Trp Ile Asn Pro Ala Tyr Leu Glu Met Asp Tyr Gln Met
210                 215                 220
Gln Ile Gln Glu Glu Phe Glu Glu Arg Ser Glu Ile Leu Leu Lys Glu
225                 230                 235                 240
Phe Leu Lys Pro Glu Lys Phe Ala Glu Val Cys Glu Ala Leu Glu Lys
                245                 250                 255
Gly Asp Val Glu Trp Lys Ser His Gly Pro Pro Asn Lys Arg Phe Tyr
            260                 265                 270
Glu Lys Ala Glu Glu Asn Asn Leu Pro Asp Val Leu Lys Glu Cys Met
        275                 280                 285
Gly Leu Phe Arg Ser Glu Ala Leu Phe Leu Leu Ser Asn Leu Thr
    290                 295                 300
Gly Leu Lys Leu His Phe Leu Ala Pro Ser Glu Asp Glu Thr Glu
305                 310                 315                 320
Glu Lys Gly Glu Gly Glu Thr Ala Ser Ala Ala Gly Thr Glu Glu
                325                 330                 335
Gly Thr Ser Arg Arg Pro Ser Gly Pro Glu Asn Asn Gln Val Ala Ala
            340                 345                 350
Gly Ser His Ser Gln Glu Asn Gly Glu Gln Ala Asp Pro Glu Ala Gln
        355                 360                 365
Glu Glu Glu Ala Lys Lys Glu Ser Ser Val Pro Met Cys Gln Gly Glu
370                 375                 380
Leu Arg Arg Trp Lys Thr Gly His Tyr Thr Leu Val His Asp Asn Thr
385                 390                 395                 400
Lys Thr Glu Phe Ala Leu Asp Leu Phe Leu Tyr Cys Gly Cys Glu Gly
                405                 410                 415
Trp Glu Pro Glu Tyr Gly Gly Phe Thr Ser Tyr Ile Ala Lys Gly Glu
            420                 425                 430
Asp Glu Glu Leu Leu Ile Val Asn Pro Glu Asn Asn Ser Leu Ala Leu
        435                 440                 445
Val Tyr Arg Asp Arg Glu Thr Leu Arg Phe Val Lys His Ile Asn His
    450                 455                 460
Arg Ser Leu Glu Gln Ser Lys Ala Phe Pro Ser Arg Ser Gly Phe Trp
465                 470                 475                 480
Asp Phe Ala Phe Ile Tyr Tyr Glu
                485

<210> SEQ ID NO 6
<211> LENGTH: 143
<212> TYPE: PRT
<213> ORGANISM: Homo sapiens

<400> SEQUENCE: 6

Met Gly Lys Cys Arg Gly Leu Arg Thr Ala Arg Lys Leu Arg Ser His
1               5                   10                  15
Arg Arg Asp Gln Lys Trp His Asp Lys Gln Tyr Lys Lys Ala His Leu
            20                  25                  30
Gly Thr Ala Leu Lys Ala Asn Pro Phe Gly Gly Ala Ser His Ala Lys
        35                  40                  45
```

```
Gly Ile Val Leu Glu Lys Val Gly Val Glu Ala Lys Gln Pro Asn Ser
    50                  55                  60

Ala Ile Arg Lys Cys Val Arg Val Gln Leu Ile Lys Asn Gly Lys Lys
65                  70                  75                  80

Ile Thr Ala Phe Val Pro Asn Asp Gly Cys Leu Asn Phe Ile Glu Glu
                    85                  90                  95

Asn Asp Glu Val Leu Val Ala Gly Phe Gly Arg Lys Gly His Ala Val
                100                 105                 110

Gly Asp Ile Pro Gly Val Arg Phe Lys Val Val Lys Val Ala Asn Val
                115                 120                 125

Ser Leu Leu Ala Leu Tyr Lys Gly Lys Lys Glu Arg Pro Arg Ser
    130                 135                 140
```

<210> SEQ ID NO 7
<211> LENGTH: 292
<212> TYPE: PRT
<213> ORGANISM: Artificial sequence
<220> FEATURE:
<223> OTHER INFORMATION: C-terminal domain of OGFOD1 cloned into pET21d

<400> SEQUENCE: 7

```
Met Ala Gln Asp His Glu Ile Leu Tyr Asp Trp Ile Asn Pro Thr Tyr
1               5                   10                  15

Leu Asp Met Asp Tyr Gln Val Gln Ile Gln Glu Glu Phe Glu Glu Ser
                20                  25                  30

Ser Glu Ile Leu Leu Lys Glu Phe Leu Lys Pro Glu Lys Phe Thr Lys
            35                  40                  45

Val Cys Glu Ala Leu Glu His Gly His Val Glu Trp Ser Ser Arg Gly
    50                  55                  60

Pro Pro Asn Lys Arg Phe Tyr Glu Lys Ala Glu Ser Lys Leu Pro
65                  70                  75                  80

Glu Ile Leu Lys Glu Cys Met Lys Leu Phe Arg Ser Glu Ala Leu Phe
                85                  90                  95

Leu Leu Leu Ser Asn Phe Thr Gly Leu Lys Leu His Phe Leu Ala Pro
                100                 105                 110

Ser Glu Glu Asp Glu Met Asn Asp Lys Lys Glu Ala Glu Thr Thr Asp
                115                 120                 125

Ile Thr Glu Glu Gly Thr Ser His Ser Pro Pro Glu Pro Glu Asn Asn
    130                 135                 140

Gln Met Ala Ile Ser Asn Asn Ser Gln Ser Asn Glu Gln Thr Asp
145                 150                 155                 160

Pro Glu Pro Glu Glu Asn Glu Thr Lys Lys Glu Ser Ser Val Pro Met
                165                 170                 175

Cys Gln Gly Glu Leu Arg His Trp Lys Thr Gly His Tyr Thr Leu Ile
                180                 185                 190

His Asp His Ser Lys Ala Glu Phe Ala Leu Asp Leu Ile Leu Tyr Cys
                195                 200                 205

Gly Cys Glu Gly Trp Glu Pro Glu Tyr Gly Gly Phe Thr Ser Tyr Ile
    210                 215                 220

Ala Lys Gly Glu Asp Glu Glu Leu Leu Thr Val Asn Pro Glu Ser Asn
225                 230                 235                 240

Ser Leu Ala Leu Val Tyr Arg Asp Arg Glu Thr Leu Lys Phe Val Lys
                245                 250                 255

His Ile Asn His Arg Ser Leu Glu Gln Lys Lys Thr Phe Pro Asn Arg
                260                 265                 270
```

```
Thr Gly Phe Trp Asp Phe Ser Phe Ile Tyr Tyr Glu Leu Glu His His
        275                 280                 285
His His His His
    290
```

<210> SEQ ID NO 8
<211> LENGTH: 27
<212> TYPE: DNA
<213> ORGANISM: Artificial sequence
<220> FEATURE:
<223> OTHER INFORMATION: Forward primer for OGFOD1_Q261

<400> SEQUENCE: 8
ataccatggc tcaagatcat gagattt                                        27

<210> SEQ ID NO 9
<211> LENGTH: 29
<212> TYPE: DNA
<213> ORGANISM: Artificial sequence
<220> FEATURE:
<223> OTHER INFORMATION: Reverse primer for OGFOD1_Q261

<400> SEQUENCE: 9
aaactcgagt tcataataga tgaatgaaa                                      29

<210> SEQ ID NO 10
<211> LENGTH: 565
<212> TYPE: PRT
<213> ORGANISM: Artificial sequence
<220> FEATURE:
<223> OTHER INFORMATION: Full-length human OGFOD1-H155A mutant clone
      into pET28

<400> SEQUENCE: 10

```
Met Gly Ser Ser His His His His His His Ser Ser Gly Leu Val Pro
1               5                  10                  15

Arg Gly Ser His Met Ala Ser Met Asn Gly Lys Arg Pro Ala Glu Pro
            20                  25                  30

Gly Pro Ala Arg Val Gly Lys Lys Gly Lys Lys Glu Val Met Ala Glu
        35                  40                  45

Phe Ser Asp Ala Val Thr Glu Thr Leu Lys Lys Gln Val Ala Glu
    50                  55                  60

Ala Trp Ser Arg Arg Thr Pro Phe Ser His Glu Val Ile Val Met Asp
65                  70                  75                  80

Met Asp Pro Phe Leu His Cys Val Ile Pro Asn Phe Ile Gln Ser Gln
                85                  90                  95

Asp Phe Leu Glu Gly Leu Gln Lys Glu Leu Met Asn Leu Asp Phe His
            100                 105                 110

Glu Lys Tyr Asn Asp Leu Tyr Lys Phe Gln Gln Ser Asp Asp Leu Lys
        115                 120                 125

Lys Arg Arg Glu Pro His Ile Ser Thr Leu Arg Lys Ile Leu Phe Glu
    130                 135                 140

Asp Phe Arg Ser Trp Leu Ser Asp Ile Ser Lys Ile Asp Leu Glu Ser
145                 150                 155                 160

Thr Ile Asp Met Ser Cys Ala Lys Tyr Glu Phe Thr Asp Ala Leu Leu
                165                 170                 175

Cys Ala Asp Asp Glu Leu Glu Gly Arg Arg Ile Ala Phe Ile Leu Tyr
            180                 185                 190

Leu Val Pro Pro Trp Asp Arg Ser Met Gly Gly Thr Leu Asp Leu Tyr
```

```
                195                 200                 205
Ser Ile Asp Glu His Phe Gln Pro Lys Gln Ile Val Lys Ser Leu Ile
210                 215                 220

Pro Ser Trp Asn Lys Leu Val Phe Glu Val Ser Pro Val Ser Phe
225                 230                 235                 240

His Gln Val Ser Glu Val Leu Ser Glu Glu Lys Ser Arg Leu Ser Ile
                    245                 250                 255

Ser Gly Trp Phe His Gly Pro Ser Leu Thr Arg Pro Asn Tyr Phe
                260                 265                 270

Glu Pro Pro Ile Pro Arg Ser Pro His Ile Pro Gln Asp His Glu Ile
            275                 280                 285

Leu Tyr Asp Trp Ile Asn Pro Thr Tyr Leu Asp Met Asp Tyr Gln Val
290                 295                 300

Gln Ile Gln Glu Glu Phe Glu Glu Ser Ser Glu Ile Leu Leu Lys Glu
305                 310                 315                 320

Phe Leu Lys Pro Glu Lys Phe Thr Lys Val Cys Glu Ala Leu Glu His
                325                 330                 335

Gly His Val Glu Trp Ser Ser Arg Gly Pro Pro Asn Lys Arg Phe Tyr
                340                 345                 350

Glu Lys Ala Glu Glu Ser Lys Leu Pro Glu Ile Leu Lys Glu Cys Met
            355                 360                 365

Lys Leu Phe Arg Ser Glu Ala Leu Phe Leu Leu Ser Asn Phe Thr
370                 375                 380

Gly Leu Lys Leu His Phe Leu Ala Pro Ser Glu Glu Asp Glu Met Asn
385                 390                 395                 400

Asp Lys Lys Glu Ala Glu Thr Thr Asp Ile Thr Glu Gly Thr Ser
                405                 410                 415

His Ser Pro Pro Glu Pro Glu Asn Asn Gln Met Ala Ile Ser Asn Asn
                420                 425                 430

Ser Gln Gln Ser Asn Glu Gln Thr Asp Pro Glu Pro Glu Glu Asn Glu
            435                 440                 445

Thr Lys Lys Glu Ser Ser Val Pro Met Cys Gln Gly Glu Leu Arg His
450                 455                 460

Trp Lys Thr Gly His Tyr Thr Leu Ile His Asp His Ser Lys Ala Glu
465                 470                 475                 480

Phe Ala Leu Asp Leu Ile Leu Tyr Cys Gly Cys Glu Gly Trp Glu Pro
                485                 490                 495

Glu Tyr Gly Gly Phe Thr Ser Tyr Ile Ala Lys Gly Glu Asp Glu Glu
                500                 505                 510

Leu Leu Thr Val Asn Pro Glu Ser Asn Ser Leu Ala Leu Val Tyr Arg
            515                 520                 525

Asp Arg Glu Thr Leu Lys Phe Val Lys His Ile Asn His Arg Ser Leu
530                 535                 540

Glu Gln Lys Lys Thr Phe Pro Asn Arg Thr Gly Phe Trp Asp Phe Ser
545                 550                 555                 560

Phe Ile Tyr Tyr Glu
                565

<210> SEQ ID NO 11
<211> LENGTH: 37
<212> TYPE: DNA
<213> ORGANISM: Artificial sequence
<220> FEATURE:
<223> OTHER INFORMATION: Forward primer for OGFOD1_H155A
```

<400> SEQUENCE: 11
ctgatgccct gctgtgcgcg gatgatgagc tggaagg 37

<210> SEQ ID NO 12
<211> LENGTH: 37
<212> TYPE: DNA
<213> ORGANISM: Artificial sequence
<220> FEATURE:
<223> OTHER INFORMATION: Reverse primer for OGFOD1-H155A

<400> SEQUENCE: 12
ccttccagct catcatccgc gcacagcagg gcatcag 37

<210> SEQ ID NO 13
<211> LENGTH: 565
<212> TYPE: PRT
<213> ORGANISM: Artificial sequence
<220> FEATURE:
<223> OTHER INFORMATION: Full-length human OGFOD1_D157A mutant cloned
      into pET28

<400> SEQUENCE: 13

```
Met Gly Ser Ser His His His His His His Ser Ser Gly Leu Val Pro
1               5                   10                  15

Arg Gly Ser His Met Ala Ser Met Asn Gly Lys Arg Pro Ala Glu Pro
                20                  25                  30

Gly Pro Ala Arg Val Gly Lys Gly Lys Lys Glu Val Met Ala Glu
            35                  40                  45

Phe Ser Asp Ala Val Thr Glu Glu Thr Leu Lys Lys Gln Val Ala Glu
50                  55                  60

Ala Trp Ser Arg Arg Thr Pro Phe Ser His Glu Val Ile Val Met Asp
65                  70                  75                  80

Met Asp Pro Phe Leu His Cys Val Ile Pro Asn Phe Ile Gln Ser Gln
                85                  90                  95

Asp Phe Leu Glu Gly Leu Gln Lys Glu Leu Met Asn Leu Asp Phe His
            100                 105                 110

Glu Lys Tyr Asn Asp Leu Tyr Lys Phe Gln Gln Ser Asp Asp Leu Lys
        115                 120                 125

Lys Arg Arg Glu Pro His Ile Ser Thr Leu Arg Lys Ile Leu Phe Glu
130                 135                 140

Asp Phe Arg Ser Trp Leu Ser Asp Ile Ser Lys Ile Asp Leu Glu Ser
145                 150                 155                 160

Thr Ile Asp Met Ser Cys Ala Lys Tyr Glu Phe Thr Asp Ala Leu Leu
                165                 170                 175

Cys Ala Asp Ala Glu Leu Glu Gly Arg Arg Ile Ala Phe Ile Leu Tyr
            180                 185                 190

Leu Val Pro Pro Trp Asp Arg Ser Met Gly Gly Thr Leu Asp Leu Tyr
        195                 200                 205

Ser Ile Asp Glu His Phe Gln Pro Lys Gln Ile Val Lys Ser Leu Ile
    210                 215                 220

Pro Ser Trp Asn Lys Leu Val Phe Glu Val Ser Pro Val Ser Phe
225                 230                 235                 240

His Gln Val Ser Glu Val Leu Ser Glu Lys Ser Arg Leu Ser Ile
                245                 250                 255

Ser Gly Trp Phe His Gly Pro Ser Leu Thr Arg Pro Pro Asn Tyr Phe
            260                 265                 270

Glu Pro Pro Ile Pro Arg Ser Pro His Ile Pro Gln Asp His Glu Ile
```

```
                275                 280                 285
Leu Tyr Asp Trp Ile Asn Pro Thr Tyr Leu Asp Met Asp Tyr Gln Val
    290                 295                 300

Gln Ile Gln Glu Glu Phe Glu Glu Ser Ser Glu Ile Leu Leu Lys Glu
305                 310                 315                 320

Phe Leu Lys Pro Glu Lys Phe Thr Lys Val Cys Glu Ala Leu Glu His
                325                 330                 335

Gly His Val Glu Trp Ser Ser Arg Gly Pro Pro Asn Lys Arg Phe Tyr
            340                 345                 350

Glu Lys Ala Glu Glu Ser Lys Leu Pro Glu Ile Leu Lys Glu Cys Met
        355                 360                 365

Lys Leu Phe Arg Ser Glu Ala Leu Phe Leu Leu Leu Ser Asn Phe Thr
    370                 375                 380

Gly Leu Lys Leu His Phe Leu Ala Pro Ser Glu Glu Asp Glu Met Asn
385                 390                 395                 400

Asp Lys Lys Glu Ala Glu Thr Thr Asp Ile Thr Glu Glu Gly Thr Ser
                405                 410                 415

His Ser Pro Pro Glu Pro Glu Asn Asn Gln Met Ala Ile Ser Asn Asn
            420                 425                 430

Ser Gln Gln Ser Asn Glu Gln Thr Asp Pro Glu Pro Glu Glu Asn Glu
        435                 440                 445

Thr Lys Lys Glu Ser Ser Val Pro Met Cys Gln Gly Glu Leu Arg His
    450                 455                 460

Trp Lys Thr Gly His Tyr Thr Leu Ile His Asp His Ser Lys Ala Glu
465                 470                 475                 480

Phe Ala Leu Asp Leu Ile Leu Tyr Cys Gly Cys Gly Gly Trp Glu Pro
                485                 490                 495

Glu Tyr Gly Gly Phe Thr Ser Tyr Ile Ala Lys Gly Glu Asp Glu Glu
            500                 505                 510

Leu Leu Thr Val Asn Pro Glu Ser Asn Ser Leu Ala Leu Val Tyr Arg
        515                 520                 525

Asp Arg Glu Thr Leu Lys Phe Val Lys His Ile Asn His Arg Ser Leu
    530                 535                 540

Glu Gln Lys Lys Thr Phe Pro Asn Arg Thr Gly Phe Trp Asp Phe Ser
545                 550                 555                 560

Phe Ile Tyr Tyr Glu
            565

<210> SEQ ID NO 14
<211> LENGTH: 32
<212> TYPE: DNA
<213> ORGANISM: Artificial sequence
<220> FEATURE:
<223> OTHER INFORMATION: Forward primer for OGFOD1_D157A

<400> SEQUENCE: 14
tgctgtgcca tgatgcggag ctggaagggc gc                                    32

<210> SEQ ID NO 15
<211> LENGTH: 32
<212> TYPE: DNA
<213> ORGANISM: Artificial sequence
<220> FEATURE:
<223> OTHER INFORMATION: Reverse primer for OGFOD1_D157A

<400> SEQUENCE: 15
gcgcccttcc agctccgcat catggcacag ca                                    32
```

<210> SEQ ID NO 16
<211> LENGTH: 20
<212> TYPE: PRT
<213> ORGANISM: Homo sapiens

<400> SEQUENCE: 16

Val Leu Glu Lys Val Gly Val Glu Ala Lys Gln Pro Asn Ser Ala Ile
1               5                   10                  15

Arg Lys Cys Val
            20

<210> SEQ ID NO 17
<211> LENGTH: 16
<212> TYPE: PRT
<213> ORGANISM: Homo sapiens

<400> SEQUENCE: 17

Glu Lys Val Gly Val Glu Ala Lys Gln Pro Asn Ser Ala Ile Arg Lys
1               5                   10                  15

<210> SEQ ID NO 18
<211> LENGTH: 20
<212> TYPE: PRT
<213> ORGANISM: Schizosaccharomyces pombe

<400> SEQUENCE: 18

Val Val Glu Lys Ile Gly Val Glu Ala Lys Gln Pro Asn Ser Ala Ile
1               5                   10                  15

Arg Lys Cys Val
            20

<210> SEQ ID NO 19
<211> LENGTH: 20
<212> TYPE: PRT
<213> ORGANISM: Saccharomyces cerevisiae

<400> SEQUENCE: 19

Val Leu Glu Lys Leu Gly Ile Glu Ser Lys Gln Pro Asn Ser Ala Ile
1               5                   10                  15

Arg Lys Cys Val
            20

<210> SEQ ID NO 20
<211> LENGTH: 20
<212> TYPE: PRT
<213> ORGANISM: Escherichia coli

<400> SEQUENCE: 20

Cys Thr Arg Val Tyr Thr Thr Thr Pro Lys Lys Pro Asn Ser Ala Leu
1               5                   10                  15

Arg Lys Val Cys
            20

<210> SEQ ID NO 21
<211> LENGTH: 20
<212> TYPE: PRT
<213> ORGANISM: Artificial sequence
<220> FEATURE:
<223> OTHER INFORMATION: Synthesized RPS23_K04A

<400> SEQUENCE: 21

Val Leu Glu Ala Val Gly Val Glu Ala Lys Gln Pro Asn Ser Ala Ile

```
1               5                   10                  15

Arg Lys Cys Val
            20

<210> SEQ ID NO 22
<211> LENGTH: 20
<212> TYPE: PRT
<213> ORGANISM: Artificial sequence
<220> FEATURE:
<223> OTHER INFORMATION: Synthesized RPS23_V05A

<400> SEQUENCE: 22

Val Leu Glu Lys Ala Gly Val Glu Ala Lys Gln Pro Asn Ser Ala Ile
1               5                   10                  15

Arg Lys Cys Val
            20

<210> SEQ ID NO 23
<211> LENGTH: 20
<212> TYPE: PRT
<213> ORGANISM: Artificial sequence
<220> FEATURE:
<223> OTHER INFORMATION: Synthesized RPS23_G06A

<400> SEQUENCE: 23

Val Leu Glu Lys Val Ala Val Glu Ala Lys Gln Pro Asn Ser Ala Ile
1               5                   10                  15

Arg Lys Cys Val
            20

<210> SEQ ID NO 24
<211> LENGTH: 20
<212> TYPE: PRT
<213> ORGANISM: Artificial sequence
<220> FEATURE:
<223> OTHER INFORMATION: Synthesized RPS23_V07A

<400> SEQUENCE: 24

Val Leu Glu Lys Val Gly Ala Glu Ala Lys Gln Pro Asn Ser Ala Ile
1               5                   10                  15

Arg Lys Cys Val
            20

<210> SEQ ID NO 25
<211> LENGTH: 20
<212> TYPE: PRT
<213> ORGANISM: Artificial sequence
<220> FEATURE:
<223> OTHER INFORMATION: Synthesized RPS23_E08A

<400> SEQUENCE: 25

Val Leu Glu Lys Val Gly Val Ala Ala Lys Gln Pro Asn Ser Ala Ile
1               5                   10                  15

Arg Lys Cys Val
            20

<210> SEQ ID NO 26
<211> LENGTH: 20
<212> TYPE: PRT
<213> ORGANISM: Artificial sequence
<220> FEATURE:
<223> OTHER INFORMATION: Synthesized RPS23_K10A

<400> SEQUENCE: 26
```

```
Val Leu Glu Lys Val Gly Val Glu Ala Ala Gln Pro Asn Ser Ala Ile
1               5                   10                  15

Arg Lys Cys Val
            20

<210> SEQ ID NO 27
<211> LENGTH: 20
<212> TYPE: PRT
<213> ORGANISM: Artificial sequence
<220> FEATURE:
<223> OTHER INFORMATION: Synthesized RPS23_Q11A

<400> SEQUENCE: 27

Val Leu Glu Lys Val Gly Val Glu Ala Lys Ala Pro Asn Ser Ala Ile
1               5                   10                  15

Arg Lys Cys Val
            20

<210> SEQ ID NO 28
<211> LENGTH: 20
<212> TYPE: PRT
<213> ORGANISM: Artificial sequence
<220> FEATURE:
<223> OTHER INFORMATION: Synthesized RPS23_P12A

<400> SEQUENCE: 28

Val Leu Glu Lys Val Gly Val Glu Ala Lys Gln Ala Asn Ser Ala Ile
1               5                   10                  15

Arg Lys Cys Val
            20

<210> SEQ ID NO 29
<211> LENGTH: 20
<212> TYPE: PRT
<213> ORGANISM: Artificial sequence
<220> FEATURE:
<223> OTHER INFORMATION: Synthesized RPS23_P12I

<400> SEQUENCE: 29

Val Leu Glu Lys Val Gly Val Glu Ala Lys Gln Ile Asn Ser Ala Ile
1               5                   10                  15

Arg Lys Cys Val
            20

<210> SEQ ID NO 30
<211> LENGTH: 20
<212> TYPE: PRT
<213> ORGANISM: Artificial sequence
<220> FEATURE:
<223> OTHER INFORMATION: Synthesized RPS23_N13A

<400> SEQUENCE: 30

Val Leu Glu Lys Val Gly Val Glu Ala Lys Gln Pro Ala Ser Ala Ile
1               5                   10                  15

Arg Lys Cys Val
            20

<210> SEQ ID NO 31
<211> LENGTH: 20
<212> TYPE: PRT
<213> ORGANISM: Artificial sequence
<220> FEATURE:
<223> OTHER INFORMATION: Synthesized RPS23_S14A

<400> SEQUENCE: 31
```

Val Leu Glu Lys Val Gly Val Glu Ala Lys Gln Pro Asn Ala Ala Ile
1               5                   10                  15

Arg Lys Cys Val
            20

<210> SEQ ID NO 32
<211> LENGTH: 20
<212> TYPE: PRT
<213> ORGANISM: Artificial sequence
<220> FEATURE:
<223> OTHER INFORMATION: Synthesized RPS23_I16A

<400> SEQUENCE: 32

Val Leu Glu Lys Val Gly Val Glu Ala Lys Gln Pro Asn Ser Ala Ala
1               5                   10                  15

Arg Lys Cys Val
            20

<210> SEQ ID NO 33
<211> LENGTH: 20
<212> TYPE: PRT
<213> ORGANISM: Artificial sequence
<220> FEATURE:
<223> OTHER INFORMATION: Synthesized RPS23_R17A

<400> SEQUENCE: 33

Val Leu Glu Lys Val Gly Val Glu Ala Lys Gln Pro Asn Ser Ala Ile
1               5                   10                  15

Ala Lys Cys Val
            20

<210> SEQ ID NO 34
<211> LENGTH: 20
<212> TYPE: PRT
<213> ORGANISM: Artificial sequence
<220> FEATURE:
<223> OTHER INFORMATION: Synthesized RPS23_K18A

<400> SEQUENCE: 34

Val Leu Glu Lys Val Gly Val Glu Ala Lys Gln Pro Asn Ser Ala Ile
1               5                   10                  15

Arg Ala Cys Val
            20

<210> SEQ ID NO 35
<211> LENGTH: 20
<212> TYPE: PRT
<213> ORGANISM: Artificial sequence
<220> FEATURE:
<223> OTHER INFORMATION: Synthesized RPS23_C19A

<400> SEQUENCE: 35

Val Leu Glu Lys Val Gly Val Glu Ala Lys Gln Pro Asn Ser Ala Ile
1               5                   10                  15

Arg Lys Ala Val
            20

<210> SEQ ID NO 36
<211> LENGTH: 407
<212> TYPE: PRT
<213> ORGANISM: Homo sapiens

<400> SEQUENCE: 36

```
Met Asp Ser Pro Cys Gln Pro Gln Pro Leu Ser Gln Ala Leu Pro Gln
1               5                   10                  15

Leu Pro Gly Ser Ser Glu Pro Leu Glu Pro Glu Pro Gly Arg Ala
            20                  25                  30

Arg Met Gly Val Glu Ser Tyr Leu Pro Cys Pro Leu Leu Pro Ser Tyr
        35                  40                  45

His Cys Pro Gly Val Pro Ser Glu Ala Ser Ala Gly Ser Gly Thr Pro
    50                  55                  60

Arg Ala Thr Ala Thr Ser Thr Thr Ala Ser Pro Leu Arg Asp Gly Phe
65              70                  75                  80

Gly Gly Gln Asp Gly Gly Glu Leu Arg Pro Leu Gln Ser Glu Gly Ala
                85                  90                  95

Ala Ala Leu Val Thr Lys Gly Cys Gln Arg Leu Ala Ala Gln Gly Ala
            100                 105                 110

Arg Pro Glu Ala Pro Lys Arg Lys Trp Ala Glu Asp Gly Gly Asp Ala
        115                 120                 125

Pro Ser Pro Ser Lys Arg Pro Trp Ala Arg Gln Glu Asn Gln Glu Ala
    130                 135                 140

Glu Arg Glu Gly Gly Met Ser Cys Ser Cys Ser Ser Gly Ser Gly Glu
145             150                 155                 160

Ala Ser Ala Gly Leu Met Glu Glu Ala Leu Pro Ser Ala Pro Glu Arg
            165                 170                 175

Leu Ala Leu Asp Tyr Ile Val Pro Cys Met Arg Tyr Tyr Gly Ile Cys
                180                 185                 190

Val Lys Asp Ser Phe Leu Gly Ala Ala Leu Gly Gly Arg Val Leu Ala
    195                 200                 205

Glu Val Glu Ala Leu Lys Arg Gly Gly Arg Leu Arg Asp Gly Gln Leu
    210                 215                 220

Val Ser Gln Arg Ala Ile Pro Pro Arg Ser Ile Arg Gly Asp Gln Ile
225                 230                 235                 240

Ala Trp Val Glu Gly His Glu Pro Gly Cys Arg Ser Ile Gly Ala Leu
                245                 250                 255

Met Ala His Val Asp Ala Val Ile Arg His Cys Ala Gly Arg Leu Gly
            260                 265                 270

Ser Tyr Val Ile Asn Gly Arg Thr Lys Ala Met Val Ala Cys Tyr Pro
    275                 280                 285

Gly Asn Gly Leu Gly Tyr Val Arg His Val Asp Asn Pro His Gly Asp
        290                 295                 300

Gly Arg Cys Ile Thr Cys Ile Tyr Tyr Leu Asn Gln Asn Trp Asp Val
305                 310                 315                 320

Lys Val His Gly Gly Leu Leu Gln Ile Phe Pro Glu Gly Arg Pro Val
                325                 330                 335

Val Ala Asn Ile Glu Pro Leu Phe Asp Arg Leu Leu Ile Phe Trp Ser
            340                 345                 350

Asp Arg Arg Asn Pro His Glu Val Lys Pro Ala Tyr Ala Thr Arg Tyr
        355                 360                 365

Ala Ile Thr Val Trp Tyr Phe Asp Ala Lys Glu Arg Ala Ala Ala Lys
    370                 375                 380

Asp Lys Tyr Gln Leu Ala Ser Gly Gln Lys Gly Val Gln Val Pro Val
385                 390                 395                 400

Ser Gln Pro Pro Thr Pro Thr
                405
```

<210> SEQ ID NO 37
<211> LENGTH: 426
<212> TYPE: PRT
<213> ORGANISM: Homo sapiens

<400> SEQUENCE: 37

| | | | | | | | | | | | | | | | |
|---|---|---|---|---|---|---|---|---|---|---|---|---|---|---|---|
| Met | Ala | Asn | Asp | Ser | Gly | Gly | Pro | Gly | Gly | Pro | Ser | Pro | Ser | Glu | Arg |
| 1 | | | | 5 | | | | | 10 | | | | | 15 | |
| Asp | Arg | Gln | Tyr | Cys | Glu | Leu | Cys | Gly | Lys | Met | Glu | Asn | Leu | Leu | Arg |
| | | | 20 | | | | | 25 | | | | | 30 | | |
| Cys | Ser | Arg | Cys | Arg | Ser | Ser | Phe | Tyr | Cys | Cys | Lys | Glu | His | Gln | Arg |
| | | 35 | | | | | 40 | | | | | 45 | | | |
| Gln | Asp | Trp | Lys | Lys | His | Lys | Leu | Val | Cys | Gln | Gly | Ser | Glu | Gly | Ala |
| | 50 | | | | | 55 | | | | | 60 | | | | |
| Leu | Gly | His | Gly | Val | Gly | Pro | His | Gln | His | Ser | Gly | Pro | Ala | Pro | Pro |
| 65 | | | | | 70 | | | | | 75 | | | | | 80 |
| Ala | Ala | Val | Pro | Pro | Pro | Arg | Ala | Gly | Ala | Arg | Glu | Pro | Arg | Lys | Ala |
| | | | | 85 | | | | | 90 | | | | | 95 | |
| Ala | Ala | Arg | Arg | Asp | Asn | Ala | Ser | Gly | Asp | Ala | Ala | Lys | Gly | Lys | Val |
| | | | 100 | | | | | 105 | | | | | 110 | | |
| Lys | Ala | Lys | Pro | Pro | Ala | Asp | Pro | Ala | Ala | Ala | Ser | Pro | Cys | Arg |
| | | 115 | | | | | 120 | | | | | 125 | | | |
| Ala | Ala | Ala | Gly | Gly | Gln | Gly | Ser | Ala | Val | Ala | Glu | Ala | Glu | Pro |
| | 130 | | | | | 135 | | | | | 140 | | | | |
| Gly | Lys | Glu | Glu | Pro | Pro | Ala | Arg | Ser | Ser | Leu | Phe | Gln | Glu | Lys | Ala |
| 145 | | | | | 150 | | | | | 155 | | | | | 160 |
| Asn | Leu | Tyr | Pro | Pro | Ser | Asn | Thr | Pro | Gly | Asp | Ala | Leu | Ser | Pro | Gly |
| | | | | 165 | | | | | 170 | | | | | 175 | |
| Gly | Gly | Leu | Arg | Pro | Asn | Gly | Gln | Thr | Lys | Pro | Leu | Pro | Ala | Leu | Lys |
| | | | 180 | | | | | 185 | | | | | 190 | | |
| Leu | Ala | Leu | Glu | Tyr | Ile | Val | Pro | Cys | Met | Asn | Lys | His | Gly | Ile | Cys |
| | | 195 | | | | | 200 | | | | | 205 | | | |
| Val | Val | Asp | Asp | Phe | Leu | Gly | Lys | Glu | Thr | Gly | Gln | Gln | Ile | Gly | Asp |
| | 210 | | | | | 215 | | | | | 220 | | | | |
| Glu | Val | Arg | Ala | Leu | His | Asp | Thr | Gly | Lys | Phe | Thr | Asp | Gly | Gln | Leu |
| 225 | | | | | 230 | | | | | 235 | | | | | 240 |
| Val | Ser | Gln | Lys | Ser | Asp | Ser | Ser | Lys | Asp | Ile | Arg | Gly | Asp | Lys | Ile |
| | | | | 245 | | | | | 250 | | | | | 255 | |
| Thr | Trp | Ile | Glu | Gly | Lys | Glu | Pro | Gly | Cys | Glu | Thr | Ile | Gly | Leu | Leu |
| | | | 260 | | | | | 265 | | | | | 270 | | |
| Met | Ser | Ser | Met | Asp | Asp | Leu | Ile | Arg | His | Cys | Asn | Gly | Lys | Leu | Gly |
| | | 275 | | | | | 280 | | | | | 285 | | | |
| Ser | Tyr | Lys | Ile | Asn | Gly | Arg | Thr | Lys | Ala | Met | Val | Ala | Cys | Tyr | Pro |
| | 290 | | | | | 295 | | | | | 300 | | | | |
| Gly | Asn | Gly | Thr | Gly | Tyr | Val | Arg | His | Val | Asp | Asn | Pro | Asn | Gly | Asp |
| 305 | | | | | 310 | | | | | 315 | | | | | 320 |
| Gly | Arg | Cys | Val | Thr | Cys | Ile | Tyr | Tyr | Leu | Asn | Lys | Asp | Trp | Asp | Ala |
| | | | | 325 | | | | | 330 | | | | | 335 | |
| Lys | Val | Ser | Gly | Gly | Ile | Leu | Arg | Ile | Phe | Pro | Glu | Gly | Lys | Ala | Gln |
| | | | 340 | | | | | 345 | | | | | 350 | | |
| Phe | Ala | Asp | Ile | Glu | Pro | Lys | Phe | Asp | Arg | Leu | Leu | Phe | Phe | Trp | Ser |
| | | 355 | | | | | 360 | | | | | 365 | | | |
| Asp | Arg | Arg | Asn | Pro | His | Glu | Val | Gln | Pro | Ala | Tyr | Ala | Thr | Arg | Tyr |
| | 370 | | | | | 375 | | | | | 380 | | | | |

```
Ala Ile Thr Val Trp Tyr Phe Asp Ala Asp Glu Arg Ala Arg Ala Lys
385                 390                 395                 400

Val Lys Tyr Leu Thr Gly Glu Lys Gly Val Arg Val Glu Leu Asn Lys
                405                 410                 415

Pro Ser Asp Ser Val Gly Lys Asp Val Phe
                420                 425
```

<210> SEQ ID NO 38
<211> LENGTH: 239
<212> TYPE: PRT
<213> ORGANISM: Homo sapiens

<400> SEQUENCE: 38

```
Met Pro Leu Gly His Ile Met Arg Leu Asp Leu Glu Lys Ile Ala Leu
1               5                   10                  15

Glu Tyr Ile Val Pro Cys Leu His Glu Val Gly Phe Cys Tyr Leu Asp
                20                  25                  30

Asn Phe Leu Gly Glu Val Val Gly Asp Cys Val Leu Glu Arg Val Lys
            35                  40                  45

Gln Leu His Cys Thr Gly Ala Leu Arg Asp Gly Gln Leu Ala Gly Pro
        50                  55                  60

Arg Ala Gly Val Ser Lys Arg His Leu Arg Gly Asp Gln Ile Thr Trp
65                  70                  75                  80

Ile Gly Gly Asn Glu Glu Gly Cys Glu Ala Ile Ser Phe Leu Leu Ser
                85                  90                  95

Leu Ile Asp Arg Leu Val Leu Tyr Cys Gly Ser Arg Leu Gly Lys Tyr
                100                 105                 110

Tyr Val Lys Glu Arg Ser Lys Ala Met Val Ala Cys Tyr Pro Gly Asn
            115                 120                 125

Gly Thr Gly Tyr Val Arg His Val Asp Asn Pro Asn Gly Asp Gly Arg
        130                 135                 140

Cys Ile Thr Cys Ile Tyr Tyr Leu Asn Lys Asn Trp Asp Ala Lys Leu
145                 150                 155                 160

His Gly Gly Ile Leu Arg Ile Phe Pro Glu Gly Lys Ser Phe Ile Ala
                165                 170                 175

Asp Val Glu Pro Ile Phe Asp Arg Leu Leu Phe Phe Trp Ser Asp Arg
                180                 185                 190

Arg Asn Pro His Glu Val Gln Pro Ser Tyr Ala Thr Arg Tyr Ala Met
            195                 200                 205

Thr Val Trp Tyr Phe Asp Ala Glu Glu Arg Ala Glu Ala Lys Lys Lys
        210                 215                 220

Phe Arg Asn Leu Thr Arg Lys Thr Glu Ser Ala Leu Thr Glu Asp
225                 230                 235
```

<210> SEQ ID NO 39
<211> LENGTH: 199
<212> TYPE: PRT
<213> ORGANISM: Saccharomyces cerevisiae

<400> SEQUENCE: 39

```
Ser Gln Pro Tyr Asn Trp Gly Thr Ile His Glu Leu Val Asn Asp Asp
1               5                   10                  15

Leu Leu Arg Ala Val Arg Lys Glu Ile Glu Thr Glu Ile His Phe Thr
                20                  25                  30

Lys Lys Glu Thr Asp Ile Tyr Arg Val Asn Gln Ser Gly Asp Leu Ala
            35                  40                  45
```

```
Asn Leu Ser Gly Leu Asp Trp Asp Asp Leu Ser Arg Leu Pro Asn Leu
    50                  55                  60
Phe Lys Leu Arg Gln Ile Leu Tyr Ser Lys Gln Tyr Arg Asp Phe Phe
 65              70                  75                      80
Gly Tyr Val Thr Lys Ala Gly Lys Leu Ser Gly Ser Lys Thr Asp Met
                 85                  90                  95
Ser Ile Asn Thr Tyr Thr Lys Gly Cys His Leu Leu Thr His Asp Asp
                100                 105                110
Val Ile Gly Ser Arg Arg Ile Ser Phe Ile Leu Tyr Leu Pro Asp Pro
            115                 120                 125
Asp Arg Lys Trp Lys Ser His Tyr Gly Gly Gly Leu Arg Leu Phe Pro
    130                 135                 140
Ser Ile Leu Pro Asn Val Pro His Ser Asp Pro Ser Ala Lys Leu Val
145                 150                 155                 160
Pro Gln Phe Asn Gln Ile Ala Phe Phe Lys Val Leu Pro Gly Phe Ser
                165                 170                 175
Phe His Asp Val Glu Glu Val Lys Val Asp Lys His Arg Leu Ser Ile
            180                 185                 190
Gln Gly Trp Tyr His Ile Pro
            195
```

US 9,228,224 B2

METHOD FOR ASSAYING OGFOD1 ACTIVITY

CROSS-REFERENCE TO RELATED APPLICATIONS

This application is the U.S. national stage filing under 35 U.S.C. §371 of PCT International Application PCT/GB2012/050303, filed Feb. 10, 2012, which claims priority from GB Patent Application 1102659.8, filed Feb. 15, 2011.

FIELD OF THE INVENTION

The present invention relates to assays for monitoring activity of a newly identified family of ribosome prolyl-hydroxylases, in particular, to assays for identifying modulators of ribosome prolyl-hydroxylase activity. The invention also relates to the introduction of 3-hydroxyprolyl residues into peptides and proteins.

BACKGROUND TO THE INVENTION

The oxygenase-catalyzed post-translational hydroxylation of prolyl residues is important for protein function and structure in animals. In the case of collagen, prolyl-4-hydroxylation stabilises the triple helix fold whereas prolyl-3-hydroxylation is thought to destabilise the triple helix fold. More recently, prolyl-4-hydroxylation has been shown to play an important role in the animal hypoxic response by signalling for the proteasomally mediated degradation of the hypoxia inducible transcription factor alpha subunit (HIFα) by enhancing its binding to the targeting component of a ubiquitin ligase. The oxygen dependence of the HIFα prolyl hydroxylases (PHD/EGLN enzymes), in addition to appropriate kinetic properties, is proposed to enable them to act as an oxygen-sensing component for the HIF-based hypoxic response system, which is conserved in all animals and involves transcriptional regulation of multiple genes in a context-dependent manner. Several reports of alternative substrates for the PHDs have emerged but the biological role of these modifications is unclear.

In some animals, including humans, HIF transcriptional activity is also regulated by asparaginyl hydroxylation, which reduces HIF binding to transcriptional coactivator proteins including p300. The HIF asparaginyl hydroxylase (FIH) and the PHDs belong to the ubiquitous family of Fe(II) and 2-oxoglutarate-dependent oxygenases (2OG oxygenases). 2OG oxygenases couple the two-electron oxidation of their 'prime' substrate to the oxidative decarboxylation of 2OG to give carbon dioxide ($CO_2$) and succinate.

A number of human 2OG oxygenases are of therapeutic interest including the hypoxia inducible factor prolyl (PHD) and asparaginyl hydroxylases (FIH), the deoxyribonucleic acid demethylases (ALKBHs and FTO), the 5-methylcytosine hydroxylases (TET enzymes), ribonucleic acid hydroxylases (C2ORF60), lysyl hydroxylases (JMJD6), phytanoyl coenzyme A hydroxylase (PAHX), procollagen prolyl and lysyl hydroxylases, and the histone lysyl and arginyl demethylases (JMJ-domain containing enzymes, FBXL11, PHF8).

Following the assignment of the HIF hydroxylases as 2OG oxygenases and the solution of crystal structures for them, several other oxygenases with unknown function were identified by structurally informed bioinformatic analyses. Importantly, the JmjC jumonji-domain-containing oxygenases that bear structural similarity with FIH have been found to catalyze the N-demethylation of $N^\epsilon$-lysyl residues of histones. Further, FIH itself has been found to have multiple substrates from the ankyrin repeat domain family, including transcription factors, and JMJD6 was found to catalyze lysyl 5-hydroxylation of splicing-related proteins. Collectively, these results suggest the presence of multiple regulatory levels and interfaces between oxygen and transcriptional activity, and maybe splicing, which are mediated by 2OG oxygenases.

SUMMARY OF THE INVENTION

The present inventors have identified that OGFOD1 is a 2OG oxygenase, and specifically is a prolyl-trans-3-hydroxylase. A substrate for OGFOD1 is identified as human ribosomal protein RPS23. Accordingly, the present invention provides a method for assaying OGFOD1 activity, the method comprising contacting a peptide comprising a prolyl residue, with an OGFOD1 polypeptide and determining whether the prolyl residue in said peptide is hydroxylated. The invention also provides a method for identifying an inhibitor or activator of OGFOD1 oxygenase activity, the method comprising contacting an OGFOD1 polypeptide and a prolyl-residue containing peptide with a test agent under conditions suitable for oxygenase activity, and monitoring for hydroxylation of said peptide.

The invention further provides a method for identifying a modulator of protein translation, the method comprising contacting a cell which expresses OGFOD1 with a test agent and determining whether the test agent modulates the OGFOD1 mediated regulation of protein translation.

The invention further provides an inhibitor or activator of 2OG oxygenase activity for use in modulating prolyl hydroxylation by OGFOD1 of a ribosomal protein or a fragment or variant thereof comprising a prolyl residue, or for use in modulating protein translation.

BRIEF DESCRIPTION OF THE FIGURES

FIG. 1: shows a ClustalW alignment of OGFOD1 homologue sequences. Human gi|94536836 (SEQ ID NO:1), orang-utan gi|207080340 (*97%)(SEQ ID NO:2), cow gi|262205525 (*87%)(SEQ ID NO:3), rat gi|157817865 (*82%)(SEQ ID NO:4), mouse gi|147901538 (*82%) (SEQ ID NO:5) [* indicates sequence identity with human OGFOD1 (SEQ ID NO:1)].

FIG. 2 shows a ClustalW sequence alignment of the catalytic 2OG oxygenase domains of human OGFOD1 (residues 58 to 249 of SEQ ID NO:1), yeast TPA1 (SEQ ID NO:39), and the human hypoxia inducible factor prolyl hydroxylases 1-3 (PHD1, PHD2, PHD3; also known as EGLN3 (residues 23 to 225 of SEQ ID NO:38), EGLN1 (residues 202 to 403 of SEQ ID NO:37) and EGLN2 (residues 186 to 387 of SEQ ID NO:36), respectively). The sequences of PHD1, PHD2 and PHD3 are set out in SEQ ID NOs: 36 to 38. The secondary structure was predicted based on this alignment using JPred3 as implemented in JalView and is shown below. Roman numerals indicate the eight core DSBH strands. (Note: Strand VII was not predicted automatically and was assigned by manual comparison of sequences and structures).

FIG. 3 shows the results of a 2OG turnover assay for determining the enzymatic activity of full-length OGFOD1 (SEQ ID NO:1). Values shown are averages of two or three experiments. Error bars represent standard deviations. The assay was carried out for 20 min at 37° C. using 8 μM recombinant full-length human OGFOD1 (SEQ ID NO:1), 288 μM 2OG, 3.7 μM 1-[$^{14}$C]-2OG (specific activity 56.8 μCi/nmol, stock concentration 1.83 mM), RPS23 peptide, 100 μM (NH₄)₂Fe(SO₄)₂, 4 mM ascorbate, 0.66 mg/ml catalase, 1 mM DTT, 50 mM Tris.HCl pH 7.5, and with one of OGFOD1, (NH₄)₂Fe(SO₄)₂ and ascorbate missing from the assay. The assay was also performed in the presence of 1 mM pyridine 2,4-dicarboxylic acid (2,4-PDCA).

BRIEF DESCRIPTION OF THE SEQUENCES

Figure 4:
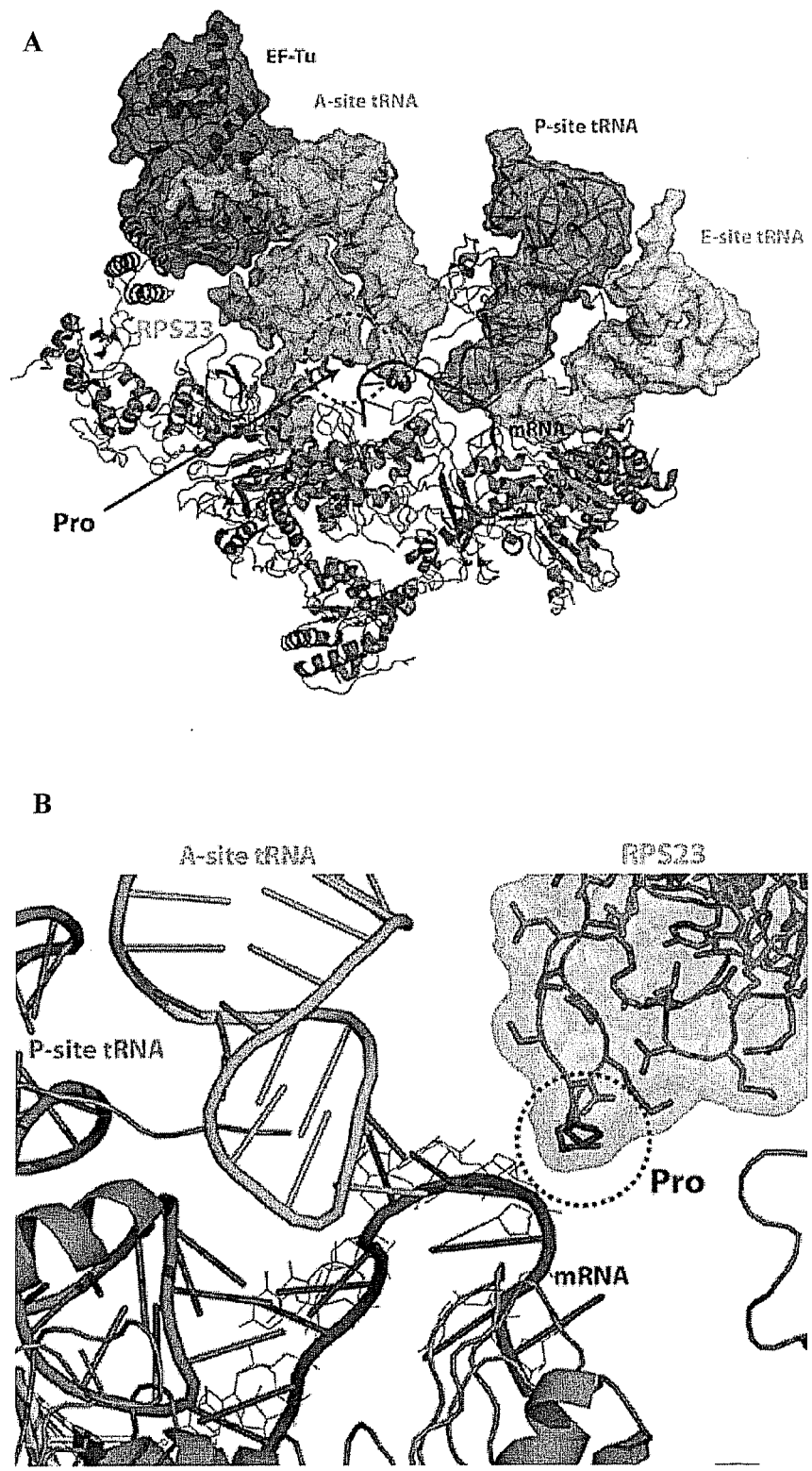
FIG. 4 shows some structural aspects of the RPS23 OGFOD1 substrate and the decoding centre of the ribosome, with relevance to OGFOD1 function. A is a depiction of the structure of the small subunit of the *Thermus Thermophilus* ribosome (derived from crystallographic data, asymmetric unit based on PDB IDs 2WRN, 2WRO, 2WRQ and 2WRR. Note: rRNA is not shown). Pro-62 of the RPS23 homologue, S12, is located to interact with template mRNA during the translation process. Panel B is a magnification of Panel A, showing the key structural position of Pro-62 and its spatial proximity to the decoding centre of the ribosome, thus suggesting a role of Pro-62 hydroxylation in modulation of translational accuracy and/or efficiency of stop codon recognition and translation termination.

SEQ ID NO: 1 is the amino acid sequence of human OGFOD1 (gi|94536836).

SEQ ID NO: 2 is the amino acid sequence of orang-utan OGFOD1 which shares 97% sequence identity with human OGFOD1 (gi|207080340).

SEQ ID NO: 3 is the amino acid sequence of cow OGFOD1 which shares 87% sequence identity with human OGFOD1 (gi|262205525).

SEQ ID NO: 4 is the amino acid sequence of rat OGFOD1 which shares 82% sequence identity with human OGFOD1 (gi|157817865).

SEQ ID NO: 5 is the amino acid sequence of mouse OGFOD1 which shares 82% sequence identity with human OGFOD1 (gi|147901538).

SEQ ID NO: 6 is the amino acid sequence of human ribosomal protein RPS23 (gi|4506701).

SEQ ID NO: 7 is the amino acid sequence of the C-terminal domain of OGFOD1 cloned into pET21d.

SEQ ID NOs: 8 and 9 are the forward and reverse primers for OGFOD1_Q261.

SEQ ID NO: 10 is the amino acid sequence of the H155A mutant of full-length human OGFOD1 cloned into pET28.

SEQ ID NOs: 11 and 12 are the forward and reverse primers for the OGFOD1_H155A mutant.

SEQ ID NO: 13 is the amino acid sequence of the D157A mutant of full-length human OGFOD1 cloned into pET28.

SEQ ID NOs: 14 and 15 are the forward and reverse primers for the OGFOD1_D157A mutant.

SEQ ID NOs: 16 to 35 are the amino acid sequences of the RPS23 peptides used to assess the specificity of OGFOD1.

SEQ ID NO: 36 is the amino acid sequence of human PHD1 (gi|16604260).

SEQ ID NO: 37 is the amino acid sequence of human PHD2 (gi|13489073).

SEQ ID NO: 38 is the amino acid sequence of human PHD3 (gi|11545787).

DETAILED DESCRIPTION OF THE INVENTION

The present inventors have shown experimentally for the first time that OGFOD1 has 2-oxoglutarate (2OG) dependent oxygenase activity and in particular catalyses hydroxylation of prolyl residues at the C-3 position. The present inventors have successfully purified recombinant OGFOD1. OGFOD1 can be inhibited by 2OG oxygenase inhibitors, including some known to inhibit the HIF prolyl hydroxylases and the collagen prolyl hydroxylases. A substrate for this prolyl hydroxylase activity has been identified, namely the human ribosomal protein S23 (RPS23). The inventors have also shown that OGFOD1 catalyses trans-3-prolyl hydroxylation of Pro-62 of the RPS23 protein.

The present invention provides a method for assaying OGFOD1 activity, the method comprising contacting an OGFOD1 polypeptide with a peptide containing a prolyl residue, and determining whether the peptide is hydroxylated at the prolyl residue.

An OGFOD1 polypeptide in accordance with the present invention is typically human OGFOD1 or a homologue thereof, a variant thereof which retains prolyl hydroxylase activity, or a fragment of any thereof which retains prolyl hydroxylase activity. The sequence of human OGFOD1 is set out in SEQ ID NO: 1. Homologues thereof may be derived from other species, including in particular mammalian species. Exemplary species include orangutan, cow, rat and mouse.

The OGFOD1 polypeptide may comprise the sequence shown in SEQ ID NO: 1, or may be a fragment or variant of SEQ ID NO: 1 having prolyl hydroxylase activity. Fragments of OGFOD1 are described in more detail below. The OGFOD1 polypeptide may have an amino acid sequence having at least about 60% sequence identity, for example at least about 70% sequence identity, with SEQ ID NO: 1 over its entire length or over an active fragment thereof (such as SEQ ID NO: 2), typically greater than about 80% or 90%, such as about 95% or about 99% sequence identity.

Sequence identity may be calculated using any suitable algorithm. For example, the UWGCG Package provides the BESTFIT program can be used to infer homology (for example used on its default settings) (Devereux et al. (1984) *Nucleic Acids Research* 12, p 387-395). The PILEUP and BLAST algorithms can be used to infer homology or line up sequences (typically on their default settings), for example as described in Latched (1993) J. Mol. Evol 36:290-300; Latched et al. (1990) J. Mol. Biol. 215:403-10.

The OGFOD1 polypeptide may be a polypeptide encoded by any naturally occurring OGFOD1 gene in humans or other organisms. The naturally occurring OGFOD1 gene may encode the sequence shown in SEQ ID NO: 1 or may encode a variant or homologue. Such variants may include allelic variants and the deletion, modification or addition of single amino acids or groups of amino acids within the protein sequence, as long as the polypeptide retains prolyl hydroxylase activity.

Amino acid substitutions of SEQ ID NO: 1, or of a fragment thereof may be made, for example from about 1, 2 or 3 to about 10, 20 or 30 substitutions. Conservative substitutions may be made, for example according to the following Table. Amino acids in the same block in the second column and preferably in the same line in the third column may be substituted for each other.

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

Variant polypeptides within the scope of the invention may be generated by any suitable method, for example by gene shuffling techniques.

The present invention also includes use of active portions, fragments, derivatives and functional mimetic of the polypeptides of the invention. An "active portion" of a polypeptide means a peptide which is less than said full-length polypeptide, but which retains prolyl hydroxylase activity. An active fragment of OGFOD1 may typically be identified by monitoring for 2OG oxygenase activity as described in more detail below. Such an active fragment may be included as part of a fusion protein.

The fragment may have up to about 200, 250, 300, 350, 400, 450, 500, 550, or 560 amino acids. The fragment may comprise any region from the amino acid sequence shown in SEQ ID NO: 1, such as from amino acid 2, 3, 4, 5 or about 10 to about amino acid 500, 510, 520, 530, 540, 550, or 560. Useful fragments include N-terminal (or C-terminal) truncated fragments i.e., fragments comprising an N-terminal deletion, such as fragments comprising residues 10 to 565, 20 to 565 or 25 to 565 of the amino acid sequence shown in SEQ ID NO: 1. Useful fragments also include fragments comprising C-terminal truncations such as fragments comprising residues 1 to 560, 1 to 550 or 1 to 530 of the amino acid sequence shown in SEQ ID NO: 1. Useful fragments also include fragments comprising both N-terminal and C-terminal truncations, such as fragment comprising residues 10 to 560, 20 to 550 or 25 to 530 of the amino acid sequence shown in SEQ ID NO: 1. Other suitable fragments may readily be identified, for example by comparing the OGFOD1 amino acid sequence to the amino acid sequence of one or more known 2OG oxygenases and identifying which regions are homologous to regions having catalytic activity. The regions having catalytic activity are typically included in the active fragments. Such fragments can be used to construct chimerical molecules. Fragments of any OGFOD1 polypeptide having at least about 60%, such as at least about 70%, 80%, 90%, 95% or 99% sequence identity to the amino acid sequence shown in SEQ ID NO: 1, which fragments have prolyl hydroxylase activity may also be used in an assay of the invention and are encompassed within the term "OGFOD1 polypeptide" used herein.

The OGFOD1 polypeptide may comprise one or more particular site directed mutations.

The OGFOD1 polypeptides may be synthetically prepared. The polypeptides may be chemically or biochemically modified, e.g. post-translationally modified. For example, they may be glycosylated or comprise modified amino acid residues. They may also be modified by the addition of histidine residues (typically six), or other sequence tags such as a maltose binding protein tag or intein tag, to assist their purification or by the addition of a nuclear localisation sequence to promote translocation to the nucleus or mitochondria, and or by post-translational modification including hydroxylation or phosphorylation. Polypeptides of the invention may be GST or other suitable fusion polypeptides. The OGFOD1 polypeptide may also be modified by addition of fluorescent tags (such as green or yellow fluorescent protein) to enable visualisation within cells or organelles or to aid purification of the protein or cells expressing OGFOD1. Such modified polypeptides fall within the scope of the term "OGFOD1 polypeptide".

The OGFOD1 polypeptide of the invention may be present in a partially purified or in a substantially isolated form. The polypeptide may be mixed with carriers or diluents, which will not interfere with its intended use and still be regarded as substantially isolated. The polypeptide may also be in a substantially purified form, in which case it will generally comprise at least about 90%, e.g. at least about 95%, 98% or 99%, of the proteins, polynucleotides, cells or dry mass of the preparation.

The OGFOD1 polypeptide used in a method of the invention may be recombinant OGFOD1 or naturally occurring OGFOD1. Naturally occurring OGFOD1 may be obtained from any organism that produces an OGFOD1 polypeptide. Preferably, recombinant OGFOD1 is used especially where OGFOD1 is required for purposes requiring large (>1 mg) amounts of protein such as for biophysical assays or for high throughput analyses. Recombinant OGFOD1 may be produced using standard expression vectors that comprise nucleotide sequences encoding OGFOD1. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for protein expression. Other suitable vectors would be apparent to persons skilled in the art. By way of further example in this regard we refer to Sambrook et al. (1989).

The OGFOD1 polypeptide may be present in a cell, including, but not limited to, human-derived cells. For example, methods of the invention may utilise cells that have been modified to express an OGFOD1 polypeptide as defined herein. The OGFOD1 may also be present in a cell extract or in a partially or substantially purified form.

A purified OGFOD1 polypeptide may be obtained by introducing an expression vector comprising a polynucleotide encoding an OGFOD1 polypeptide into a host cell.

Expression vectors are routinely constructed in the art and may for example involve the use of plasmid DNA and appropriate initiators, promoters, enhancers and other elements, such as for example polyadenylation signals which may be necessary and which are positioned in the correct orientation in order to allow full protein expression. Suitable vectors would be very readily apparent to those of skill in the art. Promoter sequences may be inducible or constitutive promoters depending on the selected assay format. The promoter may be tissue specific. Thus the coding sequence in the vector is operably linked to such elements so that they provide for expression of the coding sequence (typically in a cell). The term "operably linked" refers to a juxtaposition wherein the components described are in a relationship permitting them to function in their intended manner.

The vector may be, for example, a plasmid, virus or baculovirus vector. The vector is typically adapted to be used in a bacterial cell, such as E. coli. The vector may have an origin of replication. The vector may comprise one or more selectable marker genes, for example an ampicillin resistance gene in the case of a bacterial plasmid or a resistance gene for a fungal vector. Vectors may be used to transfect or transform a host cell, for example, a bacterial host cell, fungal host cell, an insect host cell, a mammalian, e.g. human host cell or a baculovirus host cell.

Methods for introducing polypeptides and vectors into host cells are well known in the art, and include electroporation and heat shock techniques without limitation. Expression of the truncated polypeptide may then be achieved by culturing the host cells.

The OGFOD1 polypeptide may be purified by lysing the host cells and extracting OGFOD1 from the soluble fraction, for example by affinity purification, such as via an affinity tag fused to the truncated OGFOD1 polypeptide. OGFOD1 polypeptides may be purified by standard techniques known in the art. For example, where the polypeptide comprises a His tag, it may be purified using a His-binding resin by following the manufacturer's instructions (e.g. Novagen) or by other means such as ion exchange chromatography.

The methods of the present invention typically use a peptide containing a prolyl residue as a substrate (or binding agent) for the OGFOD1 polypeptide. Short peptides can be used, for example peptides as short as 6 or 10 amino acids in length, typically at least 11 amino acids in length, such as 12, 13, 14, 15 or 16 amino acids in length up to much longer polypeptides and proteins, of at least 20, 30, 40, 50, 60, 70, 80, 90, 100, 110, 120, 130 or 136 amino acids in length. A full length protein which is a substrate for the OGFOD1 polypeptide can be used, for example the human RPS23 ribosomal protein.

Any suitable peptide can be used, so long as the peptide contains a prolyl residue (or analogue thereof) capable of hydroxylation by OGFOD1 (or of binding to the active site of OGFOD1). The peptide may be modified, e.g. by the presence of a group to facilitate assays such as a fluorescent group; Many such modifications are routinely used and described in the scientific literature.

In preferred aspects of the present invention, the peptide used in the assays is a substrate for OGFOD1 in vivo, or a homologue, variant or fragment thereof. In particular, the present inventors have identified ribosomal protein RPS23 to be a substrate for OGFOD1. Thus a preferred peptide containing a prolyl residue for use in accordance with the present invention is SEQ ID NO: 6 or a variant thereof or a fragment of either thereof. Typically, a variant thereof has an amino acid sequence having at least about 60% sequence identity, for example at least about 70% sequence identity, with SEQ ID NO: 6 over its entire length or over an active fragment thereof, typically greater than about 80% or 90%, such as about 95% or about 99% sequence identity.

Sequence identity may be calculated using any suitable algorithm. For example, the UWGCG Package provides the BESTFIT program can be used to infer homology (for example used on its default settings) (Devereux et al. (1984) *Nucleic Acids Research* 12, p 387-395). The PILEUP and BLAST algorithms can be used to infer homology or line up sequences (typically on their default settings), for example as described in Latched (1993) J. Mol. Evol 36:290-300; Latched et al. (1990) J. Mol. Biol. 215:403-10.

Amino acid substitutions of SEQ ID NO: 6, or of a fragment thereof may be made, for example from about 1, 2 or 3 to about 10, 20 or 30 substitutions. Conservative substitutions may be made, for example according to the following Table. Amino acids in the same block in the second column and preferably in the same line in the third column may be substituted for each other.

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

OGFOD1 has been shown to hydroxylate the prolyl residue at position 62 of SEQ ID NO: 6. Thus a variant or homologue of SEQ ID NO: 6 includes a prolyl residue equivalent to prolyl residue at position 62 of SEQ ID NO: 6.

The assays of the present invention also include the use of fragments of SEQ ID NO: 6 or fragments of the variants thereof as defined above. Such fragments may be as short as 6 amino acids in length, typically at least 10, 11, 12 or 13 or 14 amino acids in length, preferably 16, 17, 18, 19 or 20 amino acids in length and incorporate an proline equivalent to proline at position 62 of SEQ ID NO: 6. The peptide typically comprises the sequence KQPNSAIR. A preferred fragment of RPS23 is VLEKVGVEAKQPNSAIRKCV, residues 50 to 69 of SEQ ID NO: 6. In a preferred embodiment, a peptide substrate for use in accordance with the present invention consists of or comprises this sequence, or variants thereof having 1, 2 or 3 substitutions therein, and retaining a proline equivalent to Pro 62 of SEQ ID No 6.

The method of the invention may be used to identify a modulator of OGFOD1 activity. The assay may be carried out in the presence of a test agent to determine whether the test agent is a modulator of OGFOD1 activity. Such assays may use purified materials or be carried out in cells. Any suitable assay may be carried out to identify modulators of OGFOD1 prolyl hydroxylase activity. A number of different examples of suitable assays are described below. Assays of the invention may be used to identify an agent which modulates, such as inhibits or activates, OGFOD1 prolyl hydroxylase activity.

In a method of the invention OGFOD1 activity may be assayed by monitoring oxygenase activity of an OGFOD1 polypeptide in the presence of substrate. In some embodiments, the substrate is a ribosomal protein such as the human ribosomal protein RPS23 (or other OGFOD1 substrate containing a prolyl-residue). In some embodiments, the OGFOD1 polypeptide hydroxylates Pro-62 of the ribosomal protein RPS23, or fragment or analogue thereof. The substrate and OGFOD1 polypeptide, and optionally the test agent, are typically contacted under conditions suitable for oxygenase (prolyl hydroxylase) activity.

Suitable co-substrates include oxygen, for example, dioxygen, and 2-oxoacids such as 2-oxogluterate (2OG) or 2OG analogues (such as 2-oxoadipate). Preferably, the co-substrate is 2OG. In addition to oxygen or a 2-oxoacid, a reducing agent, such as ascorbate may also be used as a co-substrate. Thus, in a method according to the invention, the ribosomal protein or analogue or fragment thereof and OGFOD1 polypeptide are contacted in the presence of Fe(II), oxygen and 2-oxoglutarate and optionally in the presence of a reducing agent.

Hydroxylation of the substrate may be assayed directly or indirectly. Such assays may employ techniques such as chromatography, NMR, MS or fluorescence spectroscopy. The co-substrate may be modified, e.g. 2OG, consumed, e.g. oxygen, or produced, e.g. succinate or carbon dioxide, by OGFOD1.

In an assay to identify a modulator of OGFOD1 activity, the components of the assay are preferentially contacted under conditions in which OGFOD1 has prolyl hydroxylase/oxygenase activity both in the absence of the test agent and in the presence of the test agent so that the effect of the test agent on OGFOD1 activity may be determined. The assay may also be used to detect agents that increase or decrease the activity of OGFOD1 activity by assaying for increases or decreases in activity including in while organisms. Suitable assays have been described in the art for other 2OG oxygenases including the HIF hydroxylases and histone demethylases. Other assay configurations may rely on methods for assessing binding, e.g. by displacement of an appropriately labelled OGFOD1 binding peptide from the OGFOD1 active site. Cell-based assays in which the hydroxylation status of RPS23 is assessed either by mass spectrometry or by use of appropriate antibodies are also suitable. Such assays have been developed for the HIF prolyl hydroxylases and are amenable to the study of OGFOD1 activity in animals including in humans, including in different tissue types and both healthy and diseased tissues. Measurement of OGFOD1 activity is of particular interest with respect to investigating the hydroxylation status of ribosomes in tissues that are subject to diseases associated with hypoxia such as many tumours, and indeed altered ribosome hydroxylation may be characteristic of such diseases.

Assays of the present invention may be used to identify inhibitors of oxygenase activity and are thus preferably, but not necessarily, carried out under conditions under which OGFOD1 is active as an oxygenase (a prolyl hydroxylase) in the absence of the test agent. The OGFOD1 oxygenase activity in the presence of the test agent is compared to OGFOD1 oxygenase activity in the absence of the test substance to determine whether the test substance is an inhibitor of OGFOD1 oxygenase activity. In the alternative, the assays may be used to look for promoters of OGFOD1 oxygenase activity, for example, by looking for increased conversion of co-substrate and/or hydroxylation of substrates compared to assays carried out in the absence of a test substance. The assays may also be carried out, either with purified materials in cells or in animals, under conditions in which OGFOD1 oxygenase activity is reduced or absent, such as under hypoxic conditions, and the presence of or increased activity can be monitored under such conditions.

In medicinal applications, for example, it is often advantageous to modulate oxygenase activity of a single enzyme or group of enzymes. The assays of the invention may also be used to identify inhibitors or activators that are specific for prolyl hydroxylases, such as OGFOD1 (or homologues of OGFOD1) and which do not have activity or are less active with other 2OG oxygenases, including other human 2OG oxygenases. Conversely, the assays of the invention may be used to identify inhibitors or activators specific for one or more 2OG oxygenases which do not inhibit OGFOD1 activity. Human 2OG oxygenases that may be tested in such a method of the invention are listed in Table 1. Such 2OG oxygenases include, but are not limited to: argininyl, prolyl, and asparaginyl demethylases, hypoxia inducible factor (HIF) asparaginyl or prolyl hydroxylases, including FIH, PHD1, PHD2 and PHD3, AlkB, ABH1, ABH2, ABH3, procollagen prolyl and argininyl hydroxylases, methyl arginine demethylases, Mina53, the fat mass and obesity protein, the epidermal growth factor hydroxylases, AlkB, TauD, and other 2OG oxygenases that have been characterized as Jmj domain proteins according to the SMART database including, but not limited to argininyl demethylases.

TABLE 1

List of known or predicted human 2OG oxygenases

| Sub-family | Gene Id | Protein description |
| --- | --- | --- |
| ASPH | 444 | Aspartyl/asparaginyl beta-hydroxylase (Aspartate beta-hydroxylase) (ASP beta-hydroxylase) (Peptide-aspartate beta-dioxygenase) |
| ASPHD2 | 57168 | hypothetical protein LOC57168 |
| ASPHD1 | 253982 | hypothetical protein LOC253982 |
| C17orf101 | 79701 | PKHD domain-containing transmembrane protein C17orf101 |
| LEPRE1 | 64175 | leucine proline-enriched proteoglycan (leprecan) 1 |
| LEPRE1-like | 55214 | leprecan-like 1 |
| LEPRE2 | 10536 | leprecan-like 2 |
| P4H TM | 54681 | hypoxia-inducible factor prolyl 4-hydroxylase isoform a, transmembrane (endoplasmic reticulum) |
| P4HA3 | 283208 | procollagen-proline, 2-oxoglutarate 4-dioxygenase (proline 4-hydroxylase), alpha polypeptide III |
| P4HA1 | 5033 | procollagen-proline, 2-oxoglutarate 4-dioxygenase (proline 4-hydroxylase), alpha polypeptide I |
| P4HA2 | 8974 | procollagen-proline, 2-oxoglutarate 4-dioxygenase (proline 4-hydroxylase), alpha polypeptide II |
| PLOD3 | 8985 | procollagen-lysine, 2-oxoglutarate 5-dioxygenase 3 |
| PLOD1 | 5351 | procollagen-lysine, 2-oxoglutarate 5-dioxygenase 1 precursor (Lysyl hydroxylase 1) (LH1) |
| PLOD2 | 5352 | procollagen-lysine, 2-oxoglutarate 5-dioxygenase 2 isoform a |
| JMJD4 | 65094 | JMJD4 isoform 1 |
| JMJD6 | 23210 | Phosphatidylserine receptor JMJD6 isoform 1 |
| JMJD5 | 79831 | Hypothetical protein FLJ13798 |
| JMJD8 | 339123 | Hypothetical LOC339123 |
| TYW5/C2orf60 | 129450 | C2orf60 chromosome 2 open reading frame 60 |
| FIH | 55662 | Hypoxia-inducible factor 1 alpha inhibitor (Hypoxia-inducible factor asparagine hydroxylase) (Factor inhibiting HIF-1) (FIH-1) |
| PASS1/HSPBAP1 | 79663 | PASS1 |
| JMJD7/PLA2gIVB | 8681 | phospholipase A2, group IVB |
| NO66 | 79697 | chromosome 14 open reading frame 169 |
| MINA53B | 84864 | MYC induced nuclear antigen, isoform 2 |
| JMJD3/KDB6B | 23135 | jumonji domain containing 3 |
| UTX/KDM6A | 7403 | ubiquitously transcribed tetratricopeptide repeat, X chromosome |
| UTY | 7404 | tetratricopeptide repeat protein isoform 1 |
| JARID1B/PLU-1/KDM5B | 10765 | Jumonji, AT rich interactive domain 1B (RBP2-like) |
| JARID1A/RBBP2/KDM5A | 5927 | retinoblastoma binding protein 2 |
| JARID1C/SMCX/KDM5C | 8242 | Smcx homolog, X chromosome |
| JARID1D/SMCY/KDM5D | 8284 | Smcy homolog, Y-linked |
| JMJD2A/JHDM3A/KDM4A | 9682 | jumonji domain containing 2A |
| JMJD2C/GASC1/KDM4C | 23081 | jumonji domain containing 2C |
| JMJD2B/KDM4C | 23030 | jumonji domain containing 2B |
| JMJD2D/KDM4D | 55693 | jumonji domain containing 2D |
| JMJD2E/KDM4E | | jumonji domain containing 2E; pseudogene |
| FBXL10/JHDM1B/KDM2B | 84678 | F-box and leucine-rich repeat protein 10 |
| FBXL11/JHDM1A/KDM2A | 22992 | F-box and leucine-rich repeat protein 11 |
| KIAA1718/JHDM1D | 80853 | KIAA1718 protein |
| PHF8/KIAA1111 | 23133 | PHD finger protein 8 |
| PHF2/JHDM1E/GRC5 | 5253 | PHD finger protein 2 isoform a |
| HR | 55806 | Hairless |
| JMJD1A/KDM3A/TSGA | 55818 | jumonji domain containing 1A |
| JMJD1B/KDM3B/5qNCA | 51780 | jumonji domain containing 1B |

TABLE 1-continued

List of known or predicted human 2OG oxygenases

| Sub-family | Gene Id | Protein description |
|---|---|---|
| JMJD1CA/TRIP8/KIAA1380 | 221037 | jumonji domain containing 1C isoform a |
| JARID2/JMJ | 3720 | JARID2 original Jumonji protein - missing iron binding residue |
| PHD1 | 112398 | HIF prolyl-4-hydroxylase, N-terminal domain disordered |
| PHD2 | 54583 | HIF prolyl-4-hydroxylase, N-terminal MYND |
| PHD3 | 112399 | HIF prolyl-4-hydroxylase, No N-terminal domain |
| ABH1 | 8846 | Alkylated DNA repair protein alkB homolog ABH1 |
| ABH2 | 121642 | similar to hypothetical protein 9530023G02 ABH2 |
| ABH3 | 221120 | hypothetical protein LOC221120 ABH3 |
| ABH4 | 54784 | hypothetical protein LOC54784 ABH4 |
| ABH5 | 54890 | hypothetical protein LOC54890 ABH5 |
| ABH6 | 84964 | probable alpha-ketoglutarate-dependent dioxygenase ABH6 isoform 1 |
| ABH7 | 84266 | probable alpha-ketoglutarate-dependent dioxygenase ABH7 precursor |
| ABH8 | 91801 | 5-methoxycarbonylmethyluridine hydroxylase - wobble position of tRNA, C-terminal Ado-Met-MTase domain |
| FTO | 79068 | Fat mass and Obesity associated DNA demethylase |
| TET1 | 80312 | methylcytosine dioxygenase TET1, CXXC finger 6 |
| TET2 | 54790 | methylcytosine dioxygenase TET2 |
| TET3 | 200424 | methylcytosine dioxygenase TET3 |
| PAHX | 5264 | phytanoyl-CoA hydroxylase precursor |
| PHYHD1 | 254295 | PHYHD1 protein |
| GBBH | 8424 | gamma-butyrobetaine hydroxylase |
| TMLH | 55217 | trimethyllysine hydroxylase, epsilon |

The present invention also provides a method for identifying a selective inhibitor of OGFOD1 (or OGFOD1 homologue), or an inhibitor that is selective for another 2OG oxygenase over OGFOD1. This method comprises: (i) contacting an OGFOD1 substrate, such as RPS23, or fragment thereof comprising a prolyl residue, with an OGFOD1 polypeptide in the presence of a test agent and determining whether the protein or fragment thereof is hydroxylated; (ii) determining whether the test agent modulates activity of a 2OG oxygenase other than OGFOD1, thereby determining whether the test agent selectively modulates OGFOD1 activity or selectively modulates activity of the 2OG oxygenase other than OGFOD1.

Oxygenase activity of the 2OG oxygenase other than OGFOD1 may be determined by contacting a substrate of the 2OG oxygenase with the 2OG oxygenase in the presence of a test agent and determining whether the substrate is hydroxylated or demethylated or otherwise oxidized. In an assay to identify a selective inhibitor of OGFOD1, or another oxygenase, different substrates may be used for OGFOD1 and for the other oxygenase(s).

Alternatively, oxygenase activity of the 2OG oxygenase other than OGFOD1 may be determined in the absence of a prime substrate (i.e., a non-2OG substrate). This enables selective inhibitors to be identified when the prime substrate of one or more of the enzymes being tested is unknown. In this embodiment, generally it will be one or more of the enzymes that it is wished not to inhibit that is an enzyme that has an unknown substrate. The effect of a test agent on activity of an oxygenase may be determined in the absence of a substrate by determining whether or not the test agent affects, for example inhibits or stimulates, the rate of turnover of 2OG by the oxygenase.

Thus, the invention also provides methods for screening for compounds that do not inhibit OGFOD1. Such compounds are of use with respect to developing inhibitors that are selective for 2OG oxygenases other than OGFOD1. Given the similarity of OGFOD1 to other human prolyl-hydroxylases as determined by structural analyses by the inventors (and the finding that the known HIF prolyl hydroxylase inhibitors, including 2-(1-Chloro-4-hydroxyisoquinoline-3-carboxamido)acetic acid, also inhibit OGFOD1) and the interest in developing inhibitors of the HIF prolyl hydroxylases for clinical applications including anaemia and ischemic disease, the discovery that OGFOD1 is a prolyl hydroxylase is of particular interest with respect to developing HIF prolyl-hydroxylase inhibitors that do not inhibit OGFOD1; OGFOD1 inhibitors that do not inhibit the HIF prolyl hydroxylases are also of interest. Standard methods can be used to develop selective inhibitors including examples of developing selective 2OG oxygenase inhibitors, for example, for the HIF prolyl hydroxylases over the HIF asparaginyl hydroxylase. The development of selective inhibitors may employ structural methods that identify differences in the active sites between the enzymes of interest (e.g. between OGFOD1 and the HIF prolyl hydroxylases and or the human collagen prolyl hydroxylases).

The assays of the invention may also be used to identify inhibitors or activators, which are specific for OGFOD1 activity at a particular substrate or residue within a substrate. Such selectivity screens may be used to identify selective inhibitors of OGFOD1 or selective inhibitors of other enzymes, i.e. inhibitors that are more potent inhibitors of OGFOD1 activity than of activity of the other enzyme or inhibitors that are less potent inhibitors of OGFOD1 activity than of activity of the other enzyme. Where the inhibitor is a selective inhibitor of OGFOD1 activity it may have no effect on the activity of the other enzyme or may exhibit only a low level of inhibition, such as less than about 50% inhibition on activity of the other enzyme. Where the inhibitor is a selective inhibitor of the activity of the enzyme other than OGFOD1, it may have no effect on the activity of OGFOD1 or may exhibit only a low level of inhibition, such as less than about 50% inhibition of OGFOD1 activity.

The selectivity screens may be carried out with purified enzymes, partially purified enzymes (such as in crude cell lysates) or in cells, or in animals including humans, and employ the assays methods listed above or other methods.

The invention provides for the use of selective inhibitors in the manufacture of a medicament for the treatment of a condition associated with altered, i.e. enhanced or reduced OGFOD1 oxygenase activity.

The precise format of any of the assay or screening methods of the present invention may be varied by those of skill in the art using routine skill and knowledge. The skilled person is well aware of the need to additionally employ appropriate controlled experiments. The assays of the present invention may involve monitoring for hydroxylation of the substrate, monitoring for the utilisation of substrates and co-substrates, monitoring for the production of the expected products between the enzyme and its substrate. Assay methods of the present invention may also involve screening for the direct interaction between components in the system. Alternatively, assays may be carried out which monitor for downstream effects mediated by the substrate, such as substrate mediated transcription using suitable reporter constructs or by monitoring for the upregulation of genes or alterations in the expression patterns of genes known to be regulated directly or indirectly by the substrate.

Various methods for determining oxygenase activity either directly or indirectly are known in the art. Any suitable method may be used for determining 2OG oxygenase activity of OGFOD1 such as by substrate or co-substrate utilisation, product appearance such as peptide hydroxylation (or demethylation for some 2OG oxygenases) or down-stream effects mediated by hydroxylated products (or demethylated or non-hydroxylated products for some 2OG oxygenases).

The substrate, enzyme and potential inhibitor compound may be incubated together under conditions which, in the absence of inhibitor provide for hydroxylation (or demethylation for some 2OG oxygenases) of the substrate, and the effect of the inhibitor may be determined by determining hydroxylation (or demethylation for some 2OG oxygenases) of the substrate. This may be accomplished by any suitable means. Small polypeptide or polynucleotide substrates may be recovered and subjected to physical analysis, such as mass spectrometry, radiography or chromatography, or to functional analysis. Such methods are known as such in the art and may be practiced using routine skill and knowledge. Determination may be quantitative or qualitative. In both cases, but particularly in the latter, qualitative determination may be carried out in comparison to a suitable control, e.g. a substrate incubated without the potential inhibitor.

In alternative embodiments, reporter constructs may be provided in which promoters mediated by a substrate are provided operably linked to a reporter gene. Any suitable reporter gene could be used, such as for example enzymes which may then be used in colorimetric, fluorimetric, fluorescence resonance or spectrometric assays.

In the assay methods described herein, typically the OGFOD1 polypeptide and the substrate are contacted in the presence of a co-substrate, such as oxygen and/or a 2-oxoacid, such as 2OG. Hydroxylase activity may be determined by determining turnover of one or more of the co-substrates, such as oxygen, 2OG and/or ascorbate. This may be achieved by determining the presence and/or amount of reaction products, such as hydroxylated substrate, carbon dioxide or succinic acid. The amount of product may be determined relative to the amount of substrate. For example, in such embodiments the product measured may be hydroxylated peptide or protein. In the case of protein the extent of hydroxylation may also be determined in cells, e.g. by the use of appropriate antibodies or by mass spectrometry. For example, the extent of hydroxylation may be determined by measuring the amount of hydroxylated peptide/protein, succinate, carbon dioxide, or formaldehyde generated in the reaction, or by monitoring the depletion of 2OG or dioxygen. Methods for monitoring each of these are known in the scientific literature, for example in Myllyharju et al. (1991) EMBO J. 16(6): 1173-1180 or as in Cunliffe et al. (1986) Biochem. J. 240: 617-619. An assay that measures oxygen consumption such as that described by Ehrismann et al. Biochem J. (2007) may be used. In addition, an enzyme activity assay that measures $^{14}CO_2$ generated from the decarboxylation of [$^{14}C$]-2OG coupled to hydroxylation (Kivirikko K I, Myllyla R. Methods Enzymol (1982) may also be used. (Dissolved oxygen electrodes, exemplified by but not limited to a "Clarke-type" electrode or an electrode that uses fluorescence quenching, may be used to follow the consumption of oxygen in an assay mixture.) Use of ion-exchange chromatography to separate [$^{14}C$]-succinic acid and [5-$^{14}C$]-2OG or separation using 2,4-dinitrophenylhydrazine to precipitate [5-$^{14}C$]-2OG may also be used. Measuring conversion of [5-$^{14}C$]-2OG to [$^{14}C$]-succinic acid, Kanelakis K C, Palomino H L, Li L, et al. J Biomol Screen (2009), may also be used. The formation of hydroxylated peptide fragment can be determined directly, e.g. by using either LC/MS analysis, Li D, Hirsila M, Koivunen P, et al. J Biol Chem (2004), or matrix-assisted laser desorption ionization, time-of-flight mass spectrometer or by other assay monitoring hydroxylation. Monitoring the consumption of a reducing agent such as potassium ferrocyanide (replacing ascorbate) FibroGen, Inc. WO2005118836; 2007 may be used. Antibody based methods may also be used by employing an antibody selective for a hydroxylated product or non-hydroxylated substrate. Antibody based methods may be enhanced such that they are more efficient for modulator screening, e.g. by use of homogenous time resolved fluorescence (HTRF) methods which measure the energy transfer between a labelled dye (e.g., via biotin-streptavidin complex) to hydroxyl-proline peptide fragment substrate, and europium, which is tagged to a hydroxyl-proline specific antibody similar to methods described in Dao J H, Kurzeja R J M, Morachis J M, et al. Anal Biochem (2009). Assays that measure displacement of a substrate from OGFOD1 may also be employed—these may employ the use of suitably tagged reagents and antibodies.

The amount of unused 2OG may be determined, e.g., by derivatisation by chemical reagents, exemplified by but not limited to hydrazine derivatives and ortho-phenylene diamine derivatives, to give indicative chromophores or fluorophores that can be quantified and used to indicate the extent of hydroxylation of the substrate. Suitable methods are described in McNeill et al. (2005) (Anal. Biochem. 366:125-131). The fluorescent product of the reaction of ortho-phenylenediamine (OPD) with the α-ketoacid motif of 2OG is 3-(2-Carboxyethyl)-2(1H)-quinoxalinone. This fluorescent product can be readily detected by standard equipment such as that manufactured by for example Molecular Devices, Tecan, BMG Labtechnologies, Jasco and Perkin Elmer and there is extensive precedent demonstrating that the production of fluorescent products can be used in high-throughput screens.

The fluorescent product is generally detected with the excitation filter set as from about 300 nm to about 400 nm, preferably from about 335 nm to about 345 nm, most preferably at about 340 nm. The emission filter is generally at from about 400 to about 450 nm, preferably from about 415 nm to about 425 nm, most preferably at about 420 nm. The nature of the fluorescent product can be tuned by modifying the nature of the derivatisation reagent used. For example, the sensitivity of the method may be increased by using either 1,2-dimethoxy-4,5-diaminobenzene, or 1,2-methylenedioxy-4,5-diaminobenzene.

The precise format of any of the screening or assay methods of the present invention may be varied by those of skill in the art using routine skill and knowledge. The skilled person is well aware of the need to additionally employ appropriate control experiments.

Other components may be added to the assay mixtures. For example, a reducing agent such as ascorbate, a thiol such as dithiothreitol (DDT), β-mercaptoethanol, tris(2-carboxyethyl)phosphine hydrochloride (TCEP), N-acetylcysteine or phenol may be added to the assay to help maintain enzyme structure and/or catalase may be added to destroy any $H_2O_2$ that might be produced. However, the assay will work in the absence of a reducing agent or catalase.

Assays are typically carried out at a temperature of from about 25° C. to about 40° C., for example at a temperature of from about 30° C. to about 39° C., or from about 35° C. to about 38° C. or about 37° C. The pH of the assay mixture is typically between about pH 7 to about pH 9, for example from about pH 7.5 to about pH 8. Suitable buffers, such as Tris or HEPES, may be used to maintain the pH of the assay mixture.

Typically, assays are carried out under normoxic conditions, but may be carried out at oxygen concentrations above or below atmospheric levels. The assay may also be carried out under conditions in which hydroxylation or oxidation is reduced or absent, such as under hypoxic conditions, in order to detect modulation of oxygenase activity by an agent which enhances hydroxylation/oxidation.

Alternatively, the end-point determination may be based on conversion of the substrate or substrate fragments (including synthetic and recombinant peptides or nucleic acids) derived from the polypeptide or nucleic acid substrate into detectable products. Substrates may be modified to facilitate the assays so that they can be rapidly carried out and may be suitable for high throughput screening.

For example, reverse phase HPLC (C-4 octadecylsilane column), as exemplified herein, may be used to separate starting synthetic peptide substrates from the products. Modifications of this assay or alternative assays for oxygenase activity may employ, for example, mass spectrometric, spectroscopic, and/or fluorescence techniques as are well known in the art (Masimirembwa C. et al. Combinatorial Chemistry & High Throughput Screening (2001) 4 (3) 245-263, Owicki J. (2000) J. Biomol. Screen. 5 (5) 297-305, Gershkovich A et al. (1996) J. Biochem. & Biophys. Meths. 33 (3) 135-162, Kraaft G. et al. (1994) Meths. Enzymol. 241 70-86). Fluorescent techniques may employ versions of the substrate modified in such as way as to carry out or optimise spectroscopic or fluorescence assays.

Binding of a molecule, such as an antibody, which discriminates between the hydroxylated and non-hydroxylated forms of a peptide or protein may be assessed using any technique available to those skilled in the art, which may involve determination of the presence of a suitable label.

Assay methods of the present invention may also take the form of an in vivo assay or an assay carried out on ex vivo cells from an animal, such as a mammal (including human) or an insect. The assay may be performed in a cell line such as a yeast or bacterial strain or an insect or mammalian cell line in which the relevant polypeptides or peptides are expressed endogenously or from one or more vectors introduced into the cell. Such assays may employ the use of antibodies specific for hydroxylated or non-hydroxylated forms of OGFOD1 substrates, or may employ proteomic mass spectrometry-based methods based on protease-catalysed digestions or analyses on intact proteins.

The present invention further provides a method for introducing hydroxyprolyl residues into peptides or proteins. As demonstrated in the Examples, OGFOD1 leads to trans-3-prolyl hydroxylation. This is in contrast to other prolyl hydroxylases such as the HIF prolyl hydroxylases such as PHD2 which catalyses trans-4-prolyl hydroxylation. Thus, OGFOD1 polypeptides as described herein are particularly useful for the introduction of trans-3-prolyl hydroxylation. In particular a protein or peptide containing a prolyl residue may be contacted with an OGFOD1 polypeptide as described herein, in order to hydroxylate the prolyl residue. Hydroxylation of prolyl residues may be used for example to increase the stability of the peptide or protein. Hydroxylation of prolyl residues may also be used to modify the activity of the protein. Hydroxylation of prolyl residues may also be used to introduce a glycosylation site into the peptide or protein.

The invention further provides a method for identifying a modulator of protein translation, the method comprising contacting a cell which expresses OGFOD1 with a test agent and determining whether the test agent modulates OGFOD1 regulation of protein translation.

The invention further provides a method for distinguishing between cells that are hypoxic and normoxic. This is because OGFOD1 activity is dependent on oxygen. Thus, the degree of hydroxylation of OGFOD1 substrates, e.g. RPS23, is dependent on oxygen availability. The invention thus further discloses a way of selectively targeting hypoxic cells (such as cancer cells) by use of compounds that preferably inhibit ribosome activity (i.e. translation). Many ribosome inhibitors are available and some are used as antibiotics.

In one embodiment OGFOD1 may be over-expressed in cells. OGFOD1 may be over-expressed in a cell in vitro or in vivo by any suitable method, typically by introducing an expression vector encoding an OGFOD1 polypeptide into the cell. Protein translation (or translation accuracy) may be monitored in the cell over-expressing OGFOD1 and compared to protein translation in a control cell that does not over-express OGFOD1. The cell over-expressing OGFOD1 may be contacted with a test agent and protein translation may be monitored in the presence of the test agent. By comparing translation observed in the presence and absence of the test agent and in the presence and absence of OGFOD1 over-expression, it may determined whether the test agent modulates OGFOD1-mediated regulation of protein translation. Levels of OGFOD1 catalysed hydroxylation in cells may be determined by use of antibodies or by mass spectrometric methods as routinely used in proteomic analyses.

In another embodiment, OGFOD1 may be under-expressed in the cell. OGFOD1 may be under-expressed in a cell in vitro or in vivo by any suitable method, for example by using RNAi technology to knock down the OGFOD1 protein. Protein translation may be monitored in the cell under-expressing OGFOD1 and compared to protein translation in a control cell that does not under-express OGFOD1. The cell under-expressing OGFOD1 may be contacted with a test agent and protein translation may be monitored in the presence of the test agent. By comparing the protein translation observed in the presence and absence of the test agent and in the presence and absence of OGFOD1 under-expression, it may be determined whether the test agent modulates OGFOD1-mediated regulation of protein translation.

Methods for monitoring protein translation rate and or translation accuracy are well known in the art. For example, protein translation may be monitored using a reporter construct. Thus, in a method for identifying a modulator of protein translation according to the invention, the cell may comprise a protein translation reporter construct and the method may comprise determining whether OGFOD1-mediated regulation of protein translation of the reporter construct is modulated by the test agent.

Agents, which may be screened using the assay methods described herein, may be natural or synthetic chemical compounds used in drug screening programmes. Extracts of plants, microbes or other organisms, which contain several, characterised or uncharacterised components may also be used.

Combinatorial library technology (including solid phase synthesis and parallel synthesis methodologies) can provide an efficient way of testing a potentially vast number of different substances for ability to modulate an interaction. Such libraries and their use are known in the art, for all manner of natural products, small molecules and peptides, among others. The use of peptide libraries may be preferred in certain circumstances. Various commercial libraries of compounds are also available. There are computational methods for screening these libraries (processes sometimes referred to as virtual screening) that can identify lead structures for inhibition.

Potential inhibitor compounds (i.e. antagonists) may be polypeptides, peptides, small molecules such as molecules from commercially available libraries, including combinatorial libraries, or the like. The peptide may be a cyclic peptide. Small molecule compounds, which may be used, include 2OG analogues, or substrate analogues, which inhibit the action of the enzyme. Small molecule compounds, and other types of compound, that may be used include all known 2OG oxygenase inhibitors such as those already known to inhibit HIF hydroxylases (see for example WO03/080566, WO02/074981, WO2007/146483, WO2007136990, WO2007/103905, WO2007/150011, US2007/0299086, US2007/0249605 and US2007/0213335), procollagen prolyl hydroxylases, and histone demethylases (for which the output of high throughput screening data is publicly available—see e.g. King et al. PLoS ONE 5(11): e15535, doi:10.1371/journal.pone.0015535 and associated material).

Potential promoting agents may be screened from a wide variety of sources, particularly from libraries of small compounds, which may be commercially available. Candidate compounds to be screened, may include 2OG analogues, compounds that chelate iron or known families of 2OG oxygenases inhibitors.

Since naturally occurring compounds, including TCA cycle intermediates such as fumarate and succinate, are known inhibitors of 2OG oxygenases they may inhibit OGFOD1, possibly in a manner that is of physiological relevance, including in some cancers where fumarate is known to be upregulated as a consequence of the Warburg effect.

A test compound which increases, potentiates, stimulates, disrupts, reduces, interferes with or wholly or partially abolishes hydroxylation of the substrate and which may thereby modulate activity, may be identified and/or obtained using the assay methods described herein.

Agents which increase or potentiate hydroxylation (i.e. agonists), may be identified and/or obtained under conditions which, in the absence of a positively-testing agent, limit or prevent hydroxylation. Such agents may be used to potentiate, increase, enhance or stimulate the oxygenase activity of OGFOD1.

In various aspects, the present invention provides an agent or compound identified by a screening method of the invention to be a modulator of OGFOD1 oxygenase activity e.g. a substance which inhibits or reduces, increases or potentiates the activity of OGFOD1.

The test agent may compete with 2OG or an OGFOD1 substrate at the OGFOD1 active site and/or binds to the active site of OGFOD1 or to metal at the OGFOD1 active site. The test agent may comprise a metal ion such as, but not limited to, manganese, cobalt, zinc or nickel ions as inhibitors or iron (II), iron (III) as activators. Alternatively, the mode of inhibition may be via competition with the substrate or by an allosteric interaction.

The test agent may be a reducing agent. Reducing agents typically act as activators of 2OG oxygenase activity, typically in vitro. An activator of oxygenase activity may be any species that increases oxygenase activity of an OGFOD1 polypeptide either in vitro or in vivo. Reducing agents that may be used include ascorbate and analogues of ascorbate and reducing agents of the thiol chemical families, such as dithiothreitol or phosphine (e.g. triscarboxyethylphosphine).

Following identification of a modulator, the substance may be purified and/or investigated further (e.g. modified) and/or manufactured. A modulator may be used to obtain peptidyl or non-peptidyl mimetics, e.g. by methods well known to those skilled in the art and discussed herein. A modulator may be modified, for example to increase selectively, as described herein. It may be used in a therapeutic context as discussed below.

For therapeutic treatment, the modulator may be alone or used in combination with any other therapeutically active substance or treatment including but not limited to metal ions or succinate or fumarate (Chen et al. J Biol Chem 2010).

The compounds which are acids can be present in the form of salts, such as sodium salts. The compounds may also be present in the form of derivatives such as the dimethyl ester, diethyl ester, monoethyl ester or di- or mono-amide, or other prodrug form rendering suitable pharmacokinetic properties. In certain instances these derivatives may be preferred, for example when inhibition of the enzyme within a cell of an organism is required.

Compounds which modulate 2OG oxygenases may be useful as agents of the invention, for example, in the treatment of disorders as described herein, or may be used as test substances in an assay of the invention. The test compound may be known to act as an inhibitor of a 2OG oxygenase other than OGFOD1. For example, the test agent may be a described inhibitor of procollagen prolyl hydroxylase, hypoxia inducible factor, prolyl and asparaginyl hydroxylases, collagen prolyl hydroxylase, gibberellin C-20 oxidase, a nucleic acid demethylase such as AlkB or a human AlkB homologue, a protein demethylase, such as a tri-, di-, mono-methyl lysine or arginine residue demethylase, another human or animal 2OG oxygenase involved in metabolism or regulation, or a plant 2OG hydroxylase. Many inhibitors of 2OG oxygenases are known in particular for human prolyl hydroxylases and histone demethylases. N-Oxaloglycine and its derivatives are one such examples, but there are many others, which one of skilled in the art of oxygenases may test as OGFOD1 inhibitors, glycine or alanine derivatives and 2-oxoacid analogues may also be used.

Compounds which modulate 2OG oxygenases, and families of such compounds, are known in the art, for example in Aoyagi et al. (2002) Hepatology Research 23 (1): 1-6, Aoyagi et al. (2003) Free Radical Biology and Medicine 35:410 Suppl. 1, Philipp et al. (2002) Circulation 106 (19): 1344 Suppl. S, Ivan et al. (2002) PNAS USA 99 (21): 13459-13464, Nwogu et al. (2001) Circulation 104 (18): 2216-2221, Myllyharju and Kivirikko (2001) Ann Med 33 (1): 7-21, Ohta et al. (1984) Chemical and Pharm Bulletin 32 (11): 4350-4359, Franklin et al. (2001) Biochem J. 353: 333-338, Franklin (1997) Int J. Biochem Cell Biol 29 (1): 79-89, Dowell et al. (1993) Eur J Med Chem 28 (6): 513-516, Baader et al. (1994) Biochem J. 300: 525-530, Baader et al. (1994) Eur J Clin Chem and Clin Biol 32 (7): 515-520, Bickel et al. (1998) Hepatology 28 (2): 404-411, Bickel et al. (1991) J. Hepatology 13: S26-S34 Suppl. 3, U.S. Pat. No. 6,200,974, U.S. Pat.

No. 5,916,898, US Patent Applications 2003-0176317, 2003-0153503 and 2004-0053977, WO 02/074981, WO 03/080566, WO 04/035812, Cunliffe et al. (1992) J. Med. Chem. 35:2652-2658, Higashide et al. (1995) J. Antibiotics 38:285-295, Cunliffe et al. (1986) Biochem. J. 239(2):311-315, Franklin et al. (1989) Biochem. J. 261(1):127-130, Friedman et al. (2000) PNAS USA 97(9):4736-4741, Wu et al. (1999) J. Am. Chem. Soc. 121(3): 587-588, DE-A-3818850, Wang et al. (2001) Biochemistry US:15676-15683 and Lerner et al. (2001) Angew Chem. Int. Edit. 40:4040-4041. Rose et al. J Med Chem (2008), Rose et al. J Med Chem (2010), Conjeo-Garcia et al. Bioorg Med Chem Lett. (2010), Banjeri et al. Chem Commun (2005), Hewitson et al. J Biol Chem (2007), McDonough et al. J Am Chem Soc (2005), Mecinovic et al. Bioorg Med Chem Lett (2009), Lienard et al. Chem Commun (2008), Hamada et al. J Med Chem (2010), Simkhovich et al. Biochem Pharmacol (1988).

Suitable compounds are disclosed in WO03/080566, WO02/074981, WO2007/146483, WO2007136990, WO2007/103905, WO2007/150011, US2007/0299086, US2007/0249605, WO2009/074498 and US2007/0213335. Other suitable compounds include inhibitors of HIF hydroxylase. HIF hydroxylase inhibitors are disclosed in United States Patent Application Publication Nos: 20070042937, 20060276477, 20060270699, 20060258702, 20060258660, 20060251638, 20060183695, 20060178317 and 20060178316 and in International Patent Application Publication Nos: WO2007/070359, WO2008/002576, WO2007/103905, WO2005118836, WO2003049686, WO2003053997, US20060276477, US20070292433, US20070293575, WO2004108121. US20060251638, WO2004052285, WO2005011696, WO2005034929, WO2004052284, WO2006099610, WO2007097929, WO2009075824, WO2009075826, WO2006138511, WO2009058403, WO2009075826, WO2006138511, WO2009058403, WO9921860, WO2006094292, WO2007090068, WO2007115315, WO2009073669, WO2009089547, WO2009100250, WO2010056767, WO2010022240, WO2004052313, WO2007038571, WO2007103905, WO2007136990, WO2009039323, WO2009039321, WO2009039322, WO2010022307, WO2009070644, WO2009073497, WO2009134850, WO2009134847, WO2007150011, US20080171756, WO2008089052, WO2009158315, WO2010025087, WO2009049112, WO2009086044, WO2010022308, WO2010059549, WO2010059552, WO2010059555, WO2007070359, WO2008076425, WO2008137084, WO2008076427, WO2008130508, WO2008130600, WO2008137060, WO2006114213, WO2008067874, DE102007044032, WO2008049538, DE102007048447, DE102007049157, WO2008067871, US20090269420, WO2008130527, WO2009108496, WO2009108497, WO2009108499, WO2008144266, WO2009137291, WO2009117269, WO2009134750, WO2009134754, US20080124740, US20070299086, WO2009037570, WO2010018458, WO2009016812.

Other suitable compounds include compounds of formula (I):

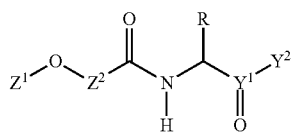

(I)

wherein
Y² is selected from —OR' and —NR'R" wherein R' is hydrogen, or unsubstituted $C_{1-4}$ alkyl and R" is hydrogen, hydroxy or unsubstituted $C_{1-4}$ alkyl;
Y¹ is selected from —C—, —S— and —S(O)—;
Z² is selected from —C(O)— and —NR"— wherein R" is selected from hydrogen, hydroxy or unsubstituted $C_{1-4}$ alkyl;
Z¹ is selected from hydrogen and unsubstituted $C_{1-4}$ alkyl; and
R is a side chain of a naturally occurring amino acid.

Preferably Y¹ is —C— and Y² is —OH or —NH₂. Most preferably Y¹ is —C— and Y² is —OH.

Preferably Z² is —C(O)— or —NR"— wherein R" is hydrogen, methyl or ethyl. More preferably Z² is —C(O)— or —NH—. Preferably Z¹ is hydrogen, methyl or ethyl, more preferably hydrogen. Most preferably Z² is —C(O)— and Z¹ is hydrogen, methyl or ethyl.

Preferably R is a side chain of alanine, valine, leucine or phenylalanine Preferably R is a side chain of valine, leucine or phenylalanine. More preferably R is a side chain of phenylalanine, i.e. —CH₂Ph.

L-stereoisomers or D-stereoisomers of these compounds may be used.

An exemplary synthetic scheme used to obtain test compounds of formula (I) is shown below in Scheme 1. Here an amino acid is reacted with an oxalyl chloride in order to produce a compound of formula (I). In this scheme the amino acid used is phenylalanine, although it will be apparent that the same general reaction will occur with other amino acids. The first reaction yields a protected compound of the invention (the dimethyl ester form). The diacid form is easily generated through reaction with aqueous sodium hydroxide.

Scheme 1:

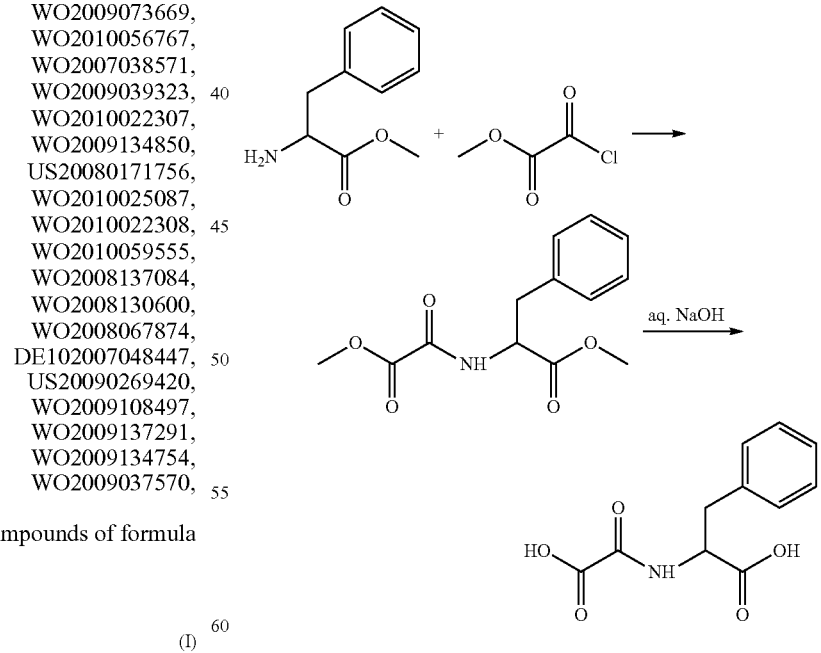

Compounds in which X is O or S or Z is other than —CO—CO—OH may by synthesised as described in Mole et al. (2003) Bioorg. Med. Chem. Lett. 13, 2677-2680 and Cunliffe et al. J. Med. Chem. (1992) 35 2652-2658.

The inventors have shown that the following compounds are inhibitory of OGFOD1 prolyl hydroxylase activity: an N-oxalyl amino acid such as N-oxalylglycine (NOG) or a derivative thereof, a glycine or alanine derivative, a 2-oxoacid analogue, a catechol or Catechol derivative such as gallic acid, or pyridine-2,4-dicarboxylic acid or FG2216.

The present invention provides the use of an inhibitor or activator of 2OG oxygenase activity to modulate prolyl hydroxylation of ribosomal protein by OGFOD1.

A compound, substance or agent which is found to have the ability to affect the oxygenase (prolyl hydroxylase) activity of OGFOD1 has therapeutic and other potential in a number of contexts, as discussed.

The modulator of OGFOD1 prolyl hydroxylase activity, may be a known inhibitor of a 2OG oxygenase, such as an N-oxalyl amino acid such as N-oxalylglycine (NOG) or a derivative thereof, a glycine or alanine derivative, a 2-oxoacid analogue, a bipyridyl derivative, a diacylhydrazine, a catechol or catechol derivative such as gallic acid, or pyridine-2,4-dicarboxylic acid or FG2216. The inhibitor may be a selective inhibitor of OGFOD1 activity compared to other 2OG oxygenases.

An agent identified using one or more primary screens (e.g. in a cell-free system) as having ability to modulate oxygenase activity may be assessed further using one or more secondary screens.

Generally, an agent, compound or substance which is a modulator according to the present invention is provided in an isolated and/or purified form, i.e. substantially pure. This may include being in a composition where it represents at least about 90% active ingredient, more preferably at least about 95%, more preferably at least about 98%. Any such composition may, however, include inert carrier materials or other pharmaceutically and physiologically acceptable excipients, such as those required for correct delivery, release and/or stabilisation of the active agent.

The invention further provides compounds obtained by assay methods of the present invention, and compositions comprising said compounds, such as pharmaceutical compositions wherein the compound is in a mixture with a pharmaceutically acceptable carrier or diluent. Examples of suitable carriers or diluents are given in, for example, "Harrison's Principles of Internal Medicine". The carrier may be liquid, e.g. saline, ethanol, glycerol and mixtures thereof, or solid, e.g. in the form of a tablet, or in a semi-solid form such as a gel formulated as a depot formulation or in a transdermally administrable vehicle, such as a transdermal patch.

The invention further provides a method of treatment which includes administering to a patient an agent which modulates OGFOD1 oxygenase activity. Such agents may include inhibitors of OGFOD1 oxygenase activity. In view of the role that OGFOD1 may play in translational accuracy, such agents may be used for the treatment of diseases caused by premature stop-codons, such as cystic fibrosis (CF), haemophilia, retinitis pigmentosa and Duchene muscular dystrophy (DMD). Such agents may also be used to combat retroviruses, such as HIV.

A therapeutically effective amount of an agent is typically administered to a subject in need thereof.

In various further aspects, the present invention thus provides a pharmaceutical composition, medicament, drug or other composition for such a purpose, the composition comprising one or more agents, compounds or substances as described herein, including inhibitors of OGFOD1 oxygenase activity, the use of such a composition in a method of medical treatment, a method comprising administration of such a composition to a patient, e.g. for treatment (which may include preventative treatment) of a medical condition as described above, use of such an agent compound or substance in the manufacture of a composition, medicament or drug for administration for any such purpose, e.g. for treatment of a condition as described herein, and a method of making a pharmaceutical composition comprising admixing such an agent, compound or substance with a pharmaceutically acceptable excipient, vehicle or carrier, and optionally other ingredients. Typically such agents are useful as anti-microbial agents, for example for use as antibiotics to treat bacterial infection in an individual.

In one embodiment the method for providing a pharmaceutical composition may typically comprise:

(a) identifying an agent by an assay method of the invention; and (b) formulating the agent thus identified with a pharmaceutically acceptable excipient.

The pharmaceutical compositions of the invention may comprise an agent, polypeptide, polynucleotide, vector or antibody according to the invention and a pharmaceutically acceptable excipient.

Whatever the agent used in a method of medical treatment of the present invention, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

An agent or composition may be administered alone or in combination with other treatments, either simultaneously or sequentially dependent upon the condition to be treated, e.g. as described above.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. In particular they may include a pharmaceutically acceptable excipient. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride Injection, Ringer's Injection, Lactated Ringer's Injection. Preservatives, stabilisers, buffers, antioxidants and/or other additives may be included, as required.

Liposomes, particularly cationic liposomes, may be used in carrier formulations. Examples of techniques and protocols mentioned above can be found in Remington's Pharmaceutical Sciences, 16th edition, Osol, A. (ed), 1980.

The substance or composition may be administered in a localised manner to a particular site or may be delivered in a manner in which it targets particular cells or tissues, for example using intra-arterial stent based delivery.

Targeting therapies may be used to deliver the active substance more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

All the documents cited herein are incorporated herein by reference.

The following Examples illustrate the invention.

EXAMPLES

1: Experimental Procedures

Cloning of OGFOD1

The cDNA sequence encoding full-length human OGFOD1 (SEQ ID NO:1) was amplified from an IMAGE clone and inserted into the NheI and EcoRI restriction sites of the pET-28a expression vector (Novagen). This plasmid is referred to as hsOGFOD1-FL-pET-28a.

Representative Procedure for Cloning of the C-terminal Domain of OGFOD1

The cDNA sequence encoding the C-terminal domain of human OGFOD1 was amplified from the full-length construct using commercially synthesized oligonucleotide primers (Sigma-Genosys) OGFOD1_Q261_F (5'-ATACCATG-GCTCAAGATCATGAGATTT-3') and OGFOD1_Q261_R (sequence: 5'-AAACTCGAGTTCATAATAGATGAAT-GAAA-3'). These primers are set out in SEQ ID NOs: 8 and 9.

Conditions:

| Template DNA: | 1 ng |
|---|---|
| OGFOD1_Q261_F (10 μM) | 1 μL |
| OGFOD1_Q261_R (10 μM) | 1 μL |
| dNTPs (10 mM each) | 0.4 μL |
| 10x Polymerase buffer | 2.5 μL |
| Pfu Turbo DNA polymerase | 1 μL |
| H$_2$O | added to a total volume of 25 μL. |

Thermocycler Setup:

| 95° C. | 2 min | |
|---|---|---|
| 95° C. | 30 sec | |
| 58° C. | 30 sec | 30 cycles |
| 72° C. | 1.6 min | |
| 72° C. | 10 min | |

The entire PCR reaction was digested with NcoI (New England Biolabs) and XhoI (Promega) restriction enzymes in NEB buffer 4 (New England Biolabs) including 1×BSA, at 37° C. for 1 hour. The digested PCR product was run on a 1% agarose gel, the band corresponding to the desired product was excised and DNA was extracted from the gel slice with a QIAquick gel extraction kit (QIAGEN). The extracted DNA was ligated into similarly restricted and purified pET-21d vector (Novagen) using T4 DNA ligase (New England Biolabs) at room temperature for 15 min.

| Vector | 50 ng |
|---|---|
| PCR product | 28 ng |
| 10x T4 ligase buffer | 2 μL |
| T4 DNA ligase (400,000 units/mL) | 1 μL |
| H$_2$O | added to a total volume of 20 μL |

2 μL of this reaction mixture was transformed into 50 μL E. Coli XL10 Gold® cells (Agilent) according to the manufacturer's instructions. Cells were grown on an LB plate containing 30 μg/mL kanamycin at 37° C. overnight.

On the following day, 3 colonies were picked off the plate, resuspended in 100 mL 2TY medium containing 30 μg/mL kanamycin each and incubated in an environmental shaker at 37° C. overnight.

Plasmids were isolated from these liquid cultures on the following day using a QIAprep Spin Miniprep Kit (QIAGEN) and samples subjected to a control restriction digest with NcoI and XhoI at 37° C. for 15 min:

| Miniprep DNA | 1 μg |
|---|---|
| NcoI | 0.5 μL |
| XhoI | 0.5 μL |
| 10x NEB 4 buffer | 2 μL |
| 100x BSA | 0.2 μL |
| H$_2$O | added to a total volume of 20 μL |

Samples were analyzed by 1% agarose gel and found to contain an insert of expected size. Samples were submitted for external sequencing (GeneService) and shown to contain the desired insert. This plasmid is referred to as hsOGFOD1-Q261-pET-21d.

Site-Directed Mutagenesis of OGFOD1

Site-directed mutagenesis was performed to elucidate the functional role of specific active site residues of the OGFOD1 protein. Expression constructs for the H155A and D157A alanine variants of OGFOD1 were prepared by Quikchange site-directed mutagenesis of the hsOGFOD1-FL-pET-28a construct using primer pairs hsOGF_H155A_F (5'-ctgatgc-cctgctgtgcgcggatgatgagctggaagg-3') and hsOGF_H155A_R (5'-ccttccagctcatcatccgcgcacagcagggcatcag-3'), as well as hsOGF_D157A_F (5'-tgctgtgccatgatgcggagctggaagggcgc-3') and hsOGF_D157A_R (5'-gcgcccttccagctccgcatcatggca-cagca-3'). These primers are set out in SEQ ID NOs: 15, 12, 14 and 15. QuikChange site-directed mutagenesis was performed in a 20 μL reaction volume, using Pfu Turbo polymerase according to the manufacturer's instructions. PCR amplification was conducted using an initial denaturation of 30 s at 95° C., followed by 18 amplification cycles, each consisting of a 30 s denaturation at 95° C., a 1 min annealing step at 55° C., and a 7 min extension step at 68° C. Final extension was performed for 10 min at 68° C. PCR reactions were then treated with 1 μL DpnI restriction enzyme (New England Biolabs) for 2 h at 37° C. to digest methylated parental template DNA, transformed into XL10-Gold® ultra-competent cells (Agilent) and plated on selective LB agar plates. Starter cultures of colonies were prepared, DNA was extracted by miniprep, and mutagenesis was verified by DNA sequencing.

Production and Purification of OGFOD1

Larger-scale production was conducted using a BL21 (DE3) strain carrying the hsOGFOD1-FL-pET-28a construct in PowerBroth fermentation medium (Athena Environmental Sciences Inc, Baltimore, Md. 21227). Cells were grown to an OD$_{600}$ ~1.5 and induced with 2 mM IPTG at 28° C. for 22 hrs. Fast Protein Liquid Chromatography (FPLC) for protein purification was carried out using Äkta™ FPLC systems (GE Healthcare) at 4° C. Buffers were freshly prepared in Milli-Q water. Samples up to 10 mL were loaded using sample loops or a Superloop™ (GE Healthcare) with larger samples being loaded from Schott bottles or measuring cylinders using the FPLC pump. Sample fractions were collected using a Frac-920 fraction collector. Purification of proteins was monitored using UV absorbance at 280 nm with a UPC-900 monitor on the FPLC, by detection of protein in elution fractions using Bradford reagent, and by SDS-PAGE analysis of collected fractions. All columns were cleaned after each use according to the manufacturers' instructions.

IMAC Buffer Compositions

IMAC binding buffer: 20 mM Tris-Cl, 500 mM NaCl, 5 mM imidazole, pH 7.9

IMAC wash buffer: 20 mM Tris-Cl, 500 mM NaCl, 60 mM imidazole, pH 7.9

IMAC elution buffer: 20 mM Tris-Cl, 500 mM NaCl, 1 M imidazole, pH 7.9

IMAC strip buffer: 20 mM Tris-Cl, 500 mM NaCl, 100 mM EDTA, pH 7.9

IMAC charge buffer: 50 mM $NiSO_4$

Cell pellets were frozen at −80° C. and mechanically disintegrated into small pieces. Then, ice-cold IMAC binding buffer (approx. 3 mL/g) containing Protease inhibitor cocktail (Roche complete EDTA-free, 1 tablet/50 mL) was added. The resultant suspension was stirred at 4° C. until homogeneous. Subsequently, lysozyme (from chicken egg white) was added (approx. 10 mg/100 mL) to improve protein extraction efficiency, followed by DNAse I (from bovine pancreas, Roche). Stirring was continued at 4° C. for 30 min to maximise lysis efficiency. Subsequently, the suspension was sonicated on ice using a Sonics VibraCell VCX-500 sonicator (13 mm probe at 60% intensity) for 10-15 minutes, using pulses of 5 s, separated by 5 s breaks. The resultant lysate was clarified by centrifugation (20.000 rpm for 30 min at 4° C.) and filtered through a 0.20 μm filter prior to chromatographic purification.

All purification procedures were carried out at 4° C. Clarified cell lysates were loaded at a flow rate of 1 mL/min onto the FPLC column. Subsequently, columns were flushed with ~4 CV binding buffer to ensure complete binding, followed by ~10-20 CV wash buffer. In general, washing was continued until a stable baseline was reached. In initial purification attempts, linear gradient elution was employed to maximise separation of target protein from potential contaminants, using 0-40% elution buffer in washing buffer over 4 CV, followed by 40-100% elution buffer in washing buffer over another 4 CV. After optimal conditions had been determined, step gradient elution (0-100% elution buffer, 0 CV) was used to minimise buffer consumption and elution volume, thus maximising the concentration of eluted protein. Protein-containing fractions were identified by UV absorbance, visual inspection, treatment with Bradford reagent, conductance monitoring, and SDS-PAGE analysis.

Eluted proteins were desalted into 50 mM Tris-Cl pH 8.0, 1 mM DTT using PD-10 desalting columns. The loading volume was 2.5 mL/column, elution volume 3.5 mL/column. Desalted protein fractions were combined and concentrated using centrifugal concentrators (Amicon, molecular weight cutoff 30 kDa), according to the manufacturer's instructions. Final protein concentrations were determined by UV absorbance, using a NanoDrop spectrophotometer and desalting buffer as reference solution. Extinction coefficients were calculated using ProtParam. Desalted and concentrated proteins were split into aliquots and snap-frozen prior to storage at −80° C.

Size exclusion chromatography was performed using 100 mM or 500 mM NaCl, and 100 mM Tris-Cl pH 7.5, optionally supplemented with DTT (1 mM final concentration). Chromatographic media used were Superdex 200 resin (CV 300 mL) and Superdex 75 resin (CV 300 mL). Chromatography was accomplished using a flow rate of 1 mL/min at 4° C., and the eluate was collected in 5 mL fractions.

SDS-PAGE Analysis

For SDS-PAGE analysis, samples were added to 6×SDS-loading buffer (containing 300 mM Tris-Cl pH 6.8, 0.01% w/v bromophenol blue, 15% v/v glycerol, 6% w/v SDS and 100 μL beta-mercaptoethanol) and heated to 90-110° C. for 3-5 min prior to loading on the gel. Polyacrylamide gels were run for 40-120 min at 120-200 V using a BioRad Mini-PROTEAN II system. Gels were stained for 15-20 min in staining solution (0.5% w/v Coomassie Blue R-250, 50% v/v methanol, 10% v/v acetic acid) and subsequently washed with destaining solution (either 10% v/v methanol 10% v/v acetic acid, or 40% v/v ethanol, 10% v/v acetic acid). SDS-PAGE stacking gel buffer contained 125 mM Tris-Cl, 0.2% w/v sodium dodecylsulfate, pH 6.8. SDS-PAGE separating gel buffer contained 375 mM Tris-Cl, 0.2% w/v sodium dodecylsulfate, pH 8.8.

2OG Turnover Assays

Constructs of OGFOD1 encoding full-length protein or its C-terminal domain were tested for enzymatic activity using a 2OG turnover assay (Kivirikko and Myllyla (1982) Methods in Enzymology 82: 4412-4421). OGFOD1 was incubated with all necessary cofactors, in various buffers lacking a specific reagent ($Fe^{2+}$ or ascorbate) and in the presence of pyridine 2,4-dicarboxylic acid (2,4-PDCA), a generic $Fe^{2+}$-2OG oxygenase inhibitor at a concentration of 1 mM. In addition to $Fe^{2+}$ (added in the form of $(NH_4)_2Fe(II)(SO_4)_2$) and 2OG, dithiothreitol (DTT), sodium ascorbate and catalase were added to the reaction mixture. DTT is a reducing agent that helps to prevent oxidation of $Fe^{2+}$. Ascorbate was added because of its potential to increase 2OG turnover of some 2OG oxygenases, such as the hypoxia inducible factor prolyl hydroxylases and the collagen prolyl-4-hydroxylases. Catalase was added to decompose any hydrogen peroxide generated during uncoupled turnover.

Assay Components:

8-10 μM OGFOD1

288 μM 2OG 3.7 μM $^{14}C$-2OG

100 μM $(NH_4)_2Fe(SO_4)_2$ 4 mM Ascorbate 1 mM DTT (optional)

These were diluted to a total volume of 100 μl with 50 mM Tris-Cl buffer, pH 7.5. All reagents were mixed and pipetted into a 5 mL plastic screw cap tube. The OGFOD1 protein was added to the tube as a separate drop. A 500 μL, Eppendorf tube containing 200 μL, hyamine hydroxide (Fisher Scientific, $CO_2$ trapping agent) was added to each tube and tubes were closed with a rubber septum. After incubation in an environmental shaker at 37° C. for 15-20 min, 200 μL, methanol was added to the contents and the tubes were put on ice for 30 min to quench the reaction. The Eppendorf tubes containing the hyamine hydroxide were transferred to scintillation vials, mixed with 5 mL OptiPhase Liquid Scintillation Cocktail (Fisher Scientific) and total $^{14}C$ counts quantified using a Beckman LS6500 Multi-Purpose Scintillation Counter. Conversion of 2OG was calculated from the percentage of 1-[$^{14}C$]-2OG that had been converted into gaseous $^{14}CO_2$.

Thermal Stability Shift Assays

Assays were conducted in 50 mM HEPES buffer, 150 mM NaCl, pH 7.5. A stock solution of $MnCl_2$ (500 mM) in 20 mM HCl was prepared, and diluted to 5 mM with water. A master mix containing 2.085 mL buffer, 21 µL MnCl$_2$ (5 mM, 50 µM final), 21 µL hsOGFOD1_FL (100 µM, 1 µM final), and 2.1 µL SYPRO Orange dye was prepared. The screen was conducted using stock solutions of compounds (400 µlM in DMSO) at a final concentration of 20 µM, by mixing 1 µL compound stock solution with 19 µL assay master mix. Incubations were performed in a white 96-well RT-PCR plate and subjected to thermal cycling as per an established protocol. Data was analysed in Microsoft Excel and GraphPad Prism.

Amino Acid Analysis

To determine the stereochemistry of OGFOD1-mediated RPS23 prolyl hydroxylation, synthetically prepared peptide 20mer was incubated with recombinant OGFOD1 under conditions allowing for >80% hydroxylation. OGFOD1 was precipitated from the reaction mixture, and the hydroxylated peptide was desalted using a reversed-phase spin column and lyophilised. Samples were processed and analyzed by Anthony Willis (Amino acid analysis facility, Biochemistry Department, University of Oxford) using acid hydrolysis followed by pre-column derivatization and HPLC separation.

Preparation of Fmoc-Protected Amino Acids for Peptide Synthesis

Fmoc-cis-4-hydroxy-(L)-proline, Fmoc-cis-3-hydroxy-(L)-proline and Fmoc-trans-3-hydroxy-(L)-proline were prepared by acylation of the corresponding free amino acids with 9-fluorenylmethyloxycarbonyl chloride (Fmoc-Cl), using established synthetic procedures (Taylor, Hardre et al. 2005). Cis-3-hydroxy-(L)-proline was purchased from Chem-Impex International Inc (Wood Dale, Ill., USA). Trans-3-hydroxy-(L)-proline and trans-4-hydroxy-(L)-proline were purchased from Acros Organics. Cis-4-hydroxy-(L)-proline was purchased from Bachem.

Fmoc-trans-3-hydroxy-(L)-proline

To a stirred and cooled suspension of trans-3-hydroxy-(L)-proline (2.00 g, 15.3 mmol, 1.00 eq.) in 1,4-dioxane (110 mL) and aq. NaHCO$_3$ (5% w/v, 55 mL) was added slowly a solution of Fmoc-Cl (4.02 g, 15.56 mmol, 1.02 eq.) in dioxane (50 mL). The reaction mixture was kept at 4° C. for 4 h, allowed to warm to room temperature, and stirred for another 6 h to afford a clear, colorless solution. Most of the dioxane was evaporated in vacuo (45° C. bath temperature), and the resultant solution was extracted with diethyl ether (2×100 mL) to remove excess Fmoc-Cl. The aqueous layer was acidified to pH 2-3 with 1 M HCl to afford a cloudy solution, which was extracted with EtOAc (4×100 mL). The combined organic layers were dried (MgSO$_4$), filtered, evaporated in vacuo and co-evaporated twice with CH$_2$Cl$_2$. Drying under vacuum afforded the product as an off-white, microcrystalline solid (3.10 g, expected 5.39 g, yield 58%). Spectroscopic data were in agreement with the literature (Taylor, Hardre et al. 2005).

Fmoc-cis-4-hydroxy-(L)-proline

Prepared as described (Taylor, Hardre et al. 2005). From 270 mg starting material, the product was obtained as a light pink powder (514 mg, 71%). $^1$H NMR (400 MHz, DMSO-d$_6$) $\delta_H$ 1.88 (dt, J=13.0, 4.0 Hz, 1H), 1.94-2.04 (m, 1H), 2.26-2.44 (m, 1H), 3.21 (ddd, J=10.5, 7.0, 3.0 Hz, 1H), 3.37 (brs, 1H), 3.48-3.62 (m, 1H), 4.12-4.40 (m, 5H), 7.28-7.38 (m, 2H), 7.38-7.48 (m, 2H), 7.59-7.73 (m, 2H), 7.89 (t, J=7.0 Hz, 2H), 12.52 (brs, 1H);

Fmoc-cis-3-hydroxy-(L)-proline

Prepared as described for the cis-4-hydroxy regioisomer (Taylor, Hardre et al. 2005). From 800 mg starting material, the product was obtained as a light pink powder (1.60 g, 74%).

$^1$H NMR (400 MHz, DMSO-d$_6$) $\delta_H$ 1.79-1.94 (m, 1H), 1.94-2.07 (m, 1H), 3.32-3.54 (m, 3H), 4.11-4.33 (m, 4H), 4.41-4.59 (m, 1H), 7.27-7.37 (m, 2H), 7.37-7.47 (m, 2H), 7.61-7.71 (m, 2H), 7.84-7.93 (m, 2H), 12.46 (brs, 1H);

Synthesis and Purification of Peptides

Peptides were synthesised using a CS-Bio 336S, a CS-Bio 336X and a Multipep peptide synthesis machine (Intavis AG Bioanalytical Instruments, Germany). Standard amino acids were purchased from CS-Bio in their Fmoc-N-α-protected form. Fmoc-trans-4-hydroxy-(L)-proline was obtained from Merck. Fmoc-cis-4-hydroxy-(L)-proline, Fmoc-cis-3-hydroxy-(L)-proline and Fmoc-trans-3-hydroxy-(L)-proline were prepared as described in the synthetic section. Peptide synthesis was carried out in dimethylformamide (DMF) using diisopropylcarbodiimide (DIC) and 1-hydroxybenzotriazole (HOBt) as activating reagents, and piperidine as Fmoc deprotection reagent. DIC was used as 0.5 M solution in DMSO, and HOBt as a 0.5 M solution in DMF. Typically, synthesis was carried out on a 0.1 mmol scale, using MBHA Rink Amide resin (loading 0.45 mmol/g), 1 mmol of protected amino acids (10× molar excess), and 1 mmol of activating reagents (DIC, HOBt). Parallel peptide synthesis for screening was performed on Tentagel S-RAM resin. Amino acids were pre-activated by addition of DIC/HOBt for 30 min prior to addition to the resin. After addition to the resin, the activated amino acid was allowed to react with the resin/growing peptide chain for 2 h, prior to removal and washing of the resin. Fmoc deprotection was performed using 20% piperidine, 20% DMSO in 60% DMF, followed by extensive washing of the resin, and addition of the next amino acid.

After synthesis was completed, the resin was washed with DMF (5 times) under nitrogen (to prevent oxidation of oxygen-sensitive residues). Subsequently, the resin was washed with glacial acetic acid to neutralise trace amines present in DMF, with dichloromethane (5 times) to remove DMF, and finally with methanol to shrink the resin. The resin was immediately placed in a vacuum desiccator and dried overnight.

For biotinylation of peptides, the washed resin (0.1 mmol) was resuspended in N-methylpyrrolidone (NMP, 5 mL) containing Biotin-ONp (120 mg) and catalytic amounts of HOBt and incubated overnight with gentle shaking. The resin was then washed and dried as above.

Cleavage of the peptide from the resin was achieved using Reagent B (88% TFA, 5% water, 5% phenol, 2% triisopropylsilane or 2% triethylsilane). Briefly, the resin (0.1 mmol) was incubated with 5 mL cleavage cocktail under a blanket of nitrogen for 2-4 h, with occasional mixing. Resin was removed by filtration through a hydrophilic SPE separation cartridge (Applied Separations). The cleavage cocktail, containing the deprotected peptide, was immediately concentrated to <0.5 mL under a stream of nitrogen. The peptide was precipitated by addition of ice-cold diethylether (14 mL). The suspension was sonicated briefly and the solid peptide collected by centrifugation. This procedure was repeated for a total of three times. Finally, peptides were dissolved in water (1 mL) containing 0.1% TFA (if required for solubility), and extracted with diethylether (10 mL) to remove traces of remaining scavengers. The ether phase was removed, and the aqueous phase was lyophilised to afford the solid peptides.

Cell Culture, Transfection and Immunostaining Experiments

Full-length OGFOD1 was cloned into either the pEGFP-C1 or pEGFP-N1 plasmid (Clontech, Palo Alto, Calif., USA). HeLa cells and human embryonic kidney (HEK) 293T cells were cultured in Dulbecco's modified Eagle's medium (DMEM) supplemented with 10% fetal calf serum, penicillin (50 U/ml) and streptomycin (50 ig/ml) at 37° C. in a 5% CO$_2$ atmosphere. For microscopy, cells were grown to 50-70% confluence on 18×18 glass coverslips and transfected with the indicated expression constructs using Lipofectamine 2000

(Invitrogen, CA, USA) according to the manufacturer's instructions. 24 hours after transfection cells were fixed with 3.7% formaldehyde in PBS for 10 minutes at room temperature, permeabilized with 1% Triton X-100 in PBS for 10 minutes, stained with antibodies, counterstained with 4',6-Diamidino-2-phenylndole (DAPI) (Sigma-Aldrich) and mounted in Vectashield (Vector Laboratories, CA, USA). The primary antibodies used were polyclonal anti-OGFOD1 (HPA003215; Sigma-Aldrich) and monoclonal anti-RPS23 (MCA3433Z; AbD Serotec).

GFP-Pulldown Experiments

Human embryonic kidney (HEK) 293T cells were transiently transfected with either GFP-OGFOD1 (pEGFP-C1; Clontech) or OGFOD1-GFP (pEGFP-N1; Clontech) or GFP only as a control experiment. Extracts from $1\times10^8$ cells were prepared in 1 mL lysis buffer (10 mM Tris/HCl pH 7.5, 300 mM NaCl, 0.5% NP40 supplemented with protease inhibitor cocktail (Sigma) and phosphatase inhibitor cocktails 1 & 2 (Sigma). After sonication ($3\times10$ s) and centrifugation supernatants were incubated with 100 µl of GFP-nanotrap (ChromoTek GmbH, Germany) (Rothbauer, Zolghadr et al. 2008) for 1 hour at 4° C. with constant rotation. After centrifugation the supernatant was removed, the beads washed three times with 500 µl of wash buffer (10 mM Tris/HCl pH 7.5, 300 mM NaCl) and the proteins were eluted in SDS-sample buffer and subjected to SDS-PAGE/Western blotting.

Protein Analysis by Mass Spectrometry

Proteins were separated by SDS-PAGE and stained by using the Colloidal Blue Staining Kit (Invitrogen). Protein bands were excised and digested with trypsin (Promega) according to published protocols (Batycka, Inglis et al. 2006).

The digested material was subjected to nano-ultra performance liquid chromatography tandem MS analysis (nano-UPLC-MS/MS) using a 75 µm-inner diameter×25 cm $C_{18}$ nanoAcquity™ UPLC™ column (1.7-µm particle size; Waters) and a 90 min gradient of 2-45% solvent B (solvent A: 99.9% $H_2O$, 0.1% HCOOH acid; solvent B: 99.9% MeCN, 0.1% HCOOH acid) on a Waters nanoAcquity UPLC system (final flow rate, 250 nl/min; 7000 psi) coupled to a Q-TOF Premier tandem mass spectrometer (Waters) run in positive ion mode. MS analysis was performed in data-directed analysis (DDA) mode (MS to MS/MS switching at precursor ion counts greater than 10 and MS/MS collision energy dependent on precursor ion mass and charge state). All raw MS data were processed using the PLGS software (version 2.3) including deisotoping and deconvolution (converting masses with multiple charge states to m/z=1). The mass accuracy of the raw data was corrected using Glu-fibrinopeptide (200 fmol/µl; 700 nl/min flow rate; 785.8426 Da $[M+2H]^{2+}$) that was infused into the mass spectrometer as a lock mass during analysis. MS and MS/MS data were calibrated at intervals of 30 s. MS/MS spectra (peak lists) were searched against the UniProtKB/Swiss-Prot database (Version 2010.07.16; 518, 415 sequences) database using Mascot version 2.3.01 (Matrix Science) and the following parameters: peptide tolerance, 0.2 Da; $^{13}C=1$; fragment tolerance, 0.1 Da; missed cleavages, 2; instrument type, ESI-Q-TOF; fixed modification, carbamidomethylation (C); and variable modifications, deamidation (N,Q) and oxidation (M,D,K,N,P,R). Analytical runs were repeated with an inclusion list for identified peptides with the highest ion score if arginine hydroxylation was detected. The interpretation and presentation of MS/MS data were performed according to published guidelines (Taylor and Goodlett 2005). Assignments of hydroxylation identified by Mascot were verified by manual inspection. Ion chromatograms were extracted using the mass windows of ±0.1 Da.

2: Optimization of Expression Conditions for OGFOD1 Production hsOGFOD1-FL-pET-28a was transformed into the *E. coli* expression strains BL21 (DE3), BL21 (DE3) pLysS and Rosetta 2 (DE3) (Stratagene/Agilent) according to the manufacturer's instructions. BL21 strains were grown on selective LB agar plates containing 30 µg/mL kanamycin as above, and pLysS and Rosetta 2 strains were grown on selective LB agar plates containing 30 µg/mL kanamycin and 33 µg/mL chloramphenicol. Expression trials were conducted with the aim of maximising the yield of soluble protein per volume of expression medium. A commercial media optimization kit (Athena Environmental Sciences Inc, Baltimore, Md. 21227) containing four proprietary expression media (TurboBroth, PowerBroth, SuperiorBroth, HyperBroth) was used in addition to three reference media (LB (Miller), Glucose M9Y, 2YT) was used to find the optimal medium formulation. IPTG concentrations were varied in the range of 0.2 to 2 mM.

For expression trials, a single colony was picked from the transformation plate, resuspended in 100 mL LB (Miller)+Kanamycin medium and grown in an environmental shaker at 37° C. overnight. On the next day, flasks containing 100 mL of expression medium+kanamycin were inoculated with 1 mL of the overnight culture each and grown in an environmental shaker at 37° C. until the cultures had reached $OD_{600}$ 0.6. At this stage, the cultures were shifted to the target temperature (18° C., 30° C., and 37° C.) for 30 minutes, after which IPTG was added to each to a final concentration of 1 mM. Samples of 1.5 mL were taken after 4 hours and 18 hours of induction, after which cells were collected by centrifugation and stored at −80° C. The cell pellets were resuspended in 300 µL of BugBuster®+Lysonase® reagent (Merck, Darmstadt, Germany) (a proprietary mixture of detergents, recombinant lysozyme and recombinant DNAse I) and incubated at room temperature for 15-20 min with slow shaking A sample was drawn for total protein analysis. The remainder was centrifuged (14.000 rpm, 20 min, 4° C.). The supernatant was used as the soluble fraction. Total and soluble fractions were analysed by SDS-PAGE (data not shown).

SDS-PAGE analysis revealed that high levels of soluble expression could be achieved using an expression temperature of 30° C., expression strain BL21 (DE3), PowerBroth fermentation medium, and overnight induction (18 hrs) with 1-2 mM IPTG.

3: Identification of OGFOD1 as a 2OG Oxygenase

Crystallographic analyses have revealed that all structurally characterised 2OG oxygenases contain a double-stranded beta-helix (DSBH or jelly-roll) fold (McDonough, Loenarz et al.; Clifton, McDonough et al. 2006). In the case of OGFOD1, sequence analyses predict that it contains two such folds, with the N-terminal of these likely being the catalytic domain; Structural analyses on the yeast enzyme TPA1 which is related to OGFOD1, and also of unknown function, support this proposal. (Keeling, Salas-Marco et al. 2006; Henri, Rispal et al. 2010; Kim, Kim et al. 2010).

Many, but not all, 2OG oxygenases catalyze substantial turnover of 2OG in the absence of their 'prime' substrate (Welford, Schlemminger et al. 2003). Initially, we therefore prepared purified full-length recombinant OGFOD1 and its C-terminal domain (both >95% by SDS-PAGE analysis) and tested them for 2OG turnover activity. (Studies on the yeast homologue, TPA1, had been unsuccessful in obtaining a construct of the N-terminal domain alone (Kim, Kim et al. 2010)).

Results of 2OG turnover assays with full-length OGFOD1 are shown in FIG. 3. The results reveal that OGFOD1-catalyzed 2OG turnover is stimulated by the cofactor Fe(II), and inhibited by pyridine 2,4-dicarboxylic acid, which is an inhibitor of many 2OG oxygenases. Activity is also stimulated significantly in the presence of a peptide fragment of the RPS23 protein. 2OG turnover activity is stimulated to a lesser extent by the addition of ascorbate, which is in contrast to the hypoxia inducible factor prolyl hydroxylases, which exhibit strong dependence on ascorbate.

2OG turnover assays with OGFOD1 C-terminal domain also revealed that only full-length protein, but not the C-terminal domain alone, are capable of significantly stimulating uncoupled turnover, thus showing that the N-terminal domain of OGFOD1 is the catalytic 2OG oxygenase domain (data not shown).

These results define OGFOD1 as a 2OG oxygenase, in which the N-terminal of the two DSBH folds is the catalytic domain.

To demonstrate that a functional iron binding triad of residues is required for OGFOD1 activity, site-directed mutagenesis was performed to replace the H155 and D157 residues of the catalytic triad with alanine H155A and D157A variants were expressed, purified and activity was assayed by MALDI mass spectrometry. While a clear +16 mass shift was observed upon incubation of RPS23 peptide with wild-type OGFOD1, no such change was detectable with the H155A or D157A variants under standard assay conditions (data not shown). Thus, both H155 and D157 are essential for catalytic activity of wild-type OGFOD1.

4: Analysis of the Sub-Cellular Localization of OGFOD1 and Identification of OGFOD1-Interacting Proteins We then analysed the subcellular localization of OGFOD1. HeLa cells transiently overexpressing OGFOD1-GFP or GFP-OGFOD1, respectively, displayed fluorescence exclusively in the nucleus. Moreover, immunocytochemistry with a polyclonal anti-OGFOD1 antibody (Sigma) showed a speckled pattern throughout the nucleus, with a slight increase of signal in nucleoplasmatic regions (data not shown). These results are consistent with previous work (Saito, Adachi et al. 2010) and the presence of a N-terminal nuclear localization sequence (NLS) in OGFOD1 (residues 1-19).

In order to identify potential OGFOD1 substrates we then carried out co-immunoprecipitation analyses in human embryonic kidney (HEK) 293T cells employing OGFOD1 N- or C-terminally labelled with green fluorescent protein (GFP)-tagged OGFOD1 and purification using appropriate antibodies coupled to MS-based identification. With all tested protein fusion tags, one of the identified OGFOD1 binding partners was identified as the ribosomal protein RPS23.

5: Analysis of OGFOD1 Binding Partners

Using a mass spectrometry-based assay (MALDI-TOF), we then screened >300 known peptide fragments of substrates for three human 2OG oxygenases (PHD2, FIH), that encompass known hydroxylation/demethylation sites, including the HIF-1α N- and C-terminal oxygen dependent degradation domain (NODD and CODD, prolyl-hydroxylation), the HIF-1α C-terminal transcriptional activation domain (CTAD, asparaginyl-hydroxylation), ankyrin repeat domain peptides (ARD, asparaginyl-hydroxylation), and collagen prolyl-hydroxylase peptide-substrates, for modification by OGFOD1. None of these potential substrates displayed evidence of a +16 Da mass shift characteristic of hydroxylation. Neither did we find that OGFOD1 catalyzed $N^\epsilon$-methyl-lysine or arginyl demethylation of histone fragment peptides, as do the JmjC enzymes (data not shown).

To test whether OGFOD1 catalyzes hydroxylation at one or more sites of RPS23, we then prepared peptide fragments based on the entire RPS23 protein sequence and tested them as RPS23 substrates in vitro. We found that peptides containing Pro-62, but none of the other peptides tested, were subject to OGFOD1-catalyzed hydroxylation.

In addition, LC-MS/MS analysis of endogenous RPS23 after immunoprecipitation of GFP-tagged OGFOD1 revealed at least 85% of Pro-62 to be hydroxylated (data not shown). MS analysis with synthetic normal or prolyl-hydroxylated RPS23 $^{61}$QPNSAIR$^{67}$ peptides as standards was used to confirm the occurrence of hydroxylated and non-hydroxylated Pro-62 in endogenous protein samples (data not shown). This strongly suggests that OGFOD1-catalyzed prolyl hydroxylation of RPS23 is a bona fide posttranslational protein modification.

6: Assignment of Hyp-P62 in RPS23 Purified from Mammalian Ribosomes

Ribosomes were isolated from tissue (mouse liver and kidney) and cultured cell lines (e.g., HEK293, HeLa, and U2OS) using well-established protocols described in full by Madjar (Cell Biology: A Laboratory Handbook (J. E. Celis, ed) pp. 657-661 Academic Press, New York) and Belin (Curr. Protoc. Cell Biol.: Unit 3.40, 2010). Essentially, contaminating non-ribosomal proteins and RNA molecules were removed by cell fractionation to produce a post-mitochondrial supernatant that was passed through a sucrose cushion at 100,000×g for 4 h in a Beckmann ultracentrifuge (SW-28 rotor) in order to sediment purified ribosomal complexes. Proteins were extracted from the ribosomal pellet by addition of magnesium chloride and glacial acetic and precipitated by addition of acetone.

To separate RPS23 from the ribosomal preparation an HPLC method was employed. Acetone precipitated, lyophilised protein pellets were resuspended in 2% glacial acetic acid, prior to separation on an Agilent 1200 system with a Vydac 214TP column (250×4.6 mm, particle size 5 µm. Reversed phase separation of RPS23 used a mobile phase of buffer A (buffer A: 0.1% trifluoroacetic acid in water) and buffer B (0.08% trifluoroacetic acid in acetonitrile). Flow rate was set at 1 mL/min with the following gradient optimised for the separation of RPS23: 0.01 min-10% B; 10 min-10% B; 25 min-20% B; 180 min-43% B; 185 min-95% B. All experiments were performed at room temperature with the UV detector set at 214 nm. Under these assay conditions, RPS23 was shown to co-elute with one other protein, RPL8, at 103-104 min. Fractions containing RPS23 were lyophilised by vacuum centrifugation, prior to solubilisation in Laemmli sample buffer and SDS-PAGE analysis followed by Coomassie Blue staining Species corresponding to RPS23 were subject to in-gel proteolysis with either trypsin or Arg-C endoproteinases according to published protocols (Batycka, Inglis et al. 2006). The digested material was subjected to nano-UPLC MS/MS (nanoAcquity UPLC coupled to a Q-T of Premier tandem mass spectrometer; Waters) run in positive ion mode.

Using this methodology we demonstrate P62 hydroxylation in normal mouse tissue (not shown) and a range of common human cancer cell lines, including HeLa (not shown), HEK293 (not shown) and U2OS. Interestingly, we were unable to assign the unmodified peptide in any of our preparations. Furthermore, interrogation of the precursor ion data did not reveal any co-eluting precursor ions of the predicted mass for the unhydroxylated species, suggesting that hydroxylation of RPS23 in tissue and cell lines in the steady state is greater than 95% (data not shown).

7: Identification of the Site and Stereochemistry of Hydroxylation by OGFOD1

OGFOD1-mediated hydroxylation of the initially identified 20mer peptide sequence of human RPS23 was strictly dependent on presence of 2OG and Fe(II), and hydroxylation was reduced in presence of 1 mM of generic 2OG oxygenase inhibitors such as N-oxalyl glycine (NOG), pyridine 2,4-dicarboxylic acid (2,4-PDCA) and transition metal ions such as $Co^{II}$. This behaviour is comparable to that of many 2OG oxygenases. Interestingly, OGFOD1 activity was apparently not stimulated by the presence of ascorbate (data not shown). This is in contrast to the HIF prolyl hydroxylases which exhibit a dependence on ascorbate or other reducing agents (Flashman, Davies et al.).

Because of its close sequence and predicted structural similarity with the PHDs, we initially considered it likely that OGFOD1 catalyzes trans-4-prolyl hydroxylation as observed for PHD2. To test this proposal, we carried out amino acid analysis on the product of incubation of RPS23 with OGFOD1 (data not shown). Standards of cis- and trans-3- and 4-hydroxy-L-proline could be separated by HPLC, using established pre-column derivatization procedures employing phthaldialdehyde and Fmoc-Cl. The results clearly demonstrate the presence of trans-3-hydroxyproline in the enzymatic product (data not shown). There was no evidence for cis-3-prolyl- or cis/trans-4-prolyl-hydroxylation. In addition, spiking of the analyte prepared from the enzymatic reaction, with individual standards, resulted in co-elution of the enzymatic product with trans-3-hydroxyproline, but none of the three other isomers tested (data not shown).

8: Specificity of OGFOD1

To investigate the specificity of OGFOD1 towards variations in the sequence and length, multiple corresponding to RPS23 and RPS23-like sequences were synthesized and tested. MALDI assays were performed using a 1:25 protein:peptide (4 µM/100 µM) ratio, with incubation at 37° C. for 30 min. The results are shown in the table below.

Mutation of prolyl to alanine or isoleucine residues completely abolished hydroxylation, providing further evidence for OGFOD1 acting as a prolyl hydroxylase. Among the remaining residues, alanine mutation of the asparagines and serine residues immediately following the prolyl residue resulted in the largest relative drop in hydroxylation levels, while mutagenesis of individual other residues was well-tolerated. This observation is consistent with the high evolutionary conservation of the amino acids following, but not of those preceding the prolyl (Pro-62) residue in RPS23. No hydroxylation of the PHD2 C-terminal oxygen-dependent degradation domain (CODD) substrate by OGFOD1 was observed under the same assay conditions.

| Peptide | Sequence | Hydroxylation |
|---|---|---|
| RPS23 20mer | VLEKVGVEAKQPNSAIRKCV (SEQ ID NO: 16) | ++ |
| RPS23 16mer | EKVGVEAKQPNSAIRK (SEQ ID NO: 17) | + |
| S. Pombe RPS23 | VVEKIGVEAKQPNSAIRKCV (SEQ ID NO: 18) | ++ |
| S. Cerevisiae RPS23 | VLEKLGIESKQPNSAIRKCV (SEQ ID NO: 19) | ++ |
| E. Coli S12 | CTRVYTTTPKKPNSALRKVC (SEQ ID NO: 20) | - |
| K04A | VLEAVGVEAKQPNSAIRKCV (SEQ ID NO: 21) | ++ |
| V05A | VLEKAGVEAKQPNSAIRKCV (SEQ ID NO: 22) | ++ |
| G06A | VLEKVAVEAKQPNSAIRKCV (SEQ ID NO: 23) | ++ |
| V07A | VLEKVGAEAKQPNSAIRKCV (SEQ ID NO: 24) | ++ |
| E08A | VLEKVGVAAKQPNSAIRKCV (SEQ ID NO: 25) | ++ |
| K10A | VLEKVGVEAAQPNSAIRKCV (SEQ ID NO: 26) | ++ |
| Q11A | VLEKVGVEAKAPNSAIRKCV (SEQ ID NO: 27) | ++ |
| P12A | VLEKVGVEAKQANSAIRKCV (SEQ ID NO: 28) | - |
| P12I | VLEKVGVEAKQINSAIRKCV (SEQ ID NO: 29) | - |
| N13A | VLEKVGVEAKQPASAIRKCV (SEQ ID NO: 30) | + |
| S14A | VLEKVGVEAKQPNAAIRKCV (SEQ ID NO: 31) | + |
| I16A | VLEKVGVEAKQPNSAARKCV (SEQ ID NO: 32) | ++ |
| R17A | VLEKVGVEAKQPNSAIAKCV (SEQ ID NO: 33) | N.D. |
| K18A | VLEKVGVEAKQPNSAIRACV (SEQ ID NO: 34) | ++ |
| C19A | VLEKVGVEAKQPNSAIRKAV (SEQ ID NO: 35) | ++ |

9: Identification of OGFOD1-Stabilizing Compounds by Thermal Stability Shift Assay The effect of small molecules on the stability of proteins to thermal denaturation was assessed by the change in apparent protein melting temperature, defined as the temperature at which equal amounts of folded and unfolded protein exist in solution. Unfolding was quantified by measurement of the fluorescence increase of SYPRO® Orange dye (Invitrogen) upon binding to hydrophobic residues that are exposed during unfolding. Approximately 400 small-molecule compounds were tested at a final concentration of 20 µM. Stabilization data for selected compounds are shown in below. Structures of the compounds are set out below.

These compounds or derivatives thereof could be used to guide the design of OGFOD1 inhibitors. Further, such compounds or derivatives could be used increase the stability of OGFOD1 protein so as to achieve modulation of OGFOD1 activity, or to achieve crystallization of the OGFOD1 protein in complex with such compound.

| Compound | Molecular Formula | Class | Stabilization (° C.) |
|---|---|---|---|
| 1 | $C_{13}H_{12}N_2O_3$ | Isoquinoline derivative | +8.4 |
| 2 | $C_{15}H_{14}N_2O_4$ | Diacylhydrazine derivative | +7.1 |
| 3 | $C_{10}H_{12}N_2O_5S$ | Sulfonylhydrazine derivative | +7.1 |
| 4 | $C_{12}H_9ClN_2O_4$ | FG2216 | +7.0 |
| 5 | $C_{12}H_8N_2O_4$ | Bipyridyl derivative | +7.5 |
| 6 | $C_9H_9BrN_2O_3$ | 2OG derivative | +7.0 |
| 7 | $C_{11}H_6N_2O_3$ | 4-hydroxyquinoline-3-carboxylate derivative | +7.5 |
| 8 | $C_{10}H_{12}O_5$ | Prohexadione | +6.9 |
| 9 | $C_5H_7NO_5$ | N-oxalyl amino acid derivative | +6.3 |
| 10 | $C_{13}H_{12}N_2O_4$ | 3-hydroxyquinoline derivative | +7.2 |
| 11 | $C_7H_5NO_4$ | Pyridine 2,4-dicarboxylic acid | +6.7 |

The structures of these compounds are provided below:

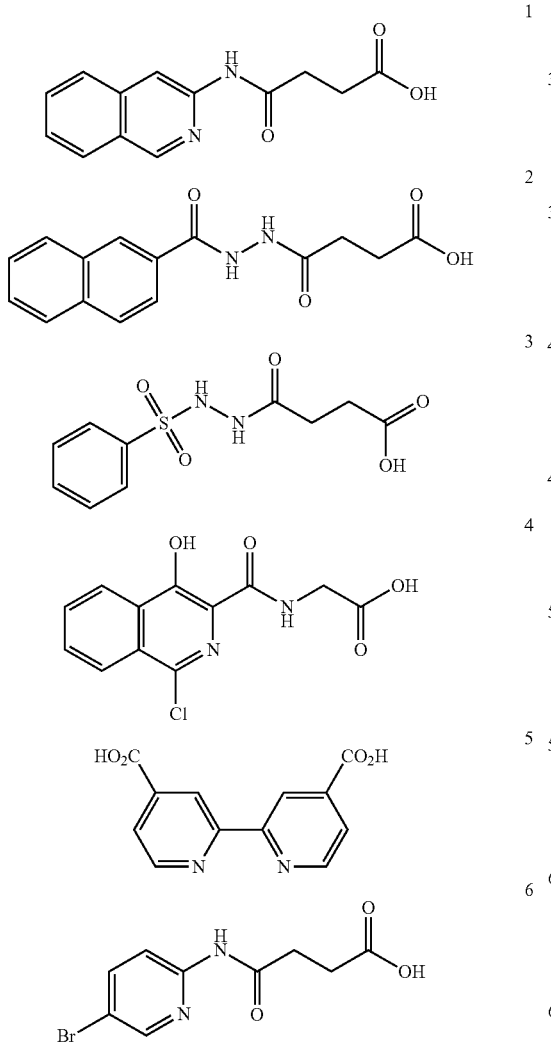
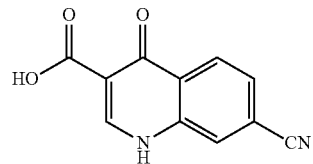
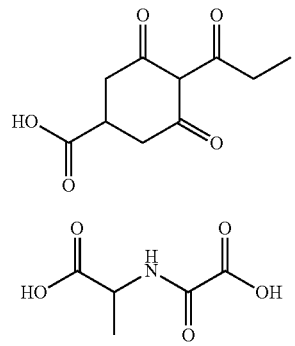
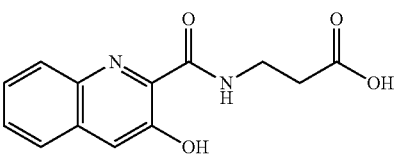
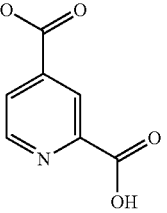

10: Inhibition of OGFOD1

Figure 5:
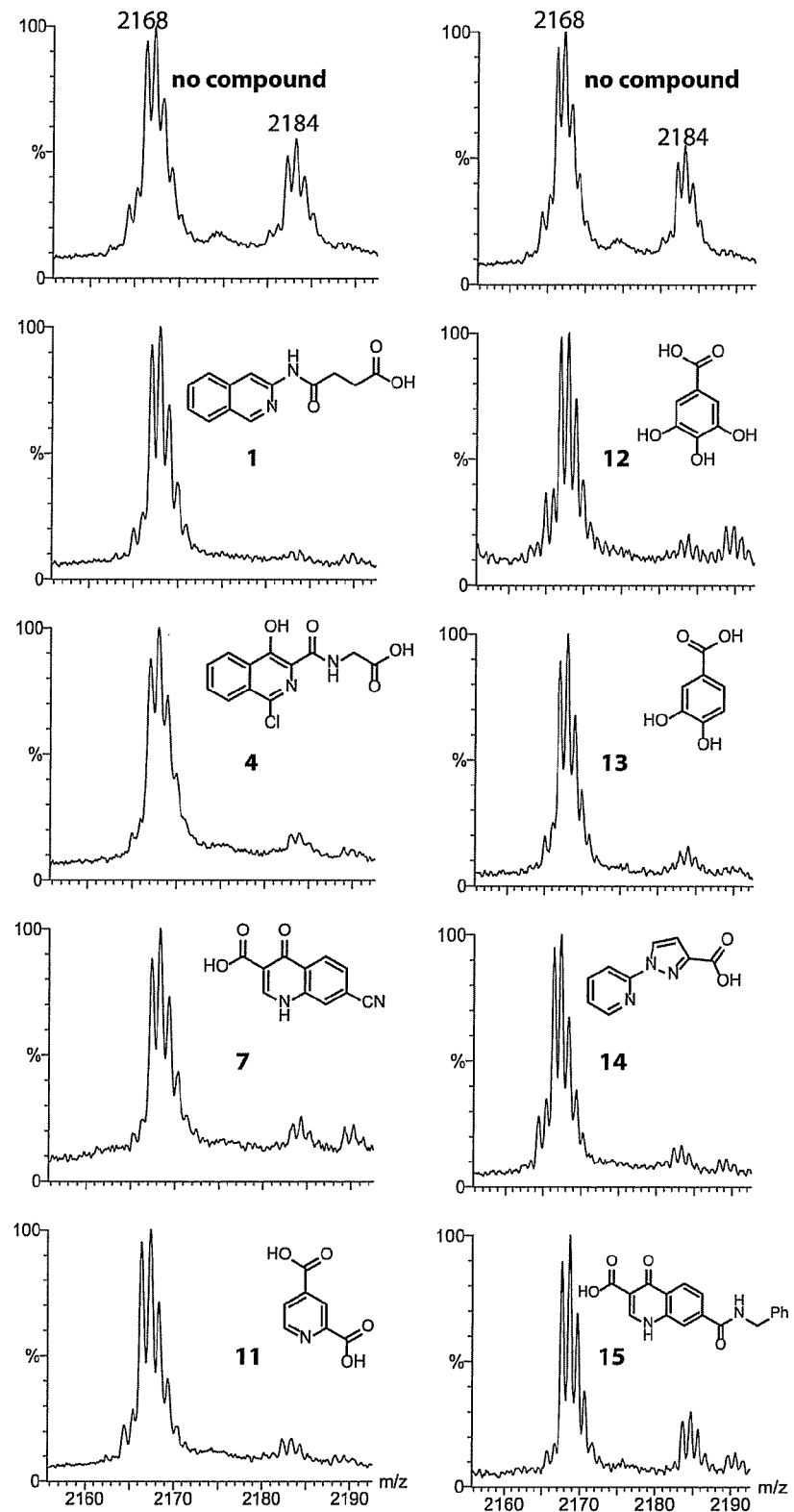
FIGS. 5 and 6 show original MALDI spectra demonstrating inhibition of recombinant full-length human OGFOD1 protein (SEQ ID NO:1) by the inhibitors given in the examples.
Figure 6:
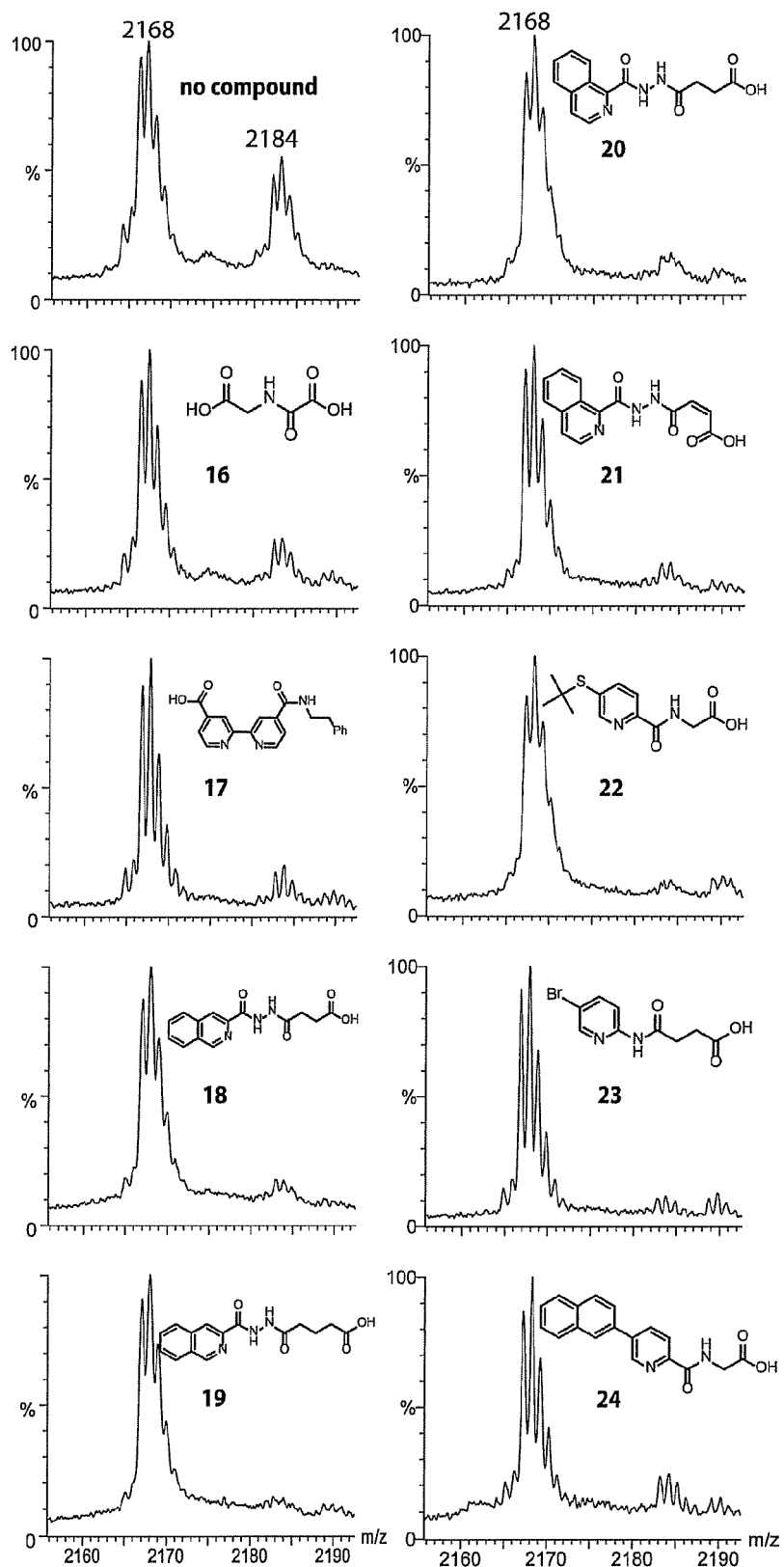

A library of 150 compounds comprising known and potential inhibitors of 2OG oxygenases was screened against OGFOD1 by a MALDI-based hydroxylation assay. Single-point measurements were conducted in duplicate, using 4 µM OGFOD1 at 100 µM final compound concentration in the presence of excess (300 µM) 2OG, with incubation at 37° C. for 30 min. Structures of hit compounds that resulted in a significant reduction of hydroxylation levels are shown below, and original MALDI spectra are given in FIGS. 5 and 6.

| Compound | Molecular Formula | Class |
|---|---|---|
| 1 | $C_{13}H_{12}N_2O_3$ | Isoquinoline derivative |
| 4 | $C_{12}H_9ClN_2O_4$ | FG2216 |
| 7 | $C_{11}H_6N_2O_3$ | 4-hydroxyquinoline-3-carboxylate derivative |
| 11 | $C_7H_5NO_4$ | Pyridine 2,4-dicarboxylic acid |
| 12 | $C_7H_6O_5$ | Catechol derivative |
| 13 | $C_7H_6O_4$ | Catechol derivative |
| 14 | $C_9H_7N_3O_2$ | Pyridine-2-yl-1H-pyrazole derivative |
| 15 | $C_{18}H_{14}N_2O_4$ | 4-hydroxyquinoline-3-carboxylate derivative |
| 16 | $C_4H_5NO_5$ | N-oxalyl amino acid derivative |
| 17 | $C_{20}H_{17}N_3O_3$ | Bipyridyl derivative |

-continued

| Compound | Molecular Formula | Class |
|---|---|---|
| 18 | C₁₄H₁₃N₃O₄ | Diacylhydrazine derivative |
| 19 | C₁₅H₁₅N₃O₄ | Diacylhydrazine derivative |
| 20 | C₁₄H₁₃N₃O₄ | Diacylhydrazine derivative |
| 21 | C₁₄H₁₁N₃O₄ | Diacylhydrazine derivative |
| 22 | C₁₂H₁₆N₂O₃S | N-acyl glycine derivative |
| 23 | C₉H₉BrN₂O₃ | 2-aminopyridine derivative |
| 24 | C₁₈H₁₄N₂O₃ | N-acyl glycine derivative |

The structures of these compounds are provided below:

1

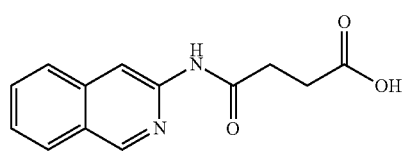

4

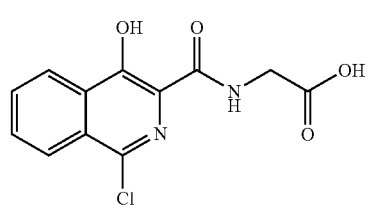

7

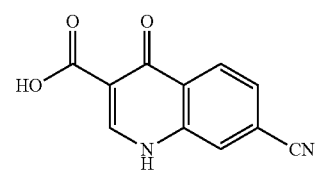

11

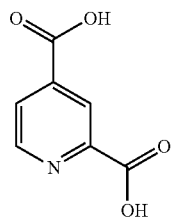

12

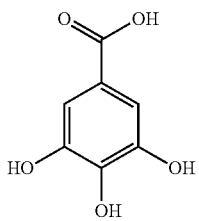

13

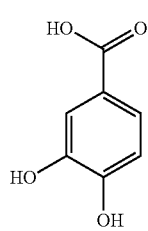

-continued

14

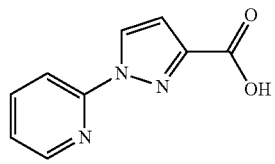

15

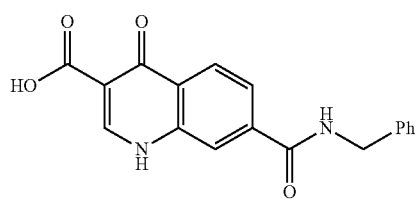

16

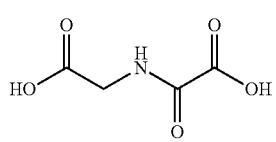

17

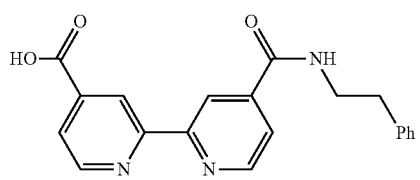

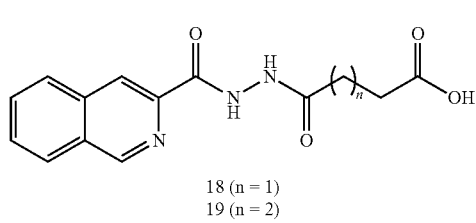

18 (n = 1)
19 (n = 2)

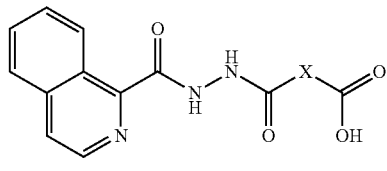

20 (X = (CH₂)₂)
21 (X = Z—(CH=CH))

22

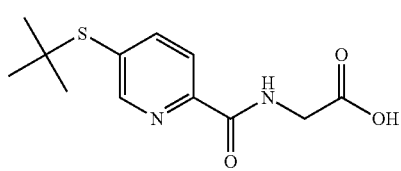

23

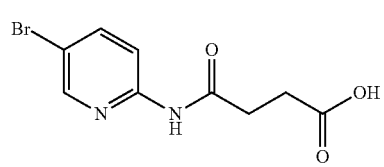

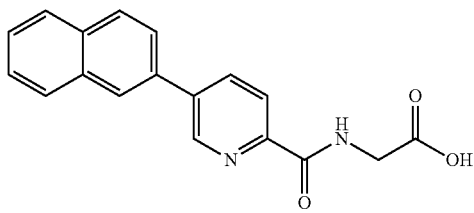

24

11: Discussion on Potential Therapeutic Applications of the Discovery that OGFOD1 Catalyses Hydroxylation of a Ribosomal Protein Experimental evidence supports a role for agents that modulate OGFOD1 as novel treatment for some viral and genetic diseases on the basis of translational fidelity.

RPS23, and its homologues, have been implicated in controlling the accuracy of the translation process. During translation, tRNA selection occurs at the highly conserved decoding centre. The decoding centre controls the stringency of codon-anticodon recognition and the susceptibility of the translation process to recoding events, such as ribosome hopping, translational frameshifting and premature translation termination. Mutations in the E. coli and yeast homologues of RPS23 directly affect translational accuracy (Toivonen, J. M. et al. 1999; Anthony, R. A. & Liebman, S. W. 1995). Furthermore, the prolyl residue in the prokaryotic homologue RPS12 which is analogous to Pro-62 in RPS23, is located directly at the decoding centre of the prokaryotic *Thermus thermophilus* ribosome (Schmeing, T. M et al. 2009). This data suggests that OGFOD1 may play a role in translational accuracy.

Extensive efforts have been directed at the modulation of translational accuracy using small molecules for the treatment of genetic diseases which are characterized by the presence of premature termination codons. Premature termination codons result in the expression of truncated protein products. One possible therapeutic approach is based on the reduction of translational accuracy and an increase in termination or stop codon readthrough, such that sufficient levels of full-length protein are produced to revert the disease phenotype. Although aminoglycosides have shown some promise in promoting stop codon readthrough, their clinical efficacy is usually limited by their high toxicity.

Interestingly, there is data to support a role for the *S. cerevisiae* homologue of OGFOD1 (Tpa1) in translation termination and stop-codon readthrough (Keeling, K. M. et al. 2006). Modulators of OGFOD1 could therefore be used as novel treatments for diseases caused by premature termination codons. Such diseases include muscular dystrophy, cystic fibrosis, haemophilia and retinitis pigmentosa.

Other therapeutic applications for modulators of OGFOD1 include combating retroviruses (Bidou et al. 2010). Several retroviruses, including HIV, rely heavily on ribosomal frameshifting processes which enable them to encode multiple proteins on a single continuous stretch of genomic RNA. Bidou et al. suggest that rational drug design against ribosomal proteins could facilitate novel therapies for combating retroviruses by modulating translational accuracy and blocking their ability to replicate. It should be noted that overall structural integrity is important for most ribosomal proteins to allow assembly of ribosomal subunits, limiting the use of drugs which directly target the ribosomal proteins.

Targeting post-translational ribosomal protein modifications such as OGFOD1-catalyzed prolyl-hydroxylation of RPS23 opens the way to controlling a post-translational modification located directly at the ribosomal decoding centre, whilst also allowing inhibitor design against a family of well-established and validated targets, i.e. 2OG oxygenases, rather than ribosomal proteins.

The presence or absence of hydroxylation on the RPS23 protein could be exploited to develop chemical agents that selectively modulate ribosomal activity (i.e. translation) in cells that contain hydroxylated or non-hydroxylated RPS23. In solid tumours and other hypoxic tissues, oxygen-dependent and OGFOD1-dependent hydroxylation of RPS23 would be reduced compared to healthy normoxic tissues. Thus, the absence of a hydroxyl group in hypoxic tissues could be used to design inhibitors of protein translation that display selective activity in hypoxic tissues, with potential applications including, but not limited to, the treatment of solid tumours. Alternatively, chemical agents could be developed that selectively modulate, i.e. increase or decrease the fidelity of translation, in cells with non-hydroxylated RPS23. Because both increased and decreased translational fidelity can negatively affect the competitive fitness of a (cancer) cell, such modulators could also be used to develop novel chemotherapeutic agents which selectively target hypoxic versus normoxic tissues, thus potentially reducing the side effects commonly observed with anticancer drugs. Many ribosome inhibitors are known and some existing inhibitors, or derivatives thereof, may selectively inhibit non-hydroxylated versus hydroxylated ribosomes.

Further, in conjunction with a suitable analytical tool, such as an assay for RPS23 hydroxylation in cells as disclosed in this patent application, potential correlations between RPS23 hydroxylation in (cancer) cells and characteristics of tumour cells could be studied, with the aim of developing tumour biomarkers based on the degree of RPS23 hydroxylation. As a potential predictive tumour biomarker, RPS23 hydroxylation levels could be used to predict the risk of disease relapse or death of patients, so enabling categorization into "high-risk" and "low-risk" groups. Alternatively, as a potential prognostic tumour biomarker, RPS23 hydroxylation status in tissues could provide a means of assessing the likelihood of success of specific well-established chemotherapeutic treatments, thus aiding clinicians in the selection of the most suitable therapy regimen for a particular patient.

The invention claimed is:

1. A method for assaying 2-oxoglutarate and iron-dependent oxygenase domain containing 1 (OGFOD1) activity, the method comprising contacting a peptide comprising a prolyl residue, with an OGFOD1 polypeptide and determining whether the prolyl residue in said peptide is hydroxylated, wherein the OGFOD1 polypeptide comprises:
   (a) the amino acid sequence of SEQ ID NO: 1;
   (b) a variant thereof having at least 90% identity thereto and having prolyl hydroxylase activity; or
   (c) a fragment of either thereof having prolyl hydroxylase activity.

2. A method according to claim 1 wherein said peptide comprises a ribosomal protein.

3. The method according to claim 1, wherein the peptide is the human ribosomal protein RPS23 (SEQ ID NO:6).

4. The method according to claim 1 wherein the peptide comprises:
   (a) the amino acid sequence of SEQ ID NO: 6;
   (b) a variant thereof having at least 90% identity to SEQ ID NO: 6 and comprising a proline equivalent to proline at position 62 of SEQ ID NO: 6;
   (c) a fragment of (a) or (b) of at least 6 amino acids in length and comprising proline at position 62 of SEQ ID NO: 6, or a proline at a position equivalent to proline at position 62 of SEQ ID NO: 6.

5. The method according to claim 1, wherein the method is carried out in the presence of Fe(II) and 2-oxoglutarate.

6. The method according to claim 5, wherein the method is carried out in the presence of a reducing agent.

7. The method according to claim 1, wherein the assay is carried out in the presence of a test agent to determine whether the test agent is a modulator of OGFOD1 activity.

8. The method of claim 7, wherein the method further comprises determining whether the test agent modulates the activity of a 2-oxoglutarate dependent oxygenase other than OGFOD1, thereby determining whether the test agent selectively modulates the activity of the 2-oxoglutarate dependent oxygenase other than OGFOD1.

9. The method according to claim 7, wherein the test agent is a reported inhibitor of a 2OG oxygenase other than OGFOD1, or an analogue or variant of such an inhibitor.

10. The method according to claim 7, wherein the test agent is a reported inhibitor of a 2OG oxygenase other than OGFOD1 selected from an N-oxalyl amino acid, N-oxalylglycine or a derivative thereof, a glycine or alanine derivative, a 2-oxoacid analogue, a flavonoid or flavonoid derivative, or genistein.

11. A method for identifying an inhibitor of OGFOD1 oxygenase activity, the method comprising contacting an OGFOD1 polypeptide and a proline containing peptide with a test agent under conditions suitable for oxygenase activity, and monitoring for hydroxylation of the proline of said peptide to give a trans-3-hydroxy prolyl residue, wherein the OGFOD1 polypeptide comprises:
   (i) the amino acid sequence of SEQ ID NO: 1;
   (ii) a variant thereof having at least 90% identity thereto and having prolyl hydroxylase activity; or
   (iii) a fragment of either thereof having prolyl hydroxylase activity.

12. The method according to claim 11, wherein the test agent is a reported inhibitor of a 2OG oxygenase other than OGFOD1, or an analogue or variant of such an inhibitor, wherein the inhibitor is selected from an N-oxalyl amino acid, N-oxalylglycine or a derivative thereof, a glycine or alanine derivative, a 2-oxoacid analogue, a flavonoid or flavonoid derivative, or genistein.

13. A method for introducing trans-3-hydroxyprolyl residue into a peptide or protein comprising contacting a peptide or protein containing a prolyl residue with an OGFOD1 polypeptide, wherein the OGFOD1 polypeptide comprises:
   (i) the amino acid sequence of SEQ ID NO: 1;
   (ii) a variant thereof having at least 90% identity thereto and having prolyl hydroxylase activity; or
   (iii) a fragment of either thereof having prolyl hydroxylase activity.

14. A method for identifying a modulator of protein translation, the method comprising contacting a cell which expresses OGFOD1 with a test agent and determining whether the test agent modulates the OGFOD1 mediated regulation of protein translation, wherein the OGFOD1 polypeptide comprises:
(i) the amino acid sequence of SEQ ID NO: 1;
(ii) a variant thereof having at least 90% identity thereto and having prolyl hydroxylase activity; or
(iii) a fragment of either thereof having prolyl hydroxylase activity.

15. A method according to claim 14, wherein the cell comprises a protein translation reporter construct and the method comprises determining whether OGFOD1-mediated regulation of protein translation of the reporter construct is modulated by the test agent.

16. A method for modulating prolyl hydroxylation by OGFOD1 of a ribosomal protein or a fragment or variant thereof comprising a prolyl residue, or for modulating protein translation, the method comprising contacting a cell with an inhibitor or activator of 2OO oxygenase activity, wherein the OGFOD1 polypeptide comprises:
(i) the amino acid sequence of SEQ ID NO: 1;
(ii) a variant thereof having at least 90% identity thereto and having prolyl hydroxylase activity; or
(iii) a fragment of either thereof having prolyl hydroxylase activity.

* * * * *